(12) United States Patent
Meng et al.

(10) Patent No.: US 8,846,569 B2
(45) Date of Patent: Sep. 30, 2014

(54) PESTICIDAL BIS-ORGANOSULFUR COMPOUNDS

(75) Inventors: Charles Q. Meng, Johns Creek, GA (US); Matthias Pohlman, Freinsheim (DE); Henricus Maria Martinus Bastiaans, Chapel Hill, NC (US); Ralph Paulini, Bad Duerkheim (DE); Sebastian Soergel, Ludwigshafen (DE)

(73) Assignees: Merial Limited, Duluth, GA (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/511,736

(22) PCT Filed: Dec. 5, 2010

(86) PCT No.: PCT/US2010/059011
§ 371 (c)(1),
(2), (4) Date: Jul. 24, 2012

(87) PCT Pub. No.: WO2011/069143
PCT Pub. Date: Jun. 9, 2011

(65) Prior Publication Data
US 2012/0283094 A1 Nov. 8, 2012

Related U.S. Application Data

(60) Provisional application No. 61/266,755, filed on Dec. 4, 2009.

(51) Int. Cl.
| | |
|---|---|
| C07C 317/28 | (2006.01) |
| A01C 1/06 | (2006.01) |
| A01N 37/34 | (2006.01) |
| A01N 43/40 | (2006.01) |
| A01P 1/00 | (2006.01) |
| A61K 31/275 | (2006.01) |
| A61K 31/44 | (2006.01) |
| A61P 33/00 | (2006.01) |
| C07D 213/57 | (2006.01) |
| A01N 43/653 | (2006.01) |
| A01N 43/82 | (2006.01) |
| A01N 41/10 | (2006.01) |
| C07C 323/60 | (2006.01) |
| A01N 47/02 | (2006.01) |
| C07D 213/64 | (2006.01) |
| A01N 43/56 | (2006.01) |
| C07C 327/42 | (2006.01) |
| C07C 323/65 | (2006.01) |
| C07D 231/12 | (2006.01) |
| A01N 37/36 | (2006.01) |

(52) U.S. Cl.
CPC ............ *C07C 323/65* (2013.01); *A01N 43/653* (2013.01); *A01N 43/82* (2013.01); *A01N 41/10* (2013.01); *C07C 323/60* (2013.01); *A01N 47/02* (2013.01); *A01N 43/40* (2013.01); *C07D 213/64* (2013.01); *A01N 43/56* (2013.01); *C07C 327/42* (2013.01); *C07D 231/12* (2013.01); *A01N 37/36* (2013.01)
USPC ........... 504/100; 514/357; 514/526; 546/330; 558/437

(58) Field of Classification Search
None
See application file for complete search history.

(56) References Cited

U.S. PATENT DOCUMENTS 4,036,970 A  7/1977  Walker et al.

FOREIGN PATENT DOCUMENTS

| JP | 09031049 | * 2/1997 |
|---|---|---|
| WO | WO 2008/143332 | 11/2008 |

OTHER PUBLICATIONS

"New trifluoropropanone sulfides as highly active and selective inhibitors of insect juvenile hormone esterase," Szekacs A. et al., *Pesticide Biochemistry and Physiology*, 1989, vol. 33(2), pp. 112-124.

* cited by examiner

*Primary Examiner* — Janet L Andres
*Assistant Examiner* — Timothy R Rozof
(74) *Attorney, Agent, or Firm* — Judy Jarecki-Black; John Ezcurra; Merial Limited

(57) ABSTRACT

The present invention provides bis-organosulfur compounds of formulae (I) and (II) and compositions comprising the compounds that are effective against animal pests, including parasites. The compounds and compositions may be used for combating parasites in or on birds and mammals and for combating pests that damage crops, plants and plant propagation material. The invention also provides for an improved method for eradicating, controlling and preventing parasite infestation in birds and mammals.

26 Claims, No Drawings

PESTICIDAL BIS-ORGANOSULFUR COMPOUNDS

CROSS-REFERENCE TO RELATED APPLICATIONS

This application is a U.S. national stage application of International Application No. PCT/US2010/059011, filed Dec. 5, 2010, which claims the benefit of priority to U.S. Provisional Patent Application No. 61/266,755 filed Dec. 4, 2009, which is incorporated herein by reference in its entirety.

FIELD OF THE INVENTION

The present invention is directed to new bis-organosulfur compounds with insecticidal and parasiticidal activity and compositions comprising the compounds. The present invention also provides methods for eradicating, controlling, and preventing parasite infestation and/or infection in birds, fish and mammals, and for treating and preventing plants and plant propagation material from attack or infestation by pests. The compounds of the invention may be administered to animals, particularly mammals, fish and birds, to prevent or treat parasitic infestation and/or infection.

BACKGROUND OF THE INVENTION

Animal pests such as insects and parasitic nematodes destroy growing and harvested crops and attack wood-containing structures, causing significant economic loss to property and food supply. Furthermore, animals, such as mammals, fish and birds, are often susceptible to parasite infestation and/or infection. These parasites may be ectoparasites, such as insects and acarine species, and endoparasites such as filariae and other worms. Thus, there is an ongoing need to develop active pesticidal and parasiticidal compounds to protect animals, crops, plants, plant propagation material and property against attack or infestation/infection by pests.

Domesticated animals, such as cats and dogs, are often infested with ectoparasites, including fleas (*Ctenocephalides felis* spp. and the like), ticks (*Rhipicephalus* spp., *Ixodes* spp., *Dermacentor* spp., *Amblyomma* spp. and the like), mites (*Demodex* spp., *Sarcoptes* spp., *Otodectes* spp. and the like), lice (*Trichodectes* spp., *Cheyletiella* spp., *Lignonathus* spp. and the like), mosquitoes (*Aedes* spp., *Culex* spp., *Anopheles* spp. and the like) and flies (*Haematobia* spp., *Musca* spp., *Stomoxys* spp., *Dermatobia* spp., *Coclyomia* spp., *Lucilia* spp. and the like).

Fleas and ticks are a particular problem because not only do they adversely affect the health of the animal or human, but they also cause a great deal of psychological stress and are also vectors of pathogenic agents that cause disease in both animals and humans. For example, fleas may transmit dog tapeworm (*Dipylidium caninum*), while ticks are the vector of pathogenic agents that transmit diseases such as borrelioses (Lyme disease caused by *Borrelia burgdorferi*), babesioses (or piroplasmoses caused by *Babesia* spp.), Ehrlichiosis (caused by *Ehrlichia* spp.) and rickettsioses (also known as Rocky Mountain spotted fever).

Likewise, farm animals are also susceptible to parasite infestations. For example, cattle are affected by a large number of parasites. A parasite which is very prevalent among farm animals is the tick genus *Boophilus*, especially those of the species microplus (cattle tick), *decoloratus* and *annulatus*. Ticks, such as *Boophilus microplus*, are particularly difficult to control because they live in the pasture where the farm animals graze. Other important parasites of cattle and sheep include myiasis-causing flies such as *Dermatobia hominis* (known as Berne in Brazil) and *Cochliomyia hominivorax* (greenbottle); sheep myiasis-causing flies such as *Lucilia sericata*, and *Lucilia cuprina* (known as blowfly strike in Australia, New Zealand and South Africa). Other problematic fly parasites include *Haematobia irritans* (horn fly) and *Stomoxys calcitrans* (stable fly).

Many pesticides exist in the art for treating parasites and other animal pests. These pesticides vary in their effectiveness to a particular parasite as well as their cost. However the results of treatment with these pesticides are not always satisfactory because of, for example, the development of resistance by the parasite to the therapeutic agent, as is the case, for example, with carbamates, organophosphorus compounds and pyrethroids. Thus, there is a need in the art for more effective pesticidal agents for treatment and protection of animals, e.g. mammals, fish and birds, and for protecting crops, growing plants and wood-containing structures from infestation by animal pests.

Organosulfur compounds substituted with haloalkyl groups, particularly with fluoroalkyl groups, that are active against arthropods have been reported. Published Japanese patent application nos. 2007-161617 and 2007-186494 to Sumitomo Chemical Company describe organosulfur compounds substituted with fluoroalkyl groups that are active against arthropods. International Publications nos. WO 2008/143332, WO 2008/143333, WO 2008/143338, WO 209/005110, WO 2009/014268 and WO 209/025397, all to Sumitomo Chemical Company, also describe a series of organosulfur compounds substituted with haloalkyl groups that are reported to be active against harmful arthropods. WO 2007/147888 to BASF Aktiengesellschaft describes malononitrile compounds that may include a sulfur atom that are active against animal pests.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

The invention provides novel bis-organosulfur compounds with parasiticidal and insecticidal activity and compositions comprising the compounds. The invention also provides methods for the treatment and prevention of parasitic infestation and/or infection of animals and for protecting crops, plants, plant propagation material and wood-containing property from pests.

In one embodiment, the present invention provides bis-organosulfur compounds of formula (I) shown below:

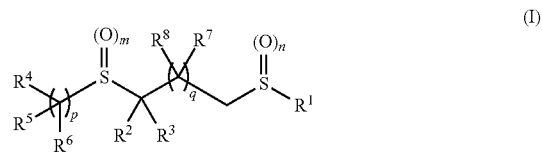

(I)

or a veterinarily or agriculturally acceptable salt thereof, wherein the meanings of variables $R^1$, $R^2$, $R^3$, $R^4$, $R^5$, $R^6$, $R^7$, $R^8$, n, m, p and q are as described below. The invention also provides veterinary and agricultural compositions comprising the inventive compounds, or salts thereof, in combination with a veterinarily or agriculturally acceptable carrier or dilutent.

The inventive compounds and compositions comprising the compounds are highly effective for the treatment or prophylaxis of parasites in or on mammals, fish and birds, and in particular, cats, dogs, horses, chickens, pigs, sheep and cattle with the aim of ridding these hosts of all the parasites commonly encountered by mammals, fish and birds. The invention also provides for effective and long-lasting defense against ectoparasites, such as fleas, ticks, mites, e.g. itch mites, mosquitoes, flies and lice, and of endoparasites, such as filariae, hookworms, whipworms and roundworms of the digestive tract of animals and humans.

The compounds and compositions of the invention are also active against pests that damage agricultural material, and may be effectively used to treat and protect plants, crops, plant propagation material, property containing wood or derived from wood, from harmful animal pests.

Accordingly, the present invention provides methods for preventing and treating parasites in or on animals, comprising administering a parasiticidally effective amount of a compound of formula (I) or (II), or a veterinarily acceptable salt thereof, to the animal. The invention also provides a method for combating or controlling animal pests and for protecting crops, growing plants, plant propagation material, and wood-containing material, or material derived from wood from infestation by pests, comprising contacting the animal pests, plants, plant propagation material, or the soil or water in which the plants is growing, or the wood-containing material or material derived from wood, with a pesticidally effective amount of a compound of formula (I) or (II), or an agriculturally acceptable salt thereof.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law; e.g., they allow for elements not explicitly recited, but exclude elements that are found in the prior art or that affect a basic or novel characteristic of the invention.

These and other embodiments are disclosed or are obvious from, and encompassed by, the following Detailed Description.

DETAILED DESCRIPTION

The present invention provides novel bis-organosulfur compounds with insecticidal and parasiticidal activity, or veterinarily acceptable or agriculturally acceptable salts thereof, and compositions comprising the compounds or salts for the treatment or prevention of parasitic infestations and/or infection in an animal or for the protection of crops, plants, plant propagation material (e.g. seed), or wood-containing property from pests. Also provided are methods for the treatment or prevention of parasitic infestations and/or infection in animals, comprising administering an effective amount of the compound of the invention, or a salt thereof, to the animal. Methods for protecting crops, plants, plant propagation material, or material containing wood or derived from wood, from harmful pests comprising applying an effective amount of the compound of the invention to the crops, plants, plant propagation material, to the soil or water in which they grow, or to the material containing wood or derived from wood, are also provided. An important aspect of the invention is to provide bis-organosulfur compounds with high potency against pests and improved safety to the user and the environment.

The compounds of the formulae (I) and (II) described herein and their veterinarily acceptable or agriculturally acceptable salts are particularly effective for controlling arthropodal pests such as arachnids, myriapods and insects as well as endoparasites. Endoparasites include, but are not limited to, nematodes (such as roundworms, hookworms, whipworms and heartworms) and cestodes (tapeworms) and trematodes (flukes). Ectoparasites that are particularly well controlled by the compounds of the invention include various species of ticks and fleas, mites, lice and flies. Animal pests present a serious problem to the health and wellbeing of many animals, and to crops, plants, plant propagation material, and wood-containing property or property derived from wood, if left uncontrolled. Therefore, the inventive compounds of formulae (I) and (II), veterinarily or agriculturally acceptable salts thereof, and compositions comprising the compounds and salts, have substantial utility in preventing damage to crops, plants, plant propagation material and wood-containing property, and in controlling and preventing the infestation and/or infection of animals by parasites.

The invention includes at least the following features:

(a) In one embodiment, the invention provides novel compounds of formulae (I) and (II), or veterinarily or agriculturally acceptable salts thereof, which are active against animal pests, including insects and parasites;

(b) veterinary and agricultural compositions for combating and controlling pests comprising a pesticidally or parasiticidally effective amount of the compounds of formula (I) or (II), or veterinarily or agriculturally acceptable salts thereof, in combination with a veterinarily or agriculturally acceptable carrier or diluent;

(c) plant propagation material (e.g. seed), comprising at least one compound of formula (I) or (II), or agriculturally acceptable salts thereof (d) veterinary and agricultural compositions for combating pests comprising a pesticidally or parasiticidally effective amount of the compounds of the invention, or veterinarily or agriculturally acceptable salts thereof, in combination with one more other active agent and a veterinarily or agriculturally acceptable carrier or diluent;

(e) methods for treating a parasitic infestation/infection in or on an animal are provided, which methods comprise administering a parasiticidally effective amount of a compound of formula (I) or (II), or veterinarily acceptable salts thereof, to the animal in need thereof;

(f) methods for the prevention of a parasitic infestation/infection of an animal, which comprise administering a parasiticidally effective amount of a compound of formula (I) or (II), or veterinarily acceptable salts thereof, to the animal in need thereof;

(g) methods for combating or controlling pests that are detrimental to crops, plants, plant propagation material, or material containing wood or derived from wood, comprising contacting the crop, plants, plant propagation material, or material containing wood or derived from wood, with a pesticidally effective amount of a compound of formula (I) or (II), or an agriculturally acceptable salt thereof, or a composition comprising the compounds;

(h) methods for combating or controlling pests at a locus, comprising administering a pesticidally or parasiticidally effective amount of a compound of formula (I) or (II), or veterinarily or agriculturally acceptable salts thereof, to the locus;

(i) use of the compounds of formula (I) or (II), or veterinarily or agriculturally acceptable salts thereof, for controlling pests, including parasites, in or on an animal or on crops, plants, plant propagation material, or material containing wood or derived from wood;

(j) use of the compounds of formula (I) or (II), or veterinarily acceptable salts thereof, in the manufacture of a veterinary medicament for controlling pests, including parasites; and (k) processes for the preparation of the compounds of formula (I) or (II).

DEFINITIONS

Terms used herein will have their customary meanings in the art unless specified. The organic moieties mentioned in the definitions of the variables of formula (I) or (II) are like the term halogen—i.e., collective terms for individual listings of the individual group members. The prefix $C_n$-$C_m$ indicates in each case the possible number of carbon atoms in the group.

The term "alkyl" refers to saturated straight, branched, cyclic, primary, secondary or tertiary hydrocarbons, including those having 1 to 12 atoms. In some embodiments, alkyl groups will include $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$ or $C_2$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple fused rings which fused rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Examples of heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

The term "alkylthio" or "alkylsulfanyl" refers to alkyl-S—, where "alkyl" is as defined above. In some embodiments, the alkyl component of the alkylthio group will include $C_r$, $C_{10}$, $C_1$-$C_8$, $C_1$-$C_6$ or $C_1$-$C_4$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —SO—$CH_3$, —SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylfulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above.

The term "alkylsulfonyl" refers to the group alkyl-S(=O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —$SO_2$—$CH_3$, —$SO_2$—$C_2H_5$, n-propylsulfonyl, —$SO_2$—CH($CH_3$)$_2$, n-butylsulfonyl, 1-methylpropylsulfonyl, 2-methylpropylsulfonyl, —$SO_2$—C($CH_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The terms "alkenylfulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$—, and haloalkyl-S(=O)$_2$—, haloalkenyl-S(=O)$_2$—, and haloalkynyl-S(=O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl) amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

The term "trialkylsilyl" refers to the group —Si(alkyl)$_3$, where the group is bonded to the parent compound at the silicon atom.

Compounds of the Invention:

The compounds of the invention are bis-organosulfur compounds comprising one or more halogen atoms, preferably one or more fluorine atoms, which have potent activity against pests, including parasites. In certain embodiments, the compounds of the invention are useful in veterinary applications, including for controlling parasites in or on an animal. In other embodiments, the inventive compounds are useful in agricultural applications for combating or controlling animal pests that damage crops, plants, plant propagation material or material containing wood or derived from wood.

In one embodiment the invention provides a bis-organosulfur compound of formula (I), or a veterinarily or agriculturally acceptable salt thereof:

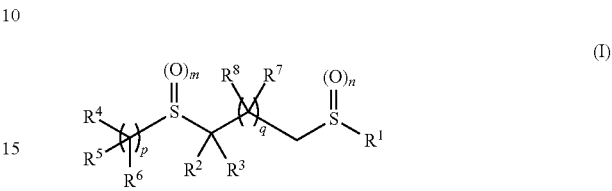

wherein
  n=0, 1, or 2;
  m=0, 1, or 2;
  p=1, 2 or 3;
  q=0, 1, 2, 3 or 4;
  $R^1$ is haloalkyl, haloalkenyl, haloalkynyl; or aryl, aralkyl, heteroaryl, or heterocyclyl each of which is substituted by one or more halogen atoms; all of which may be further substituted by one or more $R^{10}$;
  $R^2$ is halogen, cyano, alkyl, haloalkyl, or —C=(G)-$R^9$
  $R^3$ is hydrogen, halogen, alkyl, or haloalkyl
  $R^4$ is haloalkyl, haloalkenyl, haloalkynyl, or aralkyl, which is substituted by one or more halogen atoms; all of which may be further substituted by one or more $R^{10}$, or
  $R^4$ is aryl or a 3- to 7-membered saturated or partially unsaturated heterocyclic ring which may contain 1 to 3 heteroatoms selected from oxygen, sulfur and nitrogen or a 5- to 6-membered heteroaromatic ring which may contain 1 to 3 heteroatoms selected from oxygen, nitrogen and sulfur,
  wherein aryl, the heterocyclic ring, or the heteroaromatic ring may be fused to another aryl ring or a 5- to 6-membered saturated, partially unsaturated or aromatic heterocyclic ring which may contain 1 to 3 heteroatoms selected from oxygen, nitrogen and sulphur;
  and wherein the aryl, heteroaryl, heterocyclic rings or the respective fused ring systems may be unsubstituted or substituted by any combination of 1 to 6 groups $R^{10}$;
  $R^5$, $R^6$, $R^7$ and $R^8$ are independently from each other hydrogen, halogen, alkyl, or haloalkyl;
  $R^9$ is alkyl, hydroxy, amino, alkoxy, aryloxy, alkylamino, or dialkylamino, the latter four optionally substituted with halogen;
  G is Oxygen or Sulfur; and
  $R^{10}$=halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, halo alkenylsulfonyl, haloalkynylsulfonyl, alkylamino, alkenylamino, alkynylamino, di(alkyl)amino, di(alkenyl)-amino, di(alkynyl) amino, or trialkylsilyl;
  with the proviso that at least one group from $R^2$, $R^3$, $R^4$, $R^5$ and $R^6$ is not hydrogen, alkyl or haloalkyl.

The present invention provides compounds where the sulfur atoms are in various combinations of oxidation states. For example, in one embodiment, the invention provides a compound of formula (I) wherein n is 0 and m is 0. In another embodiment, n is 0 and m is 1. In still another embodiment of formula (I), n is 0 and m is 2.

In another embodiment of formula (I), n is 1 and m is 0. In another embodiment, n is 1 and m is 1. In still another embodiment of formula (I), n is 1 and m is 2.

In yet another embodiment of formula (I), n is 2 and m is 0. In another embodiment, n is 2 and m is 1. In still another embodiment, n is 2 and m is 2.

In another embodiment of formula (I), n is 0, m is 2, and q is 1 or 2.

In a preferred embodiment of formula (I), n is 0, m is 2, and q is 1.

In a preferred embodiment of formula (I), $R^1$ comprises one or more fluorine atoms.

In another preferred embodiment of formula (I), $R^1$ is haloalkyl, haloalkenyl or haloalkynyl, each of which comprises one or more fluorine atoms.

In another embodiment of formula (I), $R^1$ is aryl or aralkyl, each of which are substituted by one or more fluorine atoms or fluoroalkyl groups.

In still another embodiment of formula (I), $R^1$ is heteroaryl or heterocyclyl, each of which are substituted by one or more fluorine atoms or fluoroalkyl groups.

In one embodiment of formula (I), $R^2$ is cyano or —C=(G)-$R^9$.

In one embodiment of formula (I), $R^2$ is —C=(G)-$R^9$, wherein G is oxygen or sulfur; and $R^{9'}$ is $C_1$-$C_6$ alkoxy, amino, $C_1$-$C_6$ alkylamino, or $C_1$-$C_6$ dialkylamino In another embodiment of formula (I), $R^3$ is hydrogen, halogen or $C_1$-$C_6$ alkyl.

In yet another embodiment of formula (I), $R^5$ and $R^6$ are independently hydrogen or halogen.

In another embodiment of formula (I), $R^4$ is haloalkyl.

In still another embodiment, $R^4$ is fluoroalkyl.

In another embodiment $R^4$ is selected from

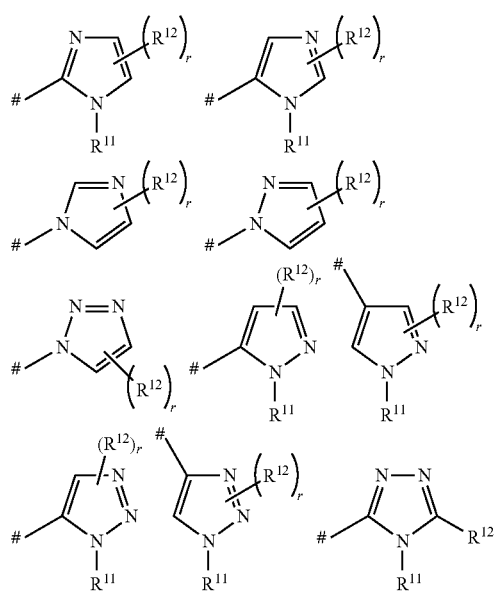

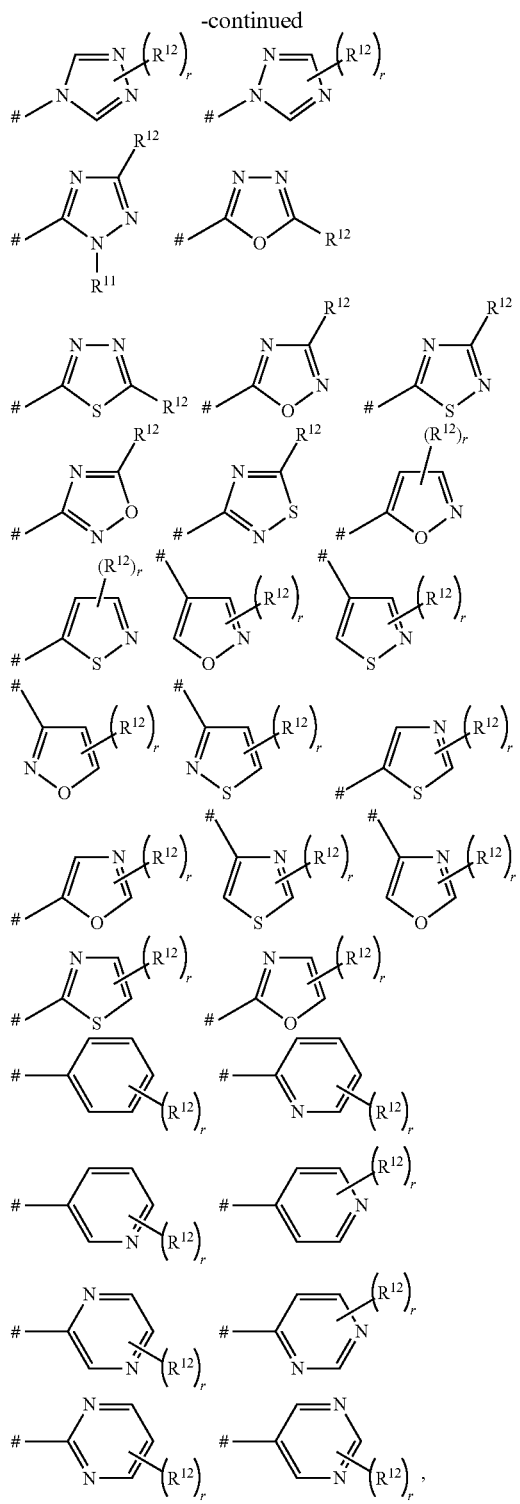

wherein r is 0, 1, 2 or 3, $R^{11}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl, and $R^{12}$ is halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl.

In one embodiment of formula (I), $R^1$ is $C_1$-$C_6$ haloalkyl and $R^2$ is cyano.

In another embodiment of formula (I), $R^1$ is $C_1$-$C_6$ haloalkyl, $R^2$ is cyano, and $R^4$ is haloalkyl.

In yet another embodiment of formula (I), $R^1$ is $C_1$-$C_6$ haloalkyl, $R^2$ is cyano, and $R^4$ is unsubstituted or substituted aryl.

In yet another embodiment of formula (I), $R^1$ is $C_1$-$C_6$ haloalkyl; $R^2$ is cyano, and $R^4$ is an unsubstituted or substituted heterocyclic ring or heteroaryl ring.

In yet another embodiment, the invention provides a compound of formula (I), wherein:
$R^1$ is $C_1$-$C_6$ haloalkyl;
$R^2$ is halogen, cyano or —C=(G)-$R^9$;
$R^3$ is hydrogen, halogen or $C_1$-$C_6$ alkyl;
$R^4$ is $C_1$-$C_6$ haloalkyl, unsubstituted or substituted aryl, or unsubstituted or substituted heteroaryl; and
$R^5$ and $R^6$ are each independently hydrogen or halogen.

In another embodiment, the invention provides a compound of formula (I), wherein:
$R^1$ is $C_1$-$C_6$ haloalkyl;
$R^2$ is cyano or —C=(G)-$R^9$;
$R^3$ is hydrogen, halogen or $C_1$-$C_6$ alkyl;
$R^4$ is $C_1$-$C_6$ haloalkyl;
$R^5$ and $R^6$ are each hydrogen;
$R^7$ and $R^8$ are each independently hydrogen, halogen or alkyl; and
q is 1 or 2.

In still another embodiment, the invention provides a compound of formula (I), wherein:
$R^1$ $C_1$-$C_6$ haloalkyl;
$R^2$ cyano or —C=(G)-$R^9$;
$R^3$ is hydrogen, halogen or $C_1$-$C_6$ alkyl;
$R^4$ is selected from

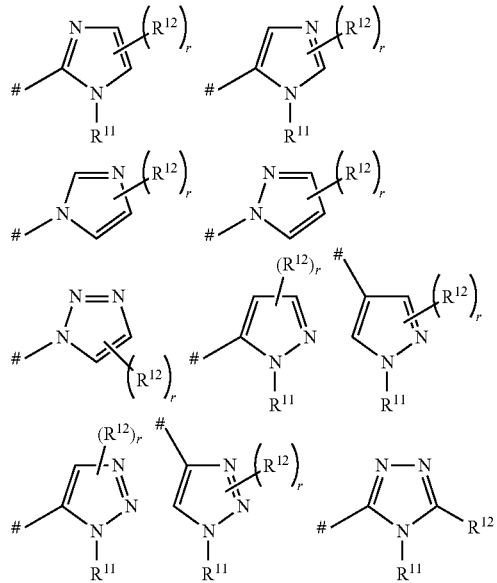

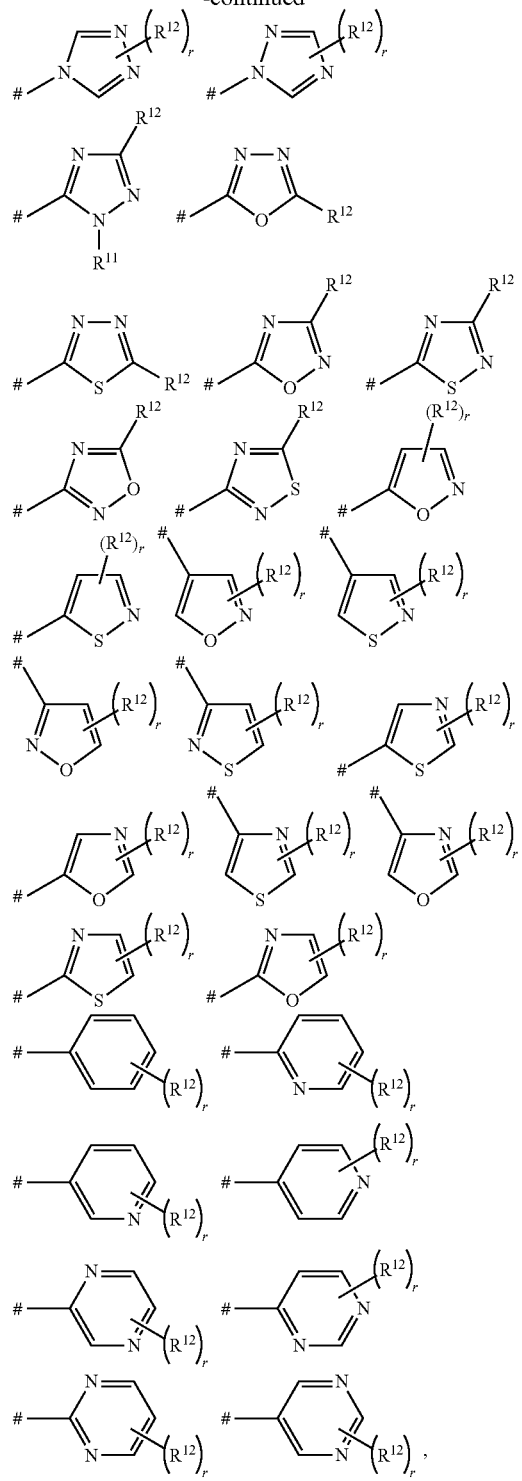

wherein r is 0, 1, 2, 3 or 4,
$R^{11}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl, and
$R^{12}$ is halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;

$R^5$ and $R^6$ are each hydrogen;

$R^7$ and $R^8$ are each independently hydrogen, halogen or alkyl; and q is 1 or 2.

In another embodiment, the invention provides a compound of formula (I), wherein:

$R^1$ is $C_1$-$C_6$ haloalkyl;

$R^2$ is cyano or —C=(G)-$R^9$;

$R^3$ is hydrogen, halogen or $C_1$-$C_6$ alkyl;

$R^4$ is haloalkenyl or haloalkynyl;

$R^5$ and $R^6$ are each hydrogen;

$R^7$ and $R^8$ are each independently hydrogen, halogen or alkyl; and q is 1 or 2.

In yet another embodiment, the invention provides a compound of formula (I), wherein:

$R^1$ is $C_1$-$C_6$ haloalkyl;

$R^2$ is haloalkyl, cyano or —C=(G)-$R^9$;

$R^3$ is hydrogen, halogen or $C_1$-$C_6$ alkyl;

$R^4$ is $C_1$-$C_6$ haloalkyl, unsubstituted or substituted aryl, or unsubstituted or substituted heteroaryl;

$R^5$ and $R^6$ are each independently hydrogen or halogen;

G is oxygen or sulfur;

$R^7$ and $R^8$ are each independently hydrogen, halogen or alkyl;

$R^9$ is $C_1$-$C_6$ alkyl, $C_1$-$C_6$ alkoxy, amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is $C_1$-$C_6$ haloalkyl;

$R^5$ and $R^6$ are each independently hydrogen or halogen;

G is oxygen;

$R^7$ and $R^8$ are each hydrogen, halogen or alkyl;

$R^9$ is $C_1$-$C_6$ alkyl, $C_1$-$C_6$ alkoxy, amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is $C_1$-$C_6$ haloalkyl;

$R^5$ and $R^6$ are each independently hydrogen or halogen;

G is sulfur;

$R^7$ and $R^8$ are each hydrogen, halogen or alkyl;

$R^9$ is $C_1$-$C_6$ alkyl, amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is unsubstituted or substituted aryl or heteroaryl;

$R^5$ and $R^6$ are each independently hydrogen or halogen;

G is oxygen or sulfur;

$R^7$ and $R^8$ are each independently hydrogen, halogen or alkyl;

$R^9$ is $C_1$-$C_6$ alkyl, $C_1$-$C_6$ alkoxy, amino, $C_1$-$C_6$ alkylamino, or $C_1$-$C_6$ dialkylamino;

m is 1 or 2; and q is 1.

In yet another embodiment, the invention provides a compound of formula (I), wherein:

$R^1$ is $C_1$-$C_6$ haloalkyl;

$R^2$ is hydrogen, haloalkyl, cyano or —C=(G)-$R^9$;

$R^3$ is hydrogen, halogen or $C_1$-$C_6$ alkyl;

$R^4$ is $C_1$-$C_6$ haloalkyl, unsubstituted or substituted aryl, or unsubstituted or substituted heteroaryl;

$R^5$ and $R^6$ are each independently hydrogen or halogen;

$R^7$ and $R^8$ are each independently hydrogen, alkyl or haloalkyl;

G is oxygen or sulfur;

$R^9$ is amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is $C_1$-$C_6$ haloalkyl;

$R^5$ and $R^6$ are each independently hydrogen or halogen;

$R^7$ and $R^8$ are each independently hydrogen, alkyl or haloalkyl;

G is oxygen;

$R^9$ is amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is $C_1$-$C_6$ haloalkyl;

$R^5$ and $R^6$ are each independently hydrogen or halogen;

$R^7$ and $R^8$ are each independently hydrogen, alkyl or haloalkyl;

G is sulfur;

$R^9$ is amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is unsubstituted or substituted aryl or heteroaryl;

$R^5$ and $R^6$ are each independently hydrogen or halogen;

$R^7$ and $R^8$ are each independently hydrogen, alkyl or haloalkyl;

G is oxygen;

$R^9$ is amino, $C_1$-$C_6$ alkylamino, or $C_1$-$C_6$ dialkylamino;

m is 1 or 2; and q is 1.

In another embodiment, the invention provides a compound of formula (I), wherein:

$R^1$ is $C_1$-$C_6$ fluoroalkyl;

$R^2$ is cyano or —C=(G)-$R^9$;

$R^3$ is hydrogen, halogen or $C_1$-$C_6$ alkyl;

$R^4$ is unsubstituted or substituted aryl or heteroaryl;

$R^5$ and $R^6$ are each independently hydrogen or halogen;

$R^7$ and $R^8$ are each independently hydrogen, alkyl or haloalkyl;

G is sulfur;

$R^9$ is amino, $C_1$-$C_6$ alkylamino, or $C_1$-$C_6$ dialkylamino;

m is 1 or 2; and q is 1.

In yet another embodiment, the invention provides a compound of formula (I), wherein:
$R^1$ is $C_1$-$C_6$ fluoroalkyl;
$R^2$ is cyano or —C=(G)-$R^9$;
$R^3$ is hydrogen, halogen or $C_1$-$C_6$ alkyl;
$R^4$ is $C_1$-$C_6$ fluoroalkyl; unsubstituted or substituted phenyl; or unsubstituted or substituted heteroaryl;
$R^5$ and $R^6$ are hydrogen;
$R^7$ and $R^8$ are each independently hydrogen or halogen;
G is sulfur;
$R^9$ is amino;
m is 1 or 2;
q is 1; and
n is 0 or 1.

In another embodiment, the invention provides a compound of formula (I), wherein:
$R^1$ is $C_1$-$C_6$ fluoroalkyl;
$R^2$ is cyano or —C=(G)-$R^9$;
$R^3$ is hydrogen, halogen or $C_1$-$C_6$ alkyl;
$R^4$ is $C_1$-$C_6$ fluoroalkyl;
$R^5$ and $R^6$ are hydrogen;
$R^7$ and $R^8$ are each independently hydrogen or halogen;
G is sulfur;
$R^9$ is amino;
m is 1 or 2;
q is 1; and
n is 0 or 1.

In another embodiment, the invention provides a compound of formula (I), wherein:
$R^1$ is $C_1$-$C_6$ fluoroalkyl;
$R^2$ is cyano or —C=(G)-$R^9$;
$R^3$ is hydrogen, halogen or $C_1$-$C_6$ alkyl;
$R^4$ is phenyl, which may be unsubstituted or substituted with one or more halogen atoms, alkyl or haloalkyl groups;
$R^5$ and $R^6$ are hydrogen;
$R^7$ and $R^8$ are each independently hydrogen or halogen;
G is sulfur;
$R^9$ is amino;
m is 1 or 2;
q is 1; and
n is 0 or 1.

In another embodiment, the invention provides a compound of formula (I), wherein:
$R^1$ is $C_1$-$C_6$ fluoroalkyl;
$R^2$ is cyano or —C=(G)-$R^9$;
$R^3$ is hydrogen, halogen or $C_1$-$C_6$ alkyl;
$R^4$ is selected from

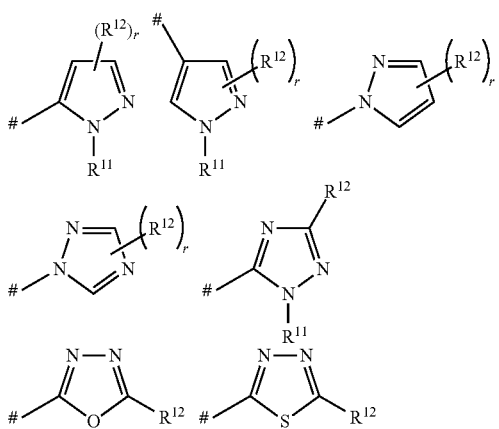

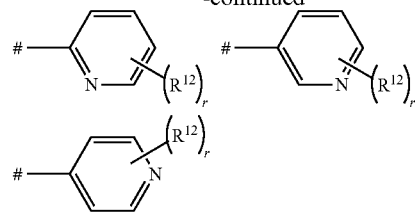

wherein r is 1 or 2,
$R^{11}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl, and
$R^{12}$ is halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;
$R^5$ and $R^6$ are hydrogen;
$R^7$ and $R^8$ are each independently hydrogen or halogen;
G is sulfur;
$R^9$ is amino;
m is 1 or 2;
q is 1; and
n is 0 or 1.

In one embodiment the invention provides a bis-organosulfur compound of formula (II), or a veterinarily or agriculturally acceptable salt thereof:

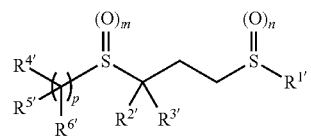

wherein
n=0, 1 or 2;
m=0, 1 or 2;
p=1 or 2;
$R^{1'}$ is $C_1$-$C_6$haloalkyl, $C_2$-$C_6$haloalkenyl, $C_2$-$C_6$haloalkynyl; or aryl, aralkyl, heteroaryl, each of which is substituted by one or more halogen atoms; all of which may be further substituted by one or more substituents;
$R^{2'}$ is cyano, $C_1$-$C_6$-alkyl, $C_1$-$C_6$-haloalkyl, or —C=(G)-$R^{7'}$
$R^{3'}$ is hydrogen, halogen, $C_1$-$C_6$-alkyl, or $C_1$-$C_6$-haloalkyl
$R^{4'}$ is $C_1$-$C_6$-haloalkyl, $C_1$-$C_6$-haloalkenyl, or $C_1$-$C_6$-haloalkynyl, each of which is substituted by one or more halogen atoms, and which may be further substituted by one or more other substituents; or
$R^{4'}$ is aryl or a 3- to 7-membered saturated or partially unsaturated heterocyclic ring which may contain 1 to 3 heteroatoms selected from oxygen, sulfur and nitrogen or a 5- to 6-membered heteroaromatic ring which may contain 1 to 3 heteroatoms selected from oxygen, nitrogen and sulfur, wherein aryl, the heterocyclic ring, or the heteroaromatic ring may be fused to another aryl ring or a 5- to 6-membered saturated, partially unsaturated or aromatic heterocyclic ring which may contain 1 to 3 heteroatoms selected from oxygen, nitrogen and sulphur;

and wherein the aryl, heteroaryl or heterocyclic rings or the respective fused ring systems may be unsubstituted or substituted by any combination of 1 to $6R^{8'}$ groups;

$R^{5'}$ and $R^{6'}$ are independently from each other hydrogen, halogen, $C_1$-$C_6$-alkyl, or $C_1$-$C_6$-haloalkyl;

$R^{7'}$ is $C_1$-$C_6$alkyl, hydroxy, amino, $C_1$-$C_6$-alkoxy, $C_1$-$C_6$-alkylamino, or $C_1$-$C_6$-dialkylamino, the latter three optionally substituted with halogen;

G is Oxygen or Sulfur; and $R^{8'}$=halogen, cyano, nitro, hydroxy, mercapto, amino, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-haloalkyl, $C_2$-$C_6$-haloalkenyl, $C_2$-$C_6$-haloalkynyl, $C_3$-$C_6$-halocycloalkyl, $C_3$-$C_6$-halocycloalkenyl, $C_1$-$C_6$-alkoxy, $C_2$-$C_6$-alkenyloxy, $C_2$-$C_6$-alkynyloxy, $C_1$-$C_6$-haloalkoxy, $C_2$-$C_6$-haloalkenyloxy, $C_2$-$C_6$-haloalkynyloxy, $C_3$-$C_6$-cycloalkoxy, $C_3$-$C_6$-cycloalkenyloxy, $C_3$-$C_6$-halocycloalkoxy, $C_3$-$C_6$-halocycloalkenyloxy, $C_1$-$C_6$-alkylthio, $C_1$-$C_6$-haloalkylthio, $C_3$-$C_6$-cycloalkylthio, $C_3$-$C_6$-halocycloalkylthio, $C_1$-$C_6$-alkylsulfinyl, $C_2$-$C_6$-alkenylsulfinyl, $C_2$-$C_6$-alkynyl-sulfinyl, $C_1$-$C_6$-haloalkylsulfinyl, $C_2$-$C_6$-haloalkenylsulfinyl, $C_2$-$C_6$-haloalkynylsulfinyl, $C_1$-$C_6$-alkylsulfonyl, $C_2$-$C_6$-alkenylsulfonyl, $C_2$-$C_6$-alkynylsulfonyl, $C_1$-$C_6$-haloalkyl-sulfonyl, $C_2$-$C_6$-haloalkenylsulfonyl, $C_2$-$C_6$-haloalkynylsulfonyl, $C_1$-$C_6$-alkylamino, $C_2$-$C_6$-alkenylamino, $C_2$-$C_6$-alkynylamino, $C_1$-$C_6$-di(alkyl)amino, di($C_2$-$C_6$-alkenyl)-amino, di($C_2$-$C_6$-alkynyl)amino, or tri($C_1$-$C_{10}$)alkylsilyl;

with the proviso that at least one group from $R^{2'}$, $R^{3'}$, $R^{4'}$, $R^{5'}$ and $R^{6'}$ is not hydrogen, alkyl or haloalkyl.

The sulfur atoms in the compound of formula (II) may be in various combinations of oxidation states. For example, in one embodiment, the invention provides a compound of formula (II) wherein n is 0 and m is 0. In another embodiment, n is 0 and m is 1. In still another embodiment of formula (II), n is 0 and m is 2.

In another embodiment of formula (II), n is 1 and m is 0. In another embodiment, n is 1 and m is 1. In still another embodiment of formula (II), n is 1 and m is 2.

In yet another embodiment of formula (II), n is 2 and m is 0. In another embodiment, n is 2 and m is 1. In still another embodiment, n is 2 and m is 2.

In another embodiment of formula (II), m is 2, n is 0, and p is 1.

In a preferred embodiment of formula (II), $R^{1'}$ comprises one or more fluorine atoms.

In another preferred embodiment of formula (II), $R^{1'}$ is haloalkyl, haloalkenyl or haloalkynyl, each of which comprises one or more fluorine atoms.

In a preferred embodiment of formula (II), $R^{1'}$ is $C_1$-$C_6$-haloalkyl.

In a preferred embodiment of formula (II), $R^{1'}$ is $C_1$-$C_6$-fluoroalkyl.

In another embodiment of formula (II), $R^{1'}$ is aryl or aralkyl, which are substituted by one or more halogen atoms or haloalkyl groups.

In a preferred embodiment of formula (II), $R^{1'}$ is aryl or aralkyl, which are substituted by one or more fluorine atoms or fluoroalkyl groups.

In still another embodiment of formula (II), $R^{1'}$ is heteroaryl or heterocyclyl, which are substituted by one or more halogen atoms or haloalkyl groups.

In still another embodiment of formula (II), $R^{1'}$ is heteroaryl or heterocyclyl, which are substituted by one or more fluorine atoms or fluoroalkyl groups.

In one embodiment of formula (II), $R^{2'}$ is cyano or —C=(G)-$R^{7'}$.

In one embodiment of formula (II), $R^{2'}$ is —C=(G)-$R^{7'}$, wherein G is oxygen or sulfur, and $R^{7'}$ is $C_1$-$C_6$-alkyl, amino, $C_1$-$C_6$ alkylamino, or $C_1$-$C_6$ dialkylamino In another embodiment of formula (II), $R^{3'}$ is hydrogen, halogen or $C_1$-$C_6$ alkyl.

In yet another embodiment of formula (II), $R^{5'}$ and $R^{6'}$ are independently hydrogen or halogen.

In another embodiment of formula (II), $R^{4'}$ is haloalkyl.

In still another embodiment, $R^{4'}$ is fluoroalkyl.

In still another embodiment, $R^{4'}$ is phenyl, substituted with one or more halogen atoms, alkyl groups or haloalkyl groups.

In still another embodiment, $R^{4'}$ is phenyl, substituted with one or more fluorine atoms or fluoroalkyl groups.

In still another embodiment, $R^{4'}$ is selected from

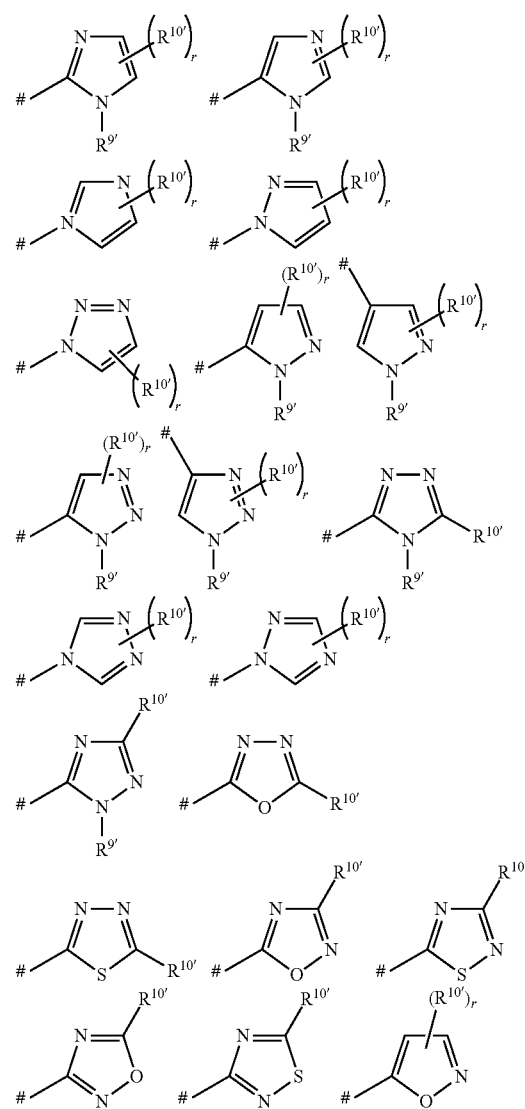

-continued

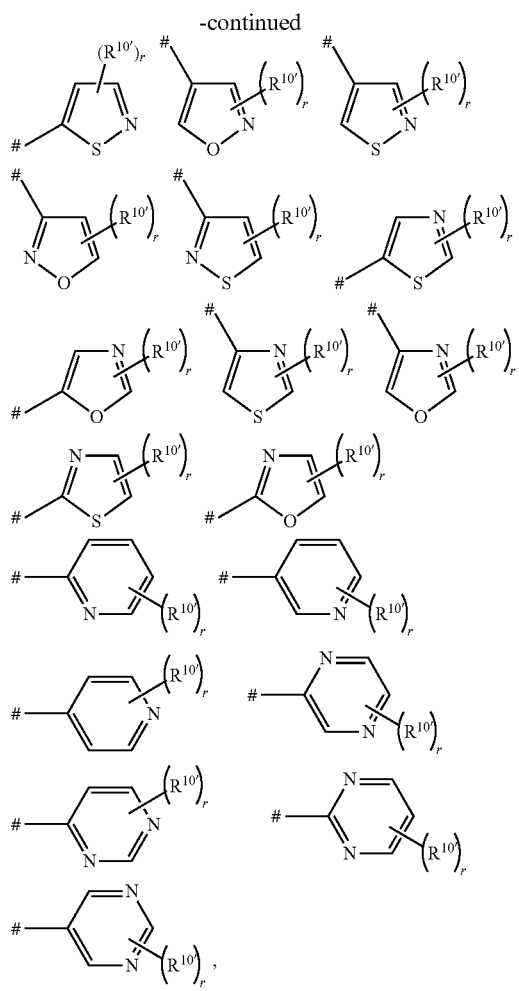

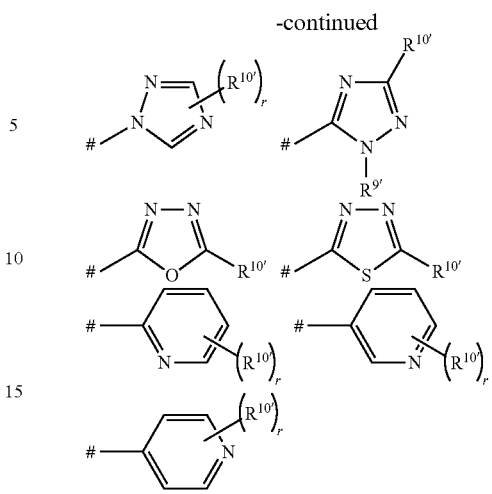

wherein r is 0, 1, 2 or 3

$R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_z$—$C_6$ haloalkenyl, or $C_3$-$C_6$ halocycloalkenyl and $R^{10'}$ is halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl.

In still another embodiment, $R^{4'}$ is selected from

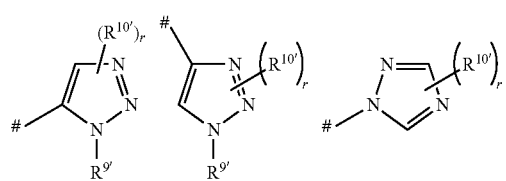

wherein r is 1 or 2

$R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl and $R^{10'}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl.

In a preferred embodiment, when $R^{4'}$ is selected from one of the heteroaryls listed above, $R^{9'}$ is selected from hydrogen, $C_1$-$C_6$ alkyl, or $C_1$-$C_6$ haloalkyl, and $R^{10'}$ is selected from halogen, $C_1$-$C_6$ alkyl, $C_1$-$C_6$ haloalkyl, $C_2$-$C_6$ alkenyl or $C_2$-$C_6$ haloalkenyl.

In another embodiment, the invention provides a compound of formula (II) wherein:
$R^{1'}$ is $C_1$-$C_6$-fluoroalkyl;
$R^{2'}$ is cyano or —C=(G)-$R^{7'}$;
$R^{3'}$ is hydrogen, halogen or $C_1$-$C_6$-alkyl;
$R^{4'}$ is $C_1$-$C_6$ haloalkyl; unsubstituted or substituted phenyl; or unsubstituted or substituted heteroaryl;
$R^{5'}$ and $R^{6'}$ are hydrogen;
G is oxygen;
$R^{7'}$ is $C_1$-$C_6$ alkyl, $C_1$-$C_6$ alkoxy, amino, $C_1$-$C_6$ alkylamino, or $C_1$-$C_6$ dialkylamino; and
n is 0 or 1.

In another embodiment, the invention provides a compound of formula (II) wherein:
$R^{1'}$ is $C_1$-$C_6$-fluoroalkyl;
$R^{2'}$ is cyano or —C=(G)-$R^{7'}$;
$R^{3'}$ is hydrogen, halogen or $C_1$-$C_6$-alkyl;
$R^{4'}$ is $C_1$-$C_6$-haloalkyl; unsubstituted or substituted phenyl or unsubstituted or substituted heteroaryl;
$R^{5'}$ and $R^6$ are hydrogen;
G is sulfur;
$R^{7'}$ is $C_1$-$C_6$-alkyl, amino, $C_1$-$C_6$ alkylamino, or $C_1$-$C_6$ dialkylamino and
n is 0 or 1.

In another embodiment, the invention provides a compound of formula (II), wherein:

R$^{1'}$ is C$_1$-C$_6$-fluoroalkyl;
R$^{2'}$ is cyano or —C=(G)-R$^{7'}$;
R$^{3'}$ is hydrogen, halogen or C$_1$-C$_6$-alkyl;
R$^{4'}$ is C$_1$-C$_6$-haloalkyl;
R$^{5'}$ and R$^{6'}$ are hydrogen;
G is oxygen;
R$^{7'}$ is C$_1$-C$_6$-alkyl, C$_1$-C$_6$-alkoxy, amino, C$_1$-C$_6$ alkylamino, or C$_1$-C$_6$ dialkylamino; and
n is 0 or 1.

In another embodiment, the invention provides a compound of formula (II), wherein:
R$^{1'}$ is C$_1$-C$_6$-fluoroalkyl;
R$^{2'}$ is cyano or —C=(G)-R$^{7'}$;
R$^{3'}$ is hydrogen, halogen or C$_1$-C$_6$-alkyl;
R$^{4'}$ is C$_1$-C$_6$-haloalkyl;
R$^{5'}$ and R$^{6'}$ are hydrogen;
G is sulfur;
R$^{7'}$ is C$_1$-C$_6$-alkyl, amino, C$_1$-C$_6$ alkylamino, or C$_1$-C$_6$ dialkylamino; and
n is 0 or 1.

In another embodiment, the invention provides a compound of formula (II), wherein:
R$^{1'}$ is C$_1$-C$_6$-fluoroalkyl;
R$^{2'}$ is cyano or —C=(G)-R$^{7'}$;
R$^{3'}$ is hydrogen, halogen or C$_1$-C$_6$-alkyl;
R$^{4'}$ is phenyl, which may be unsubstituted or substituted with one or more halogen atoms, alkyl or haloalkyl groups;
R$^{5'}$ and R$^{6'}$ are hydrogen;
G is oxygen;
R$^{7'}$ is C$_1$-C$_6$-alkyl, C$_1$-C$_6$-alkoxy, amino, C$_1$-C$_6$ alkylamino, or C$_1$-C$_6$ dialkylamino; and
n is 1 or 2.

In another embodiment, the invention provides a compound of formula (II), wherein:
R$^{1'}$ is C$_1$-C$_6$-fluoroalkyl;
R$^{2'}$ is cyano or —C=(G)-R$^{7'}$;
R$^{3'}$ is hydrogen, halogen or C$_1$-C$_6$-alkyl;
R$^{4'}$ is phenyl, which may be unsubstituted or substituted with one or more halogen atoms, alkyl or haloalkyl groups;
R$^{5'}$ and R$^{6'}$ are hydrogen;
G is sulfur;
R$^{7'}$ is C$_1$-C$_6$-alkyl, amino, C$_1$-C$_6$ alkylamino, or C$_1$-C$_6$ dialkylamino; and
n is 1 or 2.

In another embodiment, the invention provides a compound of formula (II), wherein:
R$^{1'}$ is C$_1$-C$_6$-fluoroalkyl;
R$^{2'}$ is cyano or —C=(G)-R$^{7'}$;
R$^{3'}$ is hydrogen, halogen or C$_1$-C$_6$-alkyl;
R$^{4'}$ is selected from

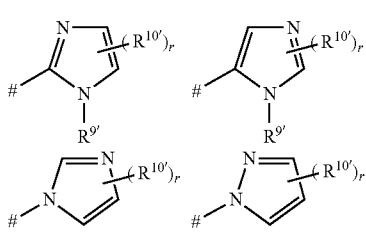

-continued

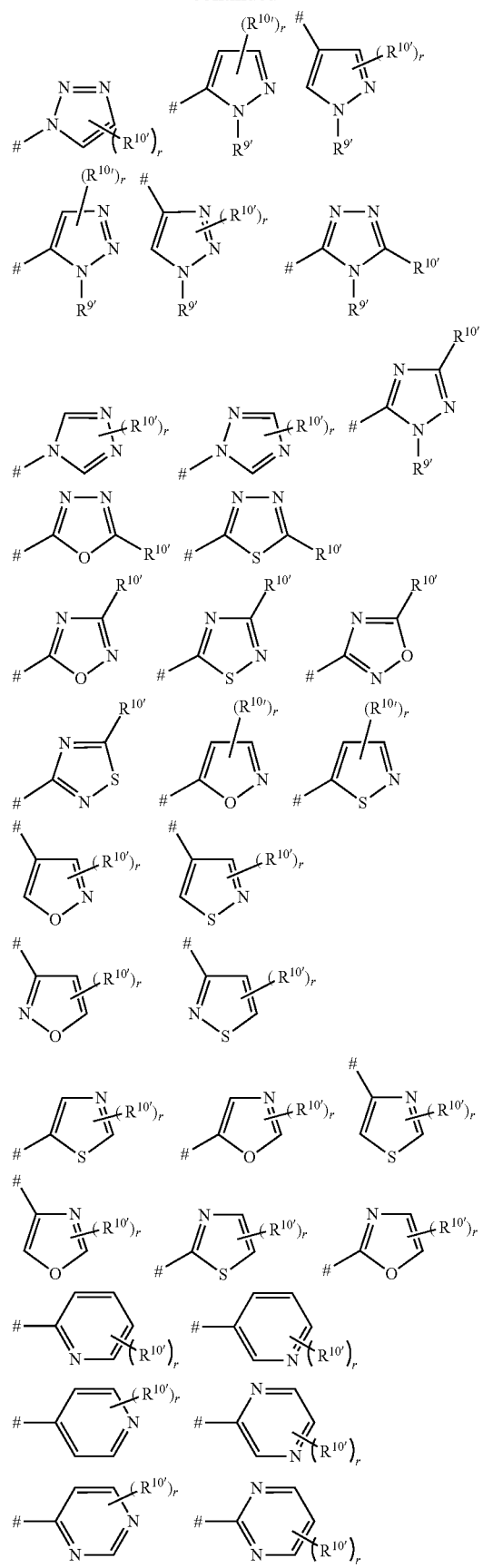

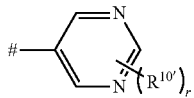

wherein r is 0, 1, 2 or 3, $R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl which may be substituted with one or more substituents and $R^{10'}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;

$R^{5'}$ and $R^6$ are hydrogen;

G is oxygen;

$R^{7'}$ is $C_1$-$C_6$-alkyl, $C_1$-$C_6$-alkoxy, amino, $C_1$-$C_6$ alkylamino, or $C_1$-$C_6$ dialkylamino; and n is 0 or 1.

In another embodiment, the invention provides a compound of formula (II), wherein:

$R^{1'}$ is $C_1$-$C_6$-fluoroalkyl;

$R^{2'}$ is cyano or —C=(G)-$R^{7'}$;

$R^{3'}$ is hydrogen, halogen or $C_1$-$C_6$-alkyl;

$R^{4'}$ is selected from

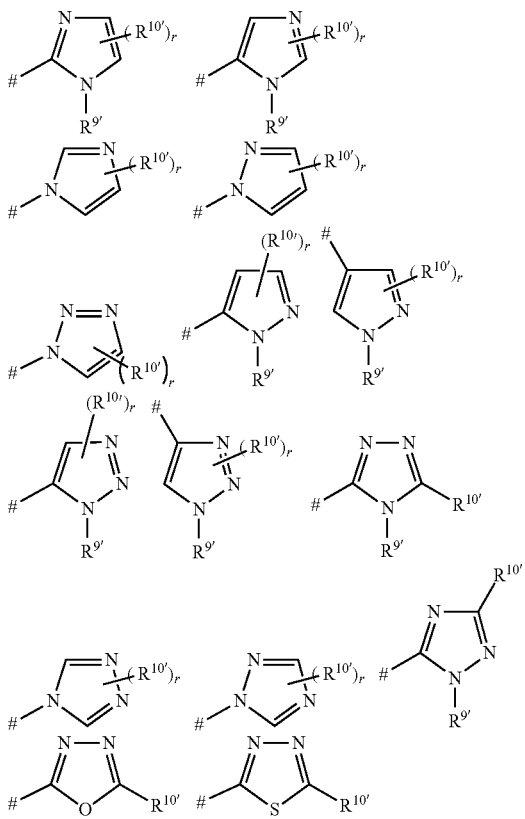

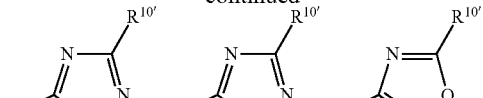

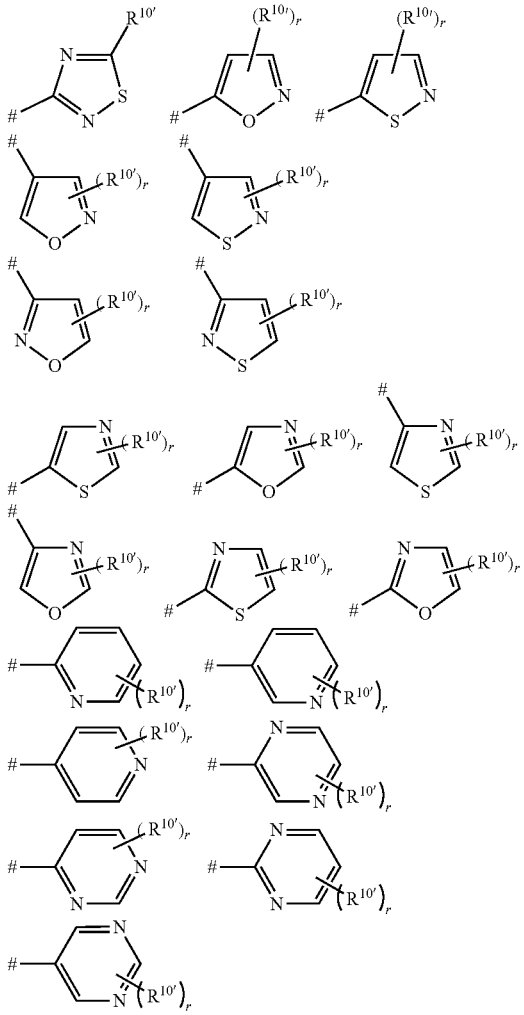

wherein r is 0, 1, 2 or 3, $R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl which may be substituted with one or more substituents and $R^{10'}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;

$R^{5'}$ and $R^6$ are hydrogen;

G is sulfur;

$R^{7'}$ is $C_1$-$C_6$-alkyl, amino, $C_1$-$C_6$ alkylamino, or $C_1$-$C_6$ dialkylamino; and n is 0 or 1.

In another embodiment, the invention provides a compound of formula (II) wherein:
$R^{1'}$ is $C_1$-$C_6$-fluoroalkyl;
$R^{2'}$ is cyano;
$R^{3'}$ is hydrogen, methyl or ethyl;
$R^{4'}$ is $C_1$-$C_6$-haloalkyl; unsubstituted or substituted phenyl; or unsubstituted or substituted heteroaryl;
$R^{5'}$ and $R^{6'}$ are hydrogen; and
n is 0 or 1.

In another embodiment, the invention provides a compound of formula (II), wherein:
$R^{1'}$ is $C_1$-$C_6$-fluoroalkyl;
$R^{2'}$ is cyano;
$R^{3'}$ is hydrogen, methyl or ethyl;
$R^{4'}$ is $C_1$-$C_6$-haloalkyl;
$R^{5'}$ and $R^{6'}$ are hydrogen; and
n is 0 or 1.

In another embodiment, the invention provides a compound of formula (II), wherein:
$R^{1'}$ is $C_1$-$C_6$-fluoroalkyl;
$R^{2'}$ is cyano;
$R^{3'}$ is hydrogen, methyl or ethyl;
$R^{4'}$ is phenyl, which may be unsubstituted or substituted with one or more halogen atoms, alkyl or haloalkyl groups;
$R^{5'}$ and $R^{6'}$ are hydrogen; and
n is 0 or 1.

In another embodiment, the invention provides a compound of formula (II), wherein:
$R^{1'}$ is $C_1$-$C_6$-fluoroalkyl;
$R^{2'}$ is cyano;
$R^{3'}$ is hydrogen, methyl or ethyl;
$R^{4'}$ is selected from

[structures of heteroaryl groups: pyrazoles, triazoles, oxadiazoles, thiadiazole, pyridines with $R^{10'}$ and $R^{9'}$ substituents]

wherein r is 1 or 2,
$R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl which may be substituted with one or more substituents and
$R^{10'}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;
$R^{5'}$ and $R^{6'}$ are hydrogen; and
n is 0 or 1.

Tables A, B, C, D, E and F below provide preferred compounds of formula (II) according to the present invention.

1. Formula II-A

Amongst compounds of the formula (II), preference is given to the following compounds of the formula II-A:

$$R^{4'} \diagdown S(O)_2 \diagdown C(R^{2'})(R^{3'}) \diagdown CH_2CH_2 \diagdown S \diagdown R^{1'} \quad \text{(II-A)}$$

wherein the variables $R^{1'}$, $R^{2'}$, $R^{3'}$ and $R^{4'}$ have the meanings given below in Table A.

The definition of the variables in each line of the table represents an example of a compounds according to the present invention (Compounds II-A.1 to II-A.675).

TABLE A

| Number of compound | $R^1$ | $R^2$ | $R^3$ | $R^4$ |
|---|---|---|---|---|
| II-A.1 | $CF_3$ | CN | H | $CF_2CF_3$ |
| II-A.2 | $CF_3$ | CN | H | $CF_2CF_2CF_3$ |
| II-A.3 | $CF_3$ | CN | H | $CF_2CF_2CF_2H$ |
| II-A.4 | $CF_3$ | CN | H | $CH_2CF_2CF_3$ |
| II-A.5 | $CF_3$ | CN | H | $CH_2CF_2CF_2H$ |
| II-A.6 | $CF_3$ | CN | H | #—⟨phenyl⟩—Cl (4-Cl) |
| II-A.7 | $CF_3$ | CN | H | #—⟨phenyl⟩(3,4-diCl) |
| II-A.8 | $CF_3$ | CN | H | #—⟨phenyl⟩—$CF_3$ (4-$CF_3$) |
| II-A.9 | $CF_3$ | CN | H | #—⟨phenyl⟩—$OCF_3$ (4-$OCF_3$) |
| II-A.10 | $CF_3$ | CN | H | #—⟨pyridyl⟩—$CF_3$ |
| II-A.11 | $CF_3$ | CN | H | #—⟨pyridyl⟩—$CF_3$ |
| II-A.12 | $CF_3$ | CN | H | #—⟨pyrazolyl⟩—$CF_3$ |

TABLE A-continued

| Number of compound | R¹ | R² | R³ | R⁴ |
|---|---|---|---|---|
| II-A.13 | CF₃ | CN | H | 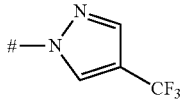 |
| II-A.14 | CF₃ | CN | H | 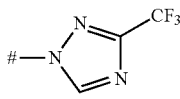 |
| II-A.15 | CF₃ | CN | H | 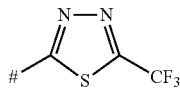 |
| II-A.16 | CF₂H | CN | H | CF₂CF₃ |
| II-A.17 | CF₂H | CN | H | CF₂CF₂CF₃ |
| II-A.18 | CF₂H | CN | H | CF₂CF₂CF₂H |
| II-A.19 | CF₂H | CN | H | CH₂CF₂CF₃ |
| II-A.20 | CF₂H | CN | H | CH₂CF₂CF₂H |
| II-A.21 | CF₂H | CN | H |  |
| II-A.22 | CF₂H | CN | H | 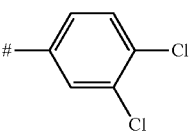 |
| II-A.23 | CF₂H | CN | H | 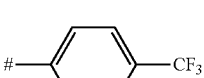 |
| II-A.24 | CF₂H | CN | H |  |
| II-A.25 | CF₂H | CN | H |  |
| II-A.26 | CF₂H | CN | H | 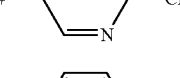 |
| II-A.27 | CF₂H | CN | H | 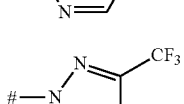 |
| II-A.28 | CF₂H | CN | H | 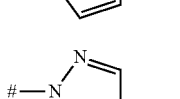 |
| II-A.29 | CF₂H | CN | H | 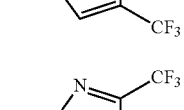 |
| II-A.30 | CF₂H | CN | H | 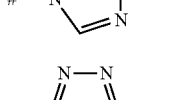 |
| II-A.31 | CF₂CF₃ | CN | H | CF₂CF₃ |
| II-A.32 | CF₂CF₃ | CN | H | CF₂CF₂CF₃ |
| II-A.33 | CF₂CF₃ | CN | H | CF₂CF₂CF₂H |
| II-A.34 | CF₂CF₃ | CN | H | CH₂CF₂CF₃ |
| II-A.35 | CF₂CF₃ | CN | H | CH₂CF₂CF₂H |
| II-A.36 | CF₂CF₃ | CN | H | 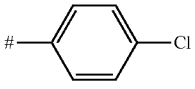 |
| II-A.37 | CF₂CF₃ | CN | H | 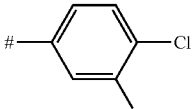 |
| II-A.38 | CF₂CF₃ | CN | H | 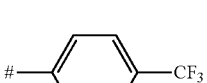 |
| II-A.39 | CF₂CF₃ | CN | H | 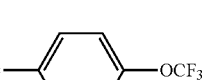 |
| II-A.40 | CF₂CF₃ | CN | H | 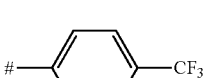 |
| II-A.41 | CF₂CF₃ | CN | H | 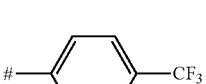 |
| II-A.42 | CF₂CF₃ | CN | H | 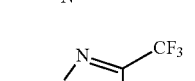 |
| II-A.43 | CF₂CF₃ | CN | H | 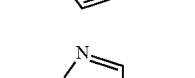 |
| II-A.44 | CF₂CF₃ | CN | H | 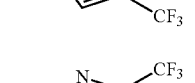 |
| II-A.45 | CF₂CF₃ | CN | H | 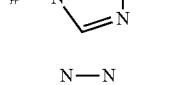 |
| II-A.46 | CF₃ | C(O)CH₃ | H | CF₂CF₃ |
| II-A.47 | CF₃ | C(O)CH₃ | H | CF₂CF₂CF₃ |
| II-A.48 | CF₃ | C(O)CH₃ | H | CF₂CF₂CF₂H |
| II-A.49 | CF₃ | C(O)CH₃ | H | CH₂CF₂CF₃ |
| II-A.50 | CF₃ | C(O)CH₃ | H | CH₂CF₂CF₂H |
| II-A.51 | CF₃ | C(O)CH₃ | H |  |

TABLE A-continued

| Number of compound | R¹ | R² | R³ | R⁴ |
|---|---|---|---|---|
| II-A.52 | CF₃ | C(O)CH₃ | H | 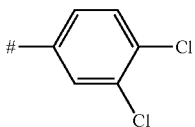 |
| II-A.53 | CF₃ | C(O)CH₃ | H | 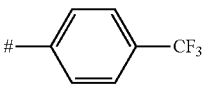 |
| II-A.54 | CF₃ | C(O)CH₃ | H | 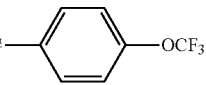 |
| II-A.55 | CF₃ | C(O)CH₃ | H | 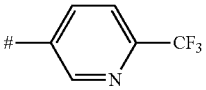 |
| II-A.56 | CF₃ | C(O)CH₃ | H | 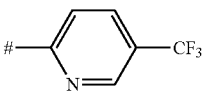 |
| II-A.57 | CF₃ | C(O)CH₃ | H | 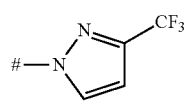 |
| II-A.58 | CF₃ | C(O)CH₃ | H | 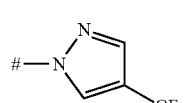 |
| II-A.59 | CF₃ | C(O)CH₃ | H | 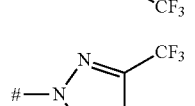 |
| II-A.60 | CF₃ | C(O)CH₃ | H | 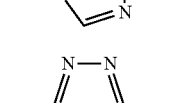 |
| II-A.61 | CF₂H | C(O)CH₃ | H | CF₂CF₃ |
| II-A.62 | CF₂H | C(O)CH₃ | H | CF₂CF₂CF₃ |
| II-A.63 | CF₂H | C(O)CH₃ | H | CF₂CF₂CF₂H |
| II-A.64 | CF₂H | C(O)CH₃ | H | CH₂CF₂CF₃ |
| II-A.65 | CF₂H | C(O)CH₃ | H | CH₂CF₂CF₂H |
| II-A.66 | CF₂H | C(O)CH₃ | H | 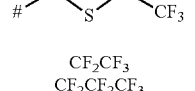 |
| II-A.67 | CF₂H | C(O)CH₃ | H | 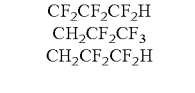 |
| II-A.68 | CF₂H | C(O)CH₃ | H | 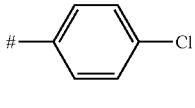 |
| II-A.69 | CF₂H | C(O)CH₃ | H | 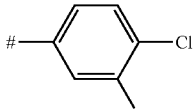 |
| II-A.70 | CF₂H | C(O)CH₃ | H | 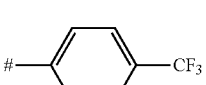 |
| II-A.71 | CF₂H | C(O)CH₃ | H | 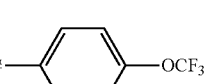 |
| II-A.72 | CF₂H | C(O)CH₃ | H |  |
| II-A.73 | CF₂H | C(O)CH₃ | H |  |
| II-A.74 | CF₂H | C(O)CH₃ | H | 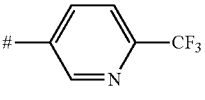 |
| II-A.75 | CF₂H | C(O)CH₃ | H | 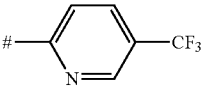 |
| II-A.76 | CF₂CF₃ | C(O)CH₃ | H | CF₂CF₃ |
| II-A.77 | CF₂CF₃ | C(O)CH₃ | H | CF₂CF₂CF₃ |
| II-A.78 | CF₂CF₃ | C(O)CH₃ | H | CF₂CF₂CF₂H |
| II-A.79 | CF₂CF₃ | C(O)CH₃ | H | CH₂CF₂CF₃ |
| II-A.80 | CF₂CF₃ | C(O)CH₃ | H | CH₂CF₂CF₂H |
| II-A.81 | CF₂CF₃ | C(O)CH₃ | H | 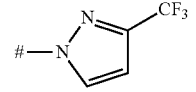 |
| II-A.82 | CF₂CF₃ | C(O)CH₃ | H | 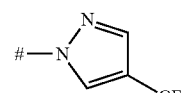 |
| II-A.83 | CF₂CF₃ | C(O)CH₃ | H | 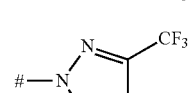 |
| II-A.84 | CF₂CF₃ | C(O)CH₃ | H | 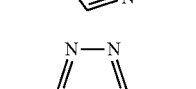 |
| II-A.85 | CF₂CF₃ | C(O)CH₃ | H | 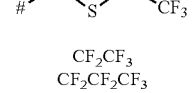 |
| II-A.86 | CF₂CF₃ | C(O)CH₃ | H | 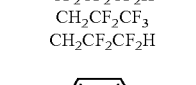 |
| II-A.87 | CF₂CF₃ | C(O)CH₃ | H | 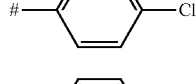 |

TABLE A-continued

| Number of compound | R¹ | R² | R³ | R⁴ |
|---|---|---|---|---|
| II-A.88 | CF₂CF₃ | C(O)CH₃ | H | 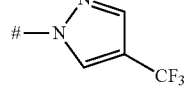 |
| II-A.89 | CF₂CF₃ | C(O)CH₃ | H | 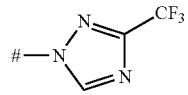 |
| II-A.90 | CF₂CF₃ | C(O)CH₃ | H | 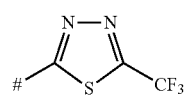 |
| II-A.91 | CF₃ | C(S)NH₂ | H | CF₂CF₃ |
| II-A.92 | CF₃ | C(S)NH₂ | H | CF₂CF₂CF₃ |
| II-A.93 | CF₃ | C(S)NH₂ | H | CF₂CF₂CF₂H |
| II-A.94 | CF₃ | C(S)NH₂ | H | CH₂CF₂CF₃ |
| II-A.95 | CF₃ | C(S)NH₂ | H | CH₂CF₂CF₂H |
| II-A.96 | CF₃ | C(S)NH₂ | H | 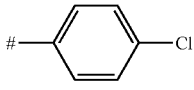 |
| II-A.97 | CF₃ | C(S)NH₂ | H | 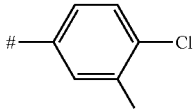 |
| II-A.98 | CF₃ | C(S)NH₂ | H |  |
| II-A.99 | CF₃ | C(S)NH₂ | H | 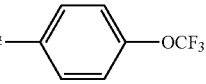 |
| II-A.100 | CF₃ | C(S)NH₂ | H | 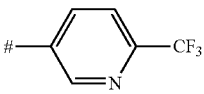 |
| II-A.101 | CF₃ | C(S)NH₂ | H | 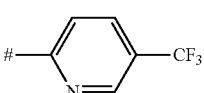 |
| II-A.102 | CF₃ | C(S)NH₂ | H | 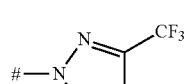 |
| II-A.103 | CF₃ | C(S)NH₂ | H | 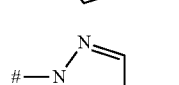 |
| II-A.104 | CF₃ | C(S)NH₂ | H | 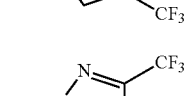 |
| II-A.105 | CF₃ | C(S)NH₂ | H | 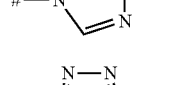 |
| II-A.106 | CF₂H | C(S)NH₂ | H | CF₂CF₃ |
| II-A.107 | CF₂H | C(S)NH₂ | H | CF₂CF₂CF₃ |
| II-A.108 | CF₂H | C(S)NH₂ | H | CF₂CF₂CF₂H |
| II-A.109 | CF₂H | C(S)NH₂ | H | CH₂CF₂CF₃ |
| II-A.110 | CF₂H | C(S)NH₂ | H | CH₂CF₂CF₂H |
| II-A.111 | CF₂H | C(S)NH₂ | H |  |
| II-A.112 | CF₂H | C(S)NH₂ | H | 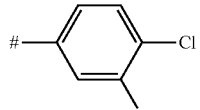 |
| II-A.113 | CF₂H | C(S)NH₂ | H | 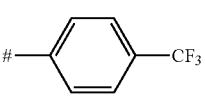 |
| II-A.114 | CF₂H | C(S)NH₂ | H | 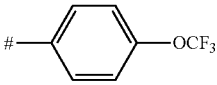 |
| II-A.115 | CF₂H | C(S)NH₂ | H | 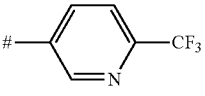 |
| II-A.116 | CF₂H | C(S)NH₂ | H | 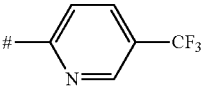 |
| II-A.117 | CF₂H | C(S)NH₂ | H | 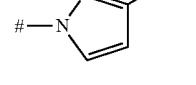 |
| II-A.118 | CF₂H | C(S)NH₂ | H | 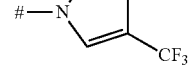 |
| II-A.119 | CF₂H | C(S)NH₂ | H | 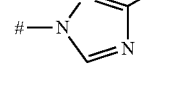 |
| II-A.120 | CF₂H | C(S)NH₂ | H | 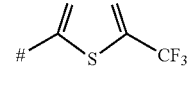 |
| II-A.121 | CF₂CF₃ | C(S)NH₂ | H | CF₂CF₃ |
| II-A.122 | CF₂CF₃ | C(S)NH₂ | H | CF₂CF₂CF₃ |
| II-A.123 | CF₂CF₃ | C(S)NH₂ | H | CF₂CF₂CF₂H |
| II-A.124 | CF₂CF₃ | C(S)NH₂ | H | CH₂CF₂CF₃ |
| II-A.125 | CF₂CF₃ | C(S)NH₂ | H | CH₂CF₂CF₂H |
| II-A.126 | CF₂CF₃ | C(S)NH₂ | H | 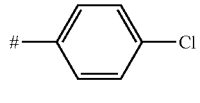 |

TABLE A-continued

| Number of compound | R¹ | R² | R³ | R⁴ |
|---|---|---|---|---|
| II-A.127 | CF₂CF₃ | C(S)NH₂ | H | 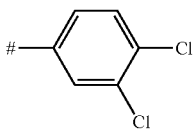 |
| II-A.128 | CF₂CF₃ | C(S)NH₂ | H | 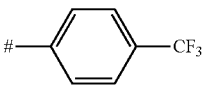 |
| II-A.129 | CF₂CF₃ | C(S)NH₂ | H | 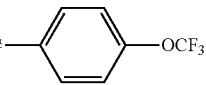 |
| II-A.130 | CF₂CF₃ | C(S)NH₂ | H | 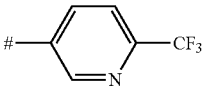 |
| II-A.131 | CF₂CF₃ | C(S)NH₂ | H | 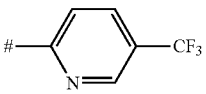 |
| II-A.132 | CF₂CF₃ | C(S)NH₂ | H | 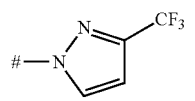 |
| II-A.133 | CF₂CF₃ | C(S)NH₂ | H | 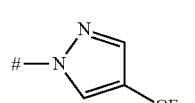 |
| II-A.134 | CF₂CF₃ | C(S)NH₂ | H | 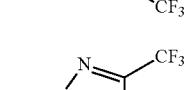 |
| II-A.135 | CF₂CF₃ | C(S)NH₂ | H | 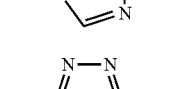 |
| II-A.136 | CF₃ | C(O)NHCH₃ | H | CF₂CF₃ |
| II-A.137 | CF₃ | C(O)NHCH₃ | H | CF₂CF₂CF₃ |
| II-A.138 | CF₃ | C(O)NHCH₃ | H | CF₂CF₂CF₂H |
| II-A.139 | CF₃ | C(O)NHCH₃ | H | CH₂CF₂CF₃ |
| II-A.140 | CF₃ | C(O)NHCH₃ | H | CH₂CF₂CF₂H |
| II-A.141 | CF₃ | C(O)NHCH₃ | H |  |
| II-A.142 | CF₃ | C(O)NHCH₃ | H | 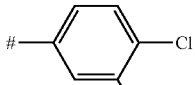 |
| II-A.143 | CF₃ | C(O)NHCH₃ | H | 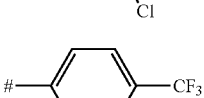 |
| II-A.144 | CF₃ | C(O)NHCH₃ | H |  |
| II-A.145 | CF₃ | C(O)NHCH₃ | H | 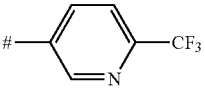 |
| II-A.146 | CF₃ | C(O)NHCH₃ | H | 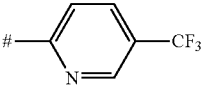 |
| II-A.147 | CF₃ | C(O)NHCH₃ | H | 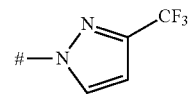 |
| II-A.148 | CF₃ | C(O)NHCH₃ | H | 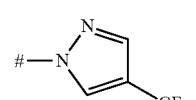 |
| II-A.149 | CF₃ | C(O)NHCH₃ | H | 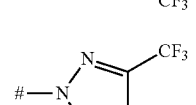 |
| II-A.150 | CF₃ | C(O)NHCH₃ | H | 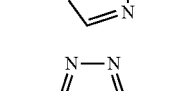 |
| II-A.151 | CF₂H | C(O)NHCH₃ | H | CF₂CF₃ |
| II-A.152 | CF₂H | C(O)NHCH₃ | H | CF₂CF₂CF₃ |
| II-A.153 | CF₂H | C(O)NHCH₃ | H | CF₂CF₂CF₂H |
| II-A.154 | CF₂H | C(O)NHCH₃ | H | CH₂CF₂CF₃ |
| II-A.155 | CF₂H | C(O)NHCH₃ | H | CH₂CF₂CF₂H |
| II-A.156 | CF₂H | C(O)NHCH₃ | H |  |
| II-A.157 | CF₂H | C(O)NHCH₃ | H | 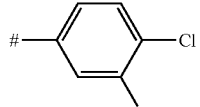 |
| II-A.158 | CF₂H | C(O)NHCH₃ | H | 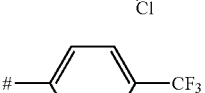 |
| II-A.159 | CF₂H | C(O)NHCH₃ | H |  |
| II-A.160 | CF₂H | C(O)NHCH₃ | H |  |
| II-A.161 | CF₂H | C(O)NHCH₃ | H | 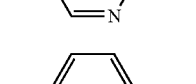 |
| II-A.162 | CF₂H | C(O)NHCH₃ | H | 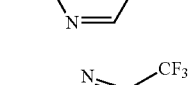 |

TABLE A-continued

| Number of compound | R¹ | R² | R³ | R⁴ |
|---|---|---|---|---|
| II-A.163 | $CF_2H$ | $C(O)NHCH_3$ | H | 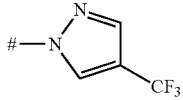 |
| II-A.164 | $CF_2H$ | $C(O)NHCH_3$ | H | 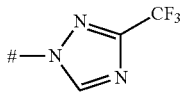 |
| II-A.165 | $CF_2H$ | $C(O)NHCH_3$ | H | 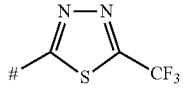 |
| II-A.166 | $CF_2CF_3$ | $C(O)NHCH_3$ | H | $CF_2CF_3$ |
| II-A.167 | $CF_2CF_3$ | $C(O)NHCH_3$ | H | $CF_2CF_2CF_3$ |
| II-A.168 | $CF_2CF_3$ | $C(O)NHCH_3$ | H | $CF_2CF_2CF_2H$ |
| II-A.169 | $CF_2CF_3$ | $C(O)NHCH_3$ | H | $CH_2CF_2CF_3$ |
| II-A.170 | $CF_2CF_3$ | $C(O)NHCH_3$ | H | $CH_2CF_2CF_2H$ |
| II-A.171 | $CF_2CF_3$ | $C(O)NHCH_3$ | H | 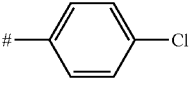 |
| II-A.172 | $CF_2CF_3$ | $C(O)NHCH_3$ | H | 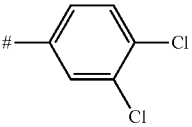 |
| II-A.173 | $CF_2CF_3$ | $C(O)NHCH_3$ | H | 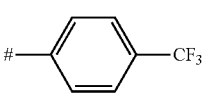 |
| II-A.174 | $CF_2CF_3$ | $C(O)NHCH_3$ | H | 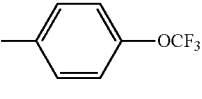 |
| II-A.175 | $CF_2CF_3$ | $C(O)NHCH_3$ | H | 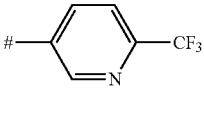 |
| II-A.176 | $CF_2CF_3$ | $C(O)NHCH_3$ | H | 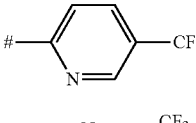 |
| II-A.177 | $CF_2CF_3$ | $C(O)NHCH_3$ | H | 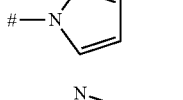 |
| II-A.178 | $CF_2CF_3$ | $C(O)NHCH_3$ | H | 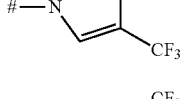 |
| II-A.179 | $CF_2CF_3$ | $C(O)NHCH_3$ | H | 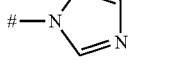 |
| II-A.180 | $CF_2CF_3$ | $C(O)NHCH_3$ | H | 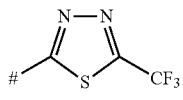 |
| II-A.181 | $CF_3$ | $C(O)N(CH_3)_2$ | H | $CF_2CF_3$ |
| II-A.182 | $CF_3$ | $C(O)N(CH_3)_2$ | H | $CF_2CF_2CF_3$ |
| II-A.183 | $CF_3$ | $C(O)N(CH_3)_2$ | H | $CF_2CF_2CF_2H$ |
| II-A.184 | $CF_3$ | $C(O)N(CH_3)_2$ | H | $CH_2CF_2CF_3$ |
| II-A.185 | $CF_3$ | $C(O)N(CH_3)_2$ | H | $CH_2CF_2CF_2H$ |
| II-A.186 | $CF_3$ | $C(O)N(CH_3)_2$ | H | 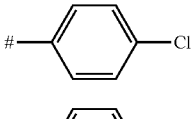 |
| II-A.187 | $CF_3$ | $C(O)N(CH_3)_2$ | H | 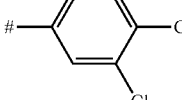 |
| II-A.188 | $CF_3$ | $C(O)N(CH_3)_2$ | H |  |
| II-A.189 | $CF_3$ | $C(O)N(CH_3)_2$ | H | 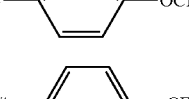 |
| II-A.190 | $CF_3$ | $C(O)N(CH_3)_2$ | H | 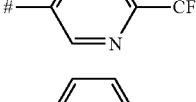 |
| II-A.191 | $CF_3$ | $C(O)N(CH_3)_2$ | H | 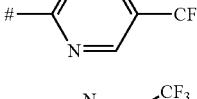 |
| II-A.192 | $CF_3$ | $C(O)N(CH_3)_2$ | H | 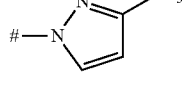 |
| II-A.193 | $CF_3$ | $C(O)N(CH_3)_2$ | H | 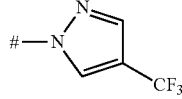 |
| II-A.194 | $CF_3$ | $C(O)N(CH_3)_2$ | H | 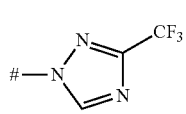 |
| II-A.195 | $CF_3$ | $C(O)N(CH_3)_2$ | H | 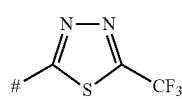 |
| II-A.196 | $CF_2H$ | $C(O)N(CH_3)_2$ | H | $CF_2CF_3$ |
| II-A.197 | $CF_2H$ | $C(O)N(CH_3)_2$ | H | $CF_2CF_2CF_3$ |
| II-A.198 | $CF_2H$ | $C(O)N(CH_3)_2$ | H | $CF_2CF_2CF_2H$ |
| II-A.199 | $CF_2H$ | $C(O)N(CH_3)_2$ | H | $CH_2CF_2CF_3$ |
| II-A.200 | $CF_2H$ | $C(O)N(CH_3)_2$ | H | $CH_2CF_2CF_2H$ |
| II-A.201 | $CF_2H$ | $C(O)N(CH_3)_2$ | H | 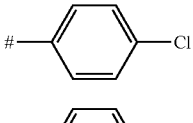 |
| II-A.202 | $CF_2H$ | $C(O)N(CH_3)_2$ | H | 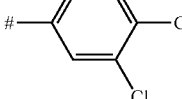 |

TABLE A-continued

| Number of compound | R¹ | R² | R³ | R⁴ |
|---|---|---|---|---|
| II-A.203 | CF₂H | C(O)N(CH₃)₂ | H |  |
| II-A.204 | CF₂H | C(O)N(CH₃)₂ | H | 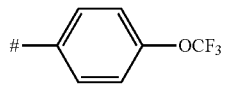 |
| II-A.205 | CF₂H | C(O)N(CH₃)₂ | H | 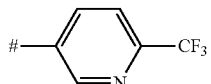 |
| II-A.206 | CF₂H | C(O)N(CH₃)₂ | H | 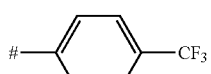 |
| II-A.207 | CF₂H | C(O)N(CH₃)₂ | H | 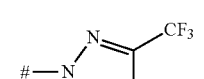 |
| II-A.208 | CF₂H | C(O)N(CH₃)₂ | H | 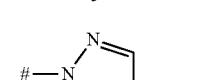 |
| II-A.209 | CF₂H | C(O)N(CH₃)₂ | H | 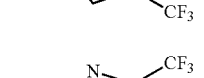 |
| II-A.210 | CF₂H | C(O)N(CH₃)₂ | H | 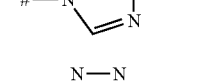 |
| II-A.211 | CF₂CF₃ | C(O)N(CH₃)₂ | H | CF₂CF₃ |
| II-A.212 | CF₂CF₃ | C(O)N(CH₃)₂ | H | CF₂CF₂CF₃ |
| II-A.213 | CF₂CF₃ | C(O)N(CH₃)₂ | H | CF₂CF₂CF₂H |
| II-A.214 | CF₂CF₃ | C(O)N(CH₃)₂ | H | CH₂CF₂CF₃ |
| II-A.215 | CF₂CF₃ | C(O)N(CH₃)₂ | H | CH₂CF₂CF₂H |
| II-A.216 | CF₂CF₃ | C(O)N(CH₃)₂ | H | 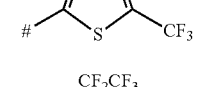 |
| II-A.217 | CF₂CF₃ | C(O)N(CH₃)₂ | H | 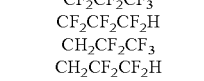 |
| II-A.218 | CF₂CF₃ | C(O)N(CH₃)₂ | H | 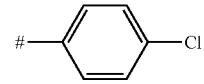 |
| II-A.219 | CF₂CF₃ | C(O)N(CH₃)₂ | H | 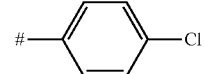 |
| II-A.220 | CF₂CF₃ | C(O)N(CH₃)₂ | H | 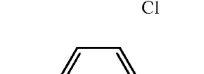 |
| II-A.221 | CF₂CF₃ | C(O)N(CH₃)₂ | H | 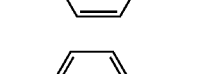 |
| II-A.222 | CF₂CF₃ | C(O)N(CH₃)₂ | H | 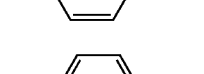 |
| II-A.223 | CF₂CF₃ | C(O)N(CH₃)₂ | H | 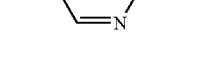 |
| II-A.224 | CF₂CF₃ | C(O)N(CH₃)₂ | H |  |
| II-A.225 | CF₂CF₃ | C(O)N(CH₃)₂ | H | 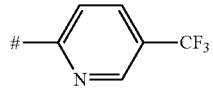 |
| II-A.226 | CF₃ | CN | Cl | CF₂CF₃ |
| II-A.227 | CF₃ | CN | Cl | CF₂CF₂CF₃ |
| II-A.228 | CF₃ | CN | Cl | CF₂CF₂CF₂H |
| II-A.229 | CF₃ | CN | Cl | CH₂CF₂CF₃ |
| II-A.230 | CF₃ | CN | Cl | CH₂CF₂CF₂H |
| II-A.231 | CF₃ | CN | Cl | 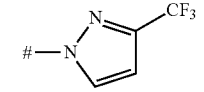 |
| II-A.232 | CF₃ | CN | Cl | 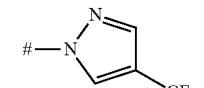 |
| II-A.233 | CF₃ | CN | Cl | 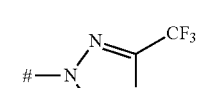 |
| II-A.234 | CF₃ | CN | Cl | 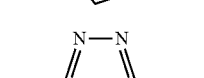 |
| II-A.235 | CF₃ | CN | Cl | 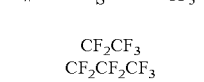 |
| II-A.236 | CF₃ | CN | Cl | 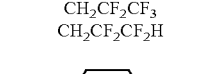 |
| II-A.237 | CF₃ | CN | Cl | 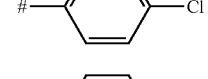 |
| II-A.238 | CF₃ | CN | Cl | 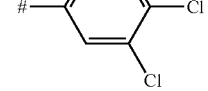 |

TABLE A-continued

| Number of compound | R¹ | R² | R³ | R⁴ |
|---|---|---|---|---|
| II-A.239 | CF₃ | CN | Cl | 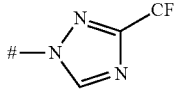 |
| II-A.240 | CF₃ | CN | Cl | 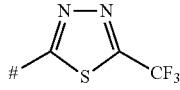 |
| II-A.241 | CF₂H | CN | Cl | CF₂CF₃ |
| II-A.242 | CF₂H | CN | Cl | CF₂CF₂CF₃ |
| II-A.243 | CF₂H | CN | Cl | CF₂CF₂CF₂H |
| II-A.244 | CF₂H | CN | Cl | CH₂CF₂CF₃ |
| II-A.245 | CF₂H | CN | Cl | CH₂CF₂CF₂H |
| II-A.246 | CF₂H | CN | Cl |  |
| II-A.247 | CF₂H | CN | Cl | 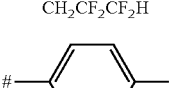 |
| II-A.248 | CF₂H | CN | Cl | 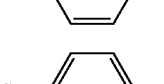 |
| II-A.249 | CF₂H | CN | Cl | 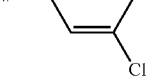 |
| II-A.250 | CF₂H | CN | Cl | 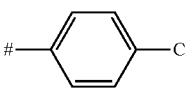 |
| II-A.251 | CF₂H | CN | Cl | 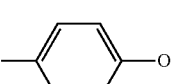 |
| II-A.252 | CF₂H | CN | Cl | 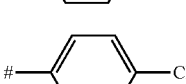 |
| II-A.253 | CF₂H | CN | Cl | 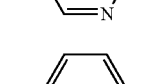 |
| II-A.254 | CF₂H | CN | Cl | 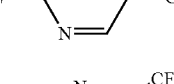 |
| II-A.255 | CF₂H | CN | Cl | 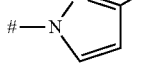 |
| II-A.256 | CF₂CF₃ | CN | Cl | CF₂CF₃ |
| II-A.257 | CF₂CF₃ | CN | Cl | CF₂CF₂CF₃ |
| II-A.258 | CF₂CF₃ | CN | Cl | CF₂CF₂CF₂H |
| II-A.259 | CF₂CF₃ | CN | Cl | CH₂CF₂CF₃ |
| II-A.260 | CF₂CF₃ | CN | Cl | CH₂CF₂CF₂H |
| II-A.261 | CF₂CF₃ | CN | Cl | 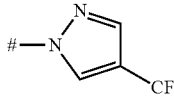 |
| II-A.262 | CF₂CF₃ | CN | Cl | 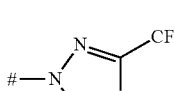 |
| II-A.263 | CF₂CF₃ | CN | Cl | 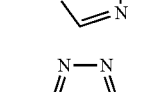 |
| II-A.264 | CF₂CF₃ | CN | Cl | 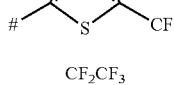 |
| II-A.265 | CF₂CF₃ | CN | Cl | 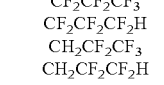 |
| II-A.266 | CF₂CF₃ | CN | Cl |  |
| II-A.267 | CF₂CF₃ | CN | Cl |  |
| II-A.268 | CF₂CF₃ | CN | Cl | 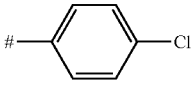 |
| II-A.269 | CF₂CF₃ | CN | Cl | 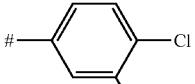 |
| II-A.270 | CF₂CF₃ | CN | Cl | 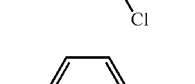 |
| II-A.271 | CF₃ | C(O)CH₃ | Cl | CF₂CF₃ |
| II-A.272 | CF₃ | C(O)CH₃ | Cl | CF₂CF₂CF₃ |
| II-A.273 | CF₃ | C(O)CH₃ | Cl | CF₂CF₂CF₂H |
| II-A.274 | CF₃ | C(O)CH₃ | Cl | CH₂CF₂CF₃ |
| II-A.275 | CF₃ | C(O)CH₃ | Cl | CH₂CF₂CF₂H |
| II-A.276 | CF₃ | C(O)CH₃ | Cl | 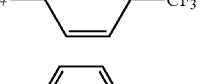 |
| II-A.277 | CF₃ | C(O)CH₃ | Cl | 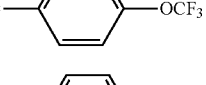 |
| II-A.278 | CF₃ | C(O)CH₃ | Cl | 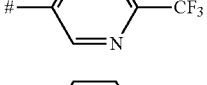 |

TABLE A-continued

| Number of compound | R¹ | R² | R³ | R⁴ |
|---|---|---|---|---|
| II-A.279 | CF₃ | C(O)CH₃ | Cl | #—⟨C₆H₄⟩—OCF₃ (4-OCF₃-phenyl) |
| II-A.280 | CF₃ | C(O)CH₃ | Cl | #—(5-pyridyl)—CF₃ (2-CF₃) |
| II-A.281 | CF₃ | C(O)CH₃ | Cl | #—(2-pyridyl)—CF₃ (5-CF₃) |
| II-A.282 | CF₃ | C(O)CH₃ | Cl | #—N-pyrazolyl-3-CF₃ |
| II-A.283 | CF₃ | C(O)CH₃ | Cl | #—N-pyrazolyl-4-CF₃ |
| II-A.284 | CF₃ | C(O)CH₃ | Cl | #—N-1,2,4-triazolyl-3-CF₃ |
| II-A.285 | CF₃ | C(O)CH₃ | Cl | #—(1,3,4-thiadiazol-2-yl)-5-CF₃ |
| II-A.286 | CF₂H | C(O)CH₃ | Cl | CF₂CF₃ |
| II-A.287 | CF₂H | C(O)CH₃ | Cl | CF₂CF₂CF₃ |
| II-A.288 | CF₂H | C(O)CH₃ | Cl | CF₂CF₂CF₂H |
| II-A.289 | CF₂H | C(O)CH₃ | Cl | CH₂CF₂CF₃ |
| II-A.290 | CF₂H | C(O)CH₃ | Cl | CH₂CF₂CF₂H |
| II-A.291 | CF₂H | C(O)CH₃ | Cl | #—⟨C₆H₄⟩—Cl (4-Cl-phenyl) |
| II-A.292 | CF₂H | C(O)CH₃ | Cl | #—⟨C₆H₃⟩(Cl)(Cl) (3,4-diCl-phenyl) |
| II-A.293 | CF₂H | C(O)CH₃ | Cl | #—⟨C₆H₄⟩—CF₃ (4-CF₃-phenyl) |
| II-A.294 | CF₂H | C(O)CH₃ | Cl | #—⟨C₆H₄⟩—OCF₃ (4-OCF₃-phenyl) |
| II-A.295 | CF₂H | C(O)CH₃ | Cl | #—(5-pyridyl)—CF₃ (2-CF₃) |
| II-A.296 | CF₂H | C(O)CH₃ | Cl | #—(2-pyridyl)—CF₃ (5-CF₃) |
| II-A.297 | CF₂H | C(O)CH₃ | Cl | #—N-pyrazolyl-3-CF₃ |
| II-A.298 | CF₂H | C(O)CH₃ | Cl | #—N-pyrazolyl-4-CF₃ |
| II-A.299 | CF₂H | C(O)CH₃ | Cl | #—N-1,2,4-triazolyl-3-CF₃ |
| II-A.300 | CF₂H | C(O)CH₃ | Cl | #—(1,3,4-thiadiazol-2-yl)-5-CF₃ |
| II-A.301 | CF₂CF₃ | C(O)CH₃ | Cl | CF₂CF₃ |
| II-A.302 | CF₂CF₃ | C(O)CH₃ | Cl | CF₂CF₂CF₃ |
| II-A.303 | CF₂CF₃ | C(O)CH₃ | Cl | CF₂CF₂CF₂H |
| II-A.304 | CF₂CF₃ | C(O)CH₃ | Cl | CH₂CF₂CF₃ |
| II-A.305 | CF₂CF₃ | C(O)CH₃ | Cl | CH₂CF₂CF₂H |
| II-A.306 | CF₂CF₃ | C(O)CH₃ | Cl | #—⟨C₆H₄⟩—Cl (4-Cl-phenyl) |
| II-A.307 | CF₂CF₃ | C(O)CH₃ | Cl | #—⟨C₆H₃⟩(Cl)(Cl) (3,4-diCl-phenyl) |
| II-A.308 | CF₂CF₃ | C(O)CH₃ | Cl | #—⟨C₆H₄⟩—CF₃ (4-CF₃-phenyl) |
| II-A.309 | CF₂CF₃ | C(O)CH₃ | Cl | #—⟨C₆H₄⟩—OCF₃ (4-OCF₃-phenyl) |
| II-A.310 | CF₂CF₃ | C(O)CH₃ | Cl | #—(5-pyridyl)—CF₃ (2-CF₃) |
| II-A.311 | CF₂CF₃ | C(O)CH₃ | Cl | #—(2-pyridyl)—CF₃ (5-CF₃) |
| II-A.312 | CF₂CF₃ | C(O)CH₃ | Cl | #—N-pyrazolyl-3-CF₃ |
| II-A.313 | CF₂CF₃ | C(O)CH₃ | Cl | #—N-pyrazolyl-4-CF₃ |
| II-A.314 | CF₂CF₃ | C(O)CH₃ | Cl | #—N-1,2,4-triazolyl-3-CF₃ |

TABLE A-continued

| Number of compound | R¹ | R² | R³ | R⁴ |
|---|---|---|---|---|
| II-A.315 | $CF_2CF_3$ | $C(O)CH_3$ | Cl | 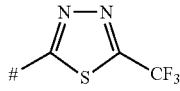 |
| II-A.316 | $CF_3$ | $C(S)NH_2$ | Cl | $CF_2CF_3$ |
| II-A.317 | $CF_3$ | $C(S)NH_2$ | Cl | $CF_2CF_2CF_3$ |
| II-A.318 | $CF_3$ | $C(S)NH_2$ | Cl | $CF_2CF_2CF_2H$ |
| II-A.319 | $CF_3$ | $C(S)NH_2$ | Cl | $CH_2CF_2CF_3$ |
| II-A.320 | $CF_3$ | $C(S)NH_2$ | Cl | $CH_2CF_2CF_2H$ |
| II-A.321 | $CF_3$ | $C(S)NH_2$ | Cl |  |
| II-A.322 | $CF_3$ | $C(S)NH_2$ | Cl | 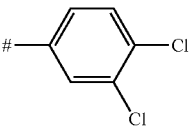 |
| II-A.323 | $CF_3$ | $C(S)NH_2$ | Cl |  |
| II-A.324 | $CF_3$ | $C(S)NH_2$ | Cl | 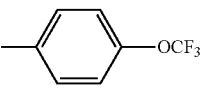 |
| II-A.325 | $CF_3$ | $C(S)NH_2$ | Cl |  |
| II-A.326 | $CF_3$ | $C(S)NH_2$ | Cl | 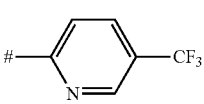 |
| II-A.327 | $CF_3$ | $C(S)NH_2$ | Cl | 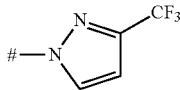 |
| II-A.328 | $CF_3$ | $C(S)NH_2$ | Cl | 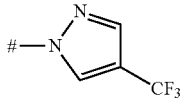 |
| II-A.329 | $CF_3$ | $C(S)NH_2$ | Cl | 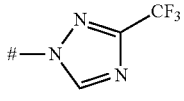 |
| II-A.330 | $CF_3$ | $C(S)NH_2$ | Cl | 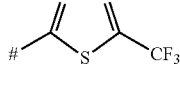 |
| II-A.331 | $CF_2H$ | $C(S)NH_2$ | Cl | $CF_2CF_3$ |
| II-A.332 | $CF_2H$ | $C(S)NH_2$ | Cl | $CF_2CF_2CF_3$ |
| II-A.333 | $CF_2H$ | $C(S)NH_2$ | Cl | $CF_2CF_2CF_2H$ |
| II-A.334 | $CF_2H$ | $C(S)NH_2$ | Cl | $CH_2CF_2CF_3$ |
| II-A.335 | $CF_2H$ | $C(S)NH_2$ | Cl | $CH_2CF_2CF_2H$ |
| II-A.336 | $CF_2H$ | $C(S)NH_2$ | Cl |  |
| II-A.337 | $CF_2H$ | $C(S)NH_2$ | Cl | 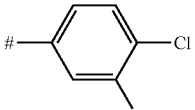 |
| II-A.338 | $CF_2H$ | $C(S)NH_2$ | Cl | 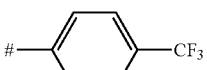 |
| II-A.339 | $CF_2H$ | $C(S)NH_2$ | Cl | 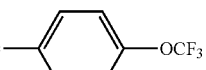 |
| II-A.340 | $CF_2H$ | $C(S)NH_2$ | Cl | 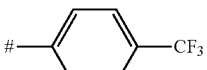 |
| II-A.341 | $CF_2H$ | $C(S)NH_2$ | Cl | 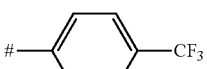 |
| II-A.342 | $CF_2H$ | $C(S)NH_2$ | Cl | 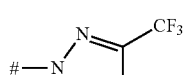 |
| II-A.343 | $CF_2H$ | $C(S)NH_2$ | Cl | 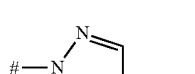 |
| II-A.344 | $CF_2H$ | $C(S)NH_2$ | Cl | 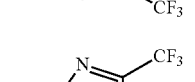 |
| II-A.345 | $CF_2H$ | $C(S)NH_2$ | Cl | 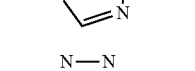 |
| II-A.346 | $CF_2CF_3$ | $C(S)NH_2$ | Cl | $CF_2CF_3$ |
| II-A.347 | $CF_2CF_3$ | $C(S)NH_2$ | Cl | $CF_2CF_2CF_3$ |
| II-A.348 | $CF_2CF_3$ | $C(S)NH_2$ | Cl | $CF_2CF_2CF_2H$ |
| II-A.349 | $CF_2CF_3$ | $C(S)NH_2$ | Cl | $CH_2CF_2CF_3$ |
| II-A.350 | $CF_2CF_3$ | $C(S)NH_2$ | Cl | $CH_2CF_2CF_2H$ |
| II-A.351 | $CF_2CF_3$ | $C(S)NH_2$ | Cl | 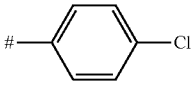 |
| II-A.352 | $CF_2CF_3$ | $C(S)NH_2$ | Cl | 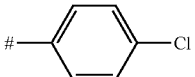 |
| II-A.353 | $CF_2CF_3$ | $C(S)NH_2$ | Cl | 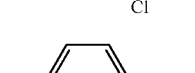 |
| II-A.354 | $CF_2CF_3$ | $C(S)NH_2$ | Cl |  |

TABLE A-continued

| Number of compound | R¹ | R² | R³ | R⁴ |
|---|---|---|---|---|
| II-A.355 | CF₂CF₃ | C(S)NH₂ | Cl | 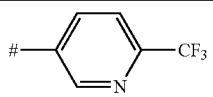 |
| II-A.356 | CF₂CF₃ | C(S)NH₂ | Cl | 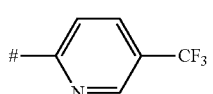 |
| II-A.357 | CF₂CF₃ | C(S)NH₂ | Cl | 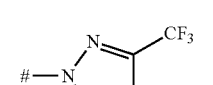 |
| II-A.358 | CF₂CF₃ | C(S)NH₂ | Cl | 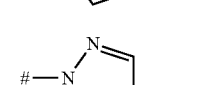 |
| II-A.359 | CF₂CF₃ | C(S)NH₂ | Cl | 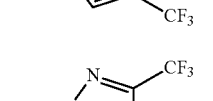 |
| II-A.360 | CF₂CF₃ | C(S)NH₂ | Cl | 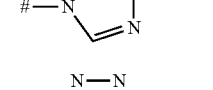 |
| II-A.361 | CF₃ | C(O)NHCH₃ | Cl | CF₂CF₃ |
| II-A.362 | CF₃ | C(O)NHCH₃ | Cl | CF₂CF₂CF₃ |
| II-A.363 | CF₃ | C(O)NHCH₃ | Cl | CF₂CF₂CF₂H |
| II-A.364 | CF₃ | C(O)NHCH₃ | Cl | CH₂CF₂CF₃ |
| II-A.365 | CF₃ | C(O)NHCH₃ | Cl | CH₂CF₂CF₂H |
| II-A.366 | CF₃ | C(O)NHCH₃ | Cl |  |
| II-A.367 | CF₃ | C(O)NHCH₃ | Cl | 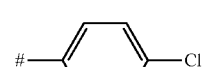 |
| II-A.368 | CF₃ | C(O)NHCH₃ | Cl | 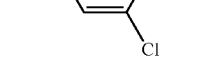 |
| II-A.369 | CF₃ | C(O)NHCH₃ | Cl | 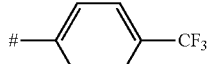 |
| II-A.370 | CF₃ | C(O)NHCH₃ | Cl | 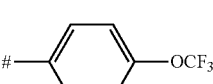 |
| II-A.371 | CF₃ | C(O)NHCH₃ | Cl | 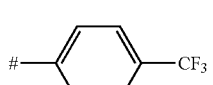 |
| II-A.372 | CF₃ | C(O)NHCH₃ | Cl | 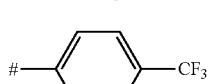 |
| II-A.373 | CF₃ | C(O)NHCH₃ | Cl | 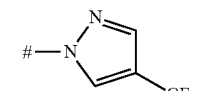 |
| II-A.374 | CF₃ | C(O)NHCH₃ | Cl | 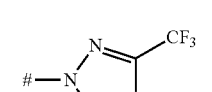 |
| II-A.375 | CF₃ | C(O)NHCH₃ | Cl | 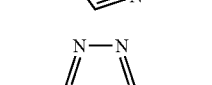 |
| II-A.376 | CF₂H | C(O)NHCH₃ | Cl | CF₂CF₃ |
| II-A.377 | CF₂H | C(O)NHCH₃ | Cl | CF₂CF₂CF₃ |
| II-A.378 | CF₂H | C(O)NHCH₃ | Cl | CF₂CF₂CF₂H |
| II-A.379 | CF₂H | C(O)NHCH₃ | Cl | CH₂CF₂CF₃ |
| II-A.380 | CF₂H | C(O)NHCH₃ | Cl | CH₂CF₂CF₂H |
| II-A.381 | CF₂H | C(O)NHCH₃ | Cl | 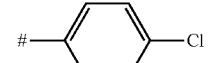 |
| II-A.382 | CF₂H | C(O)NHCH₃ | Cl | 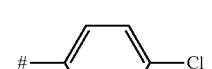 |
| II-A.383 | CF₂H | C(O)NHCH₃ | Cl | 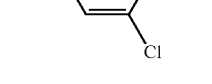 |
| II-A.384 | CF₂H | C(O)NHCH₃ | Cl | 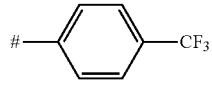 |
| II-A.385 | CF₂H | C(O)NHCH₃ | Cl | 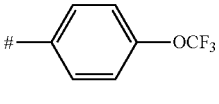 |
| II-A.386 | CF₂H | C(O)NHCH₃ | Cl | 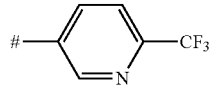 |
| II-A.387 | CF₂H | C(O)NHCH₃ | Cl | 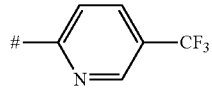 |
| II-A.388 | CF₂H | C(O)NHCH₃ | Cl | 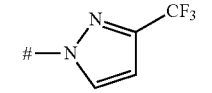 |
| II-A.389 | CF₂H | C(O)NHCH₃ | Cl | 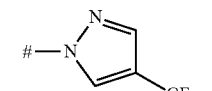 |
| II-A.390 | CF₂H | C(O)NHCH₃ | Cl | 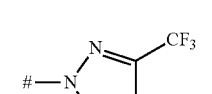 |

TABLE A-continued

| Number of compound | R¹ | R² | R³ | R⁴ |
|---|---|---|---|---|
| II-A.391 | $CF_2CF_3$ | $C(O)NHCH_3$ | Cl | $CF_2CF_3$ |
| II-A.392 | $CF_2CF_3$ | $C(O)NHCH_3$ | Cl | $CF_2CF_2CF_3$ |
| II-A.393 | $CF_2CF_3$ | $C(O)NHCH_3$ | Cl | $CF_2CF_2CF_2H$ |
| II-A.394 | $CF_2CF_3$ | $C(O)NHCH_3$ | Cl | $CH_2CF_2CF_3$ |
| II-A.395 | $CF_2CF_3$ | $C(O)NHCH_3$ | Cl | $CH_2CF_2CF_2H$ |
| II-A.396 | $CF_2CF_3$ | $C(O)NHCH_3$ | Cl | #—C₆H₄—Cl (4-Cl phenyl) |
| II-A.397 | $CF_2CF_3$ | $C(O)NHCH_3$ | Cl | #—C₆H₃—Cl₂ (3,4-dichlorophenyl) |
| II-A.398 | $CF_2CF_3$ | $C(O)NHCH_3$ | Cl | #—C₆H₄—CF₃ (4-CF₃ phenyl) |
| II-A.399 | $CF_2CF_3$ | $C(O)NHCH_3$ | Cl | #—C₆H₄—OCF₃ (4-OCF₃ phenyl) |
| II-A.400 | $CF_2CF_3$ | $C(O)NHCH_3$ | Cl | #—pyridyl—CF₃ (5-#, 2-CF₃) |
| II-A.401 | $CF_2CF_3$ | $C(O)NHCH_3$ | Cl | #—pyridyl—CF₃ (2-#, 5-CF₃) |
| II-A.402 | $CF_2CF_3$ | $C(O)NHCH_3$ | Cl | #—pyrazolyl—CF₃ (N1-#, 3-CF₃) |
| II-A.403 | $CF_2CF_3$ | $C(O)NHCH_3$ | Cl | #—pyrazolyl—CF₃ (N1-#, 4-CF₃) |
| II-A.404 | $CF_2CF_3$ | $C(O)NHCH_3$ | Cl | #—triazolyl—CF₃ |
| II-A.405 | $CF_2CF_3$ | $C(O)NHCH_3$ | Cl | #—thiadiazolyl—CF₃ |
| II-A.406 | $CF_3$ | $C(O)N(CH_3)_2$ | Cl | $CF_2CF_3$ |
| II-A.407 | $CF_3$ | $C(O)N(CH_3)_2$ | Cl | $CF_2CF_2CF_3$ |
| II-A.408 | $CF_3$ | $C(O)N(CH_3)_2$ | Cl | $CF_2CF_2CF_2H$ |
| II-A.409 | $CF_3$ | $C(O)N(CH_3)_2$ | Cl | $CH_2CF_2CF_3$ |
| II-A.410 | $CF_3$ | $C(O)N(CH_3)_2$ | Cl | $CH_2CF_2CF_2H$ |
| II-A.411 | $CF_3$ | $C(O)N(CH_3)_2$ | Cl | #—C₆H₄—Cl (4-Cl phenyl) |
| II-A.412 | $CF_3$ | $C(O)N(CH_3)_2$ | Cl | #—C₆H₃—Cl₂ (3,4-dichlorophenyl) |
| II-A.413 | $CF_3$ | $C(O)N(CH_3)_2$ | Cl | #—C₆H₄—CF₃ (4-CF₃ phenyl) |
| II-A.414 | $CF_3$ | $C(O)N(CH_3)_2$ | Cl | #—C₆H₄—OCF₃ (4-OCF₃ phenyl) |
| II-A.415 | $CF_3$ | $C(O)N(CH_3)_2$ | Cl | #—pyridyl—CF₃ (5-#, 2-CF₃) |
| II-A.416 | $CF_3$ | $C(O)N(CH_3)_2$ | Cl | #—pyridyl—CF₃ (2-#, 5-CF₃) |
| II-A.417 | $CF_3$ | $C(O)N(CH_3)_2$ | Cl | #—pyrazolyl—CF₃ (N1-#, 3-CF₃) |
| II-A.418 | $CF_3$ | $C(O)N(CH_3)_2$ | Cl | #—pyrazolyl—CF₃ (N1-#, 4-CF₃) |
| II-A.419 | $CF_3$ | $C(O)N(CH_3)_2$ | Cl | #—triazolyl—CF₃ |
| II-A.420 | $CF_3$ | $C(O)N(CH_3)_2$ | Cl | #—thiadiazolyl—CF₃ |
| II-A.421 | $CF_2H$ | $C(O)N(CH_3)_2$ | Cl | $CF_2CF_3$ |
| II-A.422 | $CF_2H$ | $C(O)N(CH_3)_2$ | Cl | $CF_2CF_2CF_3$ |
| II-A.423 | $CF_2H$ | $C(O)N(CH_3)_2$ | Cl | $CF_2CF_2CF_2H$ |
| II-A.424 | $CF_2H$ | $C(O)N(CH_3)_2$ | Cl | $CH_2CF_2CF_3$ |
| II-A.425 | $CF_2H$ | $C(O)N(CH_3)_2$ | Cl | $CH_2CF_2CF_2H$ |
| II-A.426 | $CF_2H$ | $C(O)N(CH_3)_2$ | Cl | #—C₆H₄—Cl (4-Cl phenyl) |
| II-A.427 | $CF_2H$ | $C(O)N(CH_3)_2$ | Cl | #—C₆H₃—Cl₂ (3,4-dichlorophenyl) |
| II-A.428 | $CF_2H$ | $C(O)N(CH_3)_2$ | Cl | #—C₆H₄—CF₃ (4-CF₃ phenyl) |
| II-A.429 | $CF_2H$ | $C(O)N(CH_3)_2$ | Cl | #—C₆H₄—OCF₃ (4-OCF₃ phenyl) |
| II-A.430 | $CF_2H$ | $C(O)N(CH_3)_2$ | Cl | #—pyridyl—CF₃ (5-#, 2-CF₃) |

TABLE A-continued

| Number of compound | R¹ | R² | R³ | R⁴ |
|---|---|---|---|---|
| II-A.431 | CF₂H | C(O)N(CH₃)₂ | Cl | 2-pyridyl-5-CF₃ (# at 2-position) |
| II-A.432 | CF₂H | C(O)N(CH₃)₂ | Cl | 1H-pyrazol-1-yl-3-CF₃ |
| II-A.433 | CF₂H | C(O)N(CH₃)₂ | Cl | 1H-pyrazol-1-yl-4-CF₃ |
| II-A.434 | CF₂H | C(O)N(CH₃)₂ | Cl | 1H-1,2,4-triazol-1-yl-3-CF₃ |
| II-A.435 | CF₂H | C(O)N(CH₃)₂ | Cl | 1,3,4-thiadiazol-2-yl-5-CF₃ |
| II-A.436 | CF₂CF₃ | C(O)N(CH₃)₂ | Cl | CF₂CF₃ |
| II-A.437 | CF₂CF₃ | C(O)N(CH₃)₂ | Cl | CF₂CF₂CF₃ |
| II-A.438 | CF₂CF₃ | C(O)N(CH₃)₂ | Cl | CF₂CF₂CF₂H |
| II-A.439 | CF₂CF₃ | C(O)N(CH₃)₂ | Cl | CH₂CF₂CF₃ |
| II-A.440 | CF₂CF₃ | C(O)N(CH₃)₂ | Cl | CH₂CF₂CF₂H |
| II-A.441 | CF₂CF₃ | C(O)N(CH₃)₂ | Cl | 4-Cl-phenyl |
| II-A.442 | CF₂CF₃ | C(O)N(CH₃)₂ | Cl | 3,4-diCl-phenyl |
| II-A.443 | CF₂CF₃ | C(O)N(CH₃)₂ | Cl | 4-CF₃-phenyl |
| II-A.444 | CF₂CF₃ | C(O)N(CH₃)₂ | Cl | 4-OCF₃-phenyl |
| II-A.445 | CF₂CF₃ | C(O)N(CH₃)₂ | Cl | 2-CF₃-pyridin-5-yl |
| II-A.446 | CF₂CF₃ | C(O)N(CH₃)₂ | Cl | 5-CF₃-pyridin-2-yl |
| II-A.447 | CF₂CF₃ | C(O)N(CH₃)₂ | Cl | 1H-pyrazol-1-yl-3-CF₃ |
| II-A.448 | CF₂CF₃ | C(O)N(CH₃)₂ | Cl | 1H-pyrazol-1-yl-4-CF₃ |
| II-A.449 | CF₂CF₃ | C(O)N(CH₃)₂ | Cl | 1H-1,2,4-triazol-1-yl-3-CF₃ |
| II-A.450 | CF₂CF₃ | C(O)N(CH₃)₂ | Cl | 1,3,4-thiadiazol-2-yl-5-CF₃ |
| II-A.451 | CF₃ | CN | CH₃ | CF₂CF₃ |
| II-A.452 | CF₃ | CN | CH₃ | CF₂CF₂CF₃ |
| II-A.453 | CF₃ | CN | CH₃ | CF₂CF₂CF₂H |
| II-A.454 | CF₃ | CN | CH₃ | CH₂CF₂CF₃ |
| II-A.455 | CF₃ | CN | CH₃ | CH₂CF₂CF₂H |
| II-A.456 | CF₃ | CN | CH₃ | 4-Cl-phenyl |
| II-A.457 | CF₃ | CN | CH₃ | 3,4-diCl-phenyl |
| II-A.458 | CF₃ | CN | CH₃ | 4-CF₃-phenyl |
| II-A.459 | CF₃ | CN | CH₃ | 4-OCF₃-phenyl |
| II-A.460 | CF₃ | CN | CH₃ | 2-CF₃-pyridin-5-yl |
| II-A.461 | CF₃ | CN | CH₃ | 5-CF₃-pyridin-2-yl |
| II-A.462 | CF₃ | CN | CH₃ | 1H-pyrazol-1-yl-3-CF₃ |
| II-A.463 | CF₃ | CN | CH₃ | 1H-pyrazol-1-yl-4-CF₃ |
| II-A.464 | CF₃ | CN | CH₃ | 1H-1,2,4-triazol-1-yl-3-CF₃ |
| II-A.465 | CF₃ | CN | CH₃ | 1,3,4-thiadiazol-2-yl-5-CF₃ |
| II-A.466 | CF₂H | CN | CH₃ | CF₂CF₃ |
| II-A.467 | CF₂H | CN | CH₃ | CF₂CF₂CF₃ |
| II-A.468 | CF₂H | CN | CH₃ | CF₂CF₂CF₂H |
| II-A.469 | CF₂H | CN | CH₃ | CH₂CF₂CF₃ |
| II-A.470 | CF₂H | CN | CH₃ | CH₂CF₂CF₂H |

TABLE A-continued

| Number of compound | R¹ | R² | R³ | R⁴ |
|---|---|---|---|---|
| II-A.471 | CF₂H | CN | CH₃ | 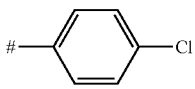 |
| II-A.472 | CF₂H | CN | CH₃ | 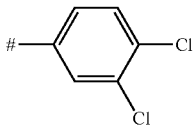 |
| II-A.473 | CF₂H | CN | CH₃ | 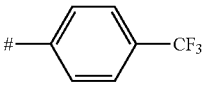 |
| II-A.474 | CF₂H | CN | CH₃ | 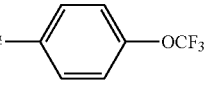 |
| II-A.475 | CF₂H | CN | CH₃ | 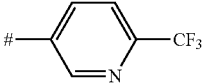 |
| II-A.476 | CF₂H | CN | CH₃ | 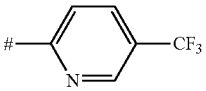 |
| II-A.477 | CF₂H | CN | CH₃ | 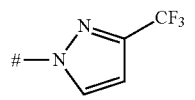 |
| II-A.478 | CF₂H | CN | CH₃ | 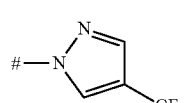 |
| II-A.479 | CF₂H | CN | CH₃ | 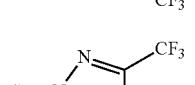 |
| II-A.480 | CF₂H | CN | CH₃ | 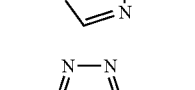 |
| II-A.481 | CF₂CF₃ | CN | CH₃ | CF₂CF₃ |
| II-A.482 | CF₂CF₃ | CN | CH₃ | CF₂CF₂CF₃ |
| II-A.483 | CF₂CF₃ | CN | CH₃ | CF₂CF₂CF₂H |
| II-A.484 | CF₂CF₃ | CN | CH₃ | CH₂CF₂CF₃ |
| II-A.485 | CF₂CF₃ | CN | CH₃ | CH₂CF₂CF₂H |
| II-A.486 | CF₂CF₃ | CN | CH₃ |  |
| II-A.487 | CF₂CF₃ | CN | CH₃ | 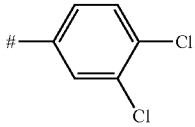 |
| II-A.488 | CF₂CF₃ | CN | CH₃ | 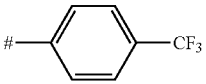 |
| II-A.489 | CF₂CF₃ | CN | CH₃ | 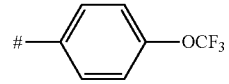 |
| II-A.490 | CF₂CF₃ | CN | CH₃ | 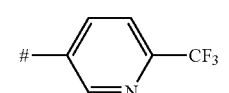 |
| II-A.491 | CF₂CF₃ | CN | CH₃ | 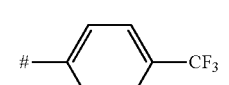 |
| II-A.492 | CF₂CF₃ | CN | CH₃ | 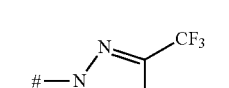 |
| II-A.493 | CF₂CF₃ | CN | CH₃ | 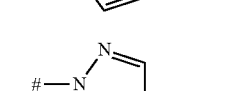 |
| II-A.494 | CF₂CF₃ | CN | CH₃ | 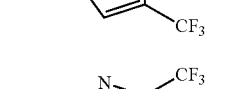 |
| II-A.495 | CF₂CF₃ | CN | CH₃ | 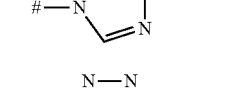 |
| II-A.496 | CF₃ | C(O)CH₃ | CH₃ | CF₂CF₃ |
| II-A.497 | CF₃ | C(O)CH₃ | CH₃ | CF₂CF₂CF₃ |
| II-A.498 | CF₃ | C(O)CH₃ | CH₃ | CF₂CF₂CF₂H |
| II-A.499 | CF₃ | C(O)CH₃ | CH₃ | CH₂CF₂CF₃ |
| II-A.500 | CF₃ | C(O)CH₃ | CH₃ | CH₂CF₂CF₂H |
| II-A.501 | CF₃ | C(O)CH₃ | CH₃ | 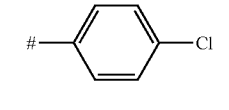 |
| II-A.502 | CF₃ | C(O)CH₃ | CH₃ | 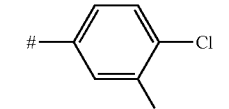 |
| II-A.503 | CF₃ | C(O)CH₃ | CH₃ | 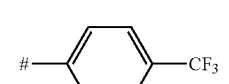 |
| II-A.504 | CF₃ | C(O)CH₃ | CH₃ | 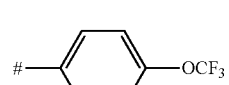 |
| II-A.505 | CF₃ | C(O)CH₃ | CH₃ | 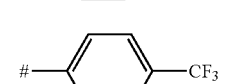 |
| II-A.506 | CF₃ | C(O)CH₃ | CH₃ | 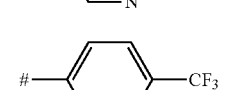 |

TABLE A-continued

| Number of compound | R¹ | R² | R³ | R⁴ |
|---|---|---|---|---|
| II-A.507 | CF₃ | C(O)CH₃ | CH₃ | 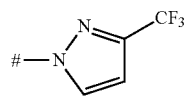 |
| II-A.508 | CF₃ | C(O)CH₃ | CH₃ | 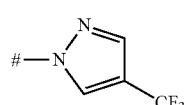 |
| II-A.509 | CF₃ | C(O)CH₃ | CH₃ | 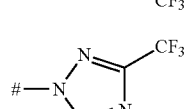 |
| II-A.510 | CF₃ | C(O)CH₃ | CH₃ | 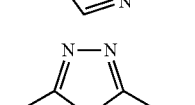 |
| II-A.511 | CF₂H | C(O)CH₃ | CH₃ | CF₂CF₃ |
| II-A.512 | CF₂H | C(O)CH₃ | CH₃ | CF₂CF₂CF₃ |
| II-A.513 | CF₂H | C(O)CH₃ | CH₃ | CF₂CF₂CF₂H |
| II-A.514 | CF₂H | C(O)CH₃ | CH₃ | CH₂CF₂CF₃ |
| II-A.515 | CF₂H | C(O)CH₃ | CH₃ | CH₂CF₂CF₂H |
| II-A.516 | CF₂H | C(O)CH₃ | CH₃ | 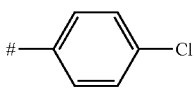 |
| II-A.517 | CF₂H | C(O)CH₃ | CH₃ | 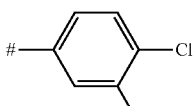 |
| II-A.518 | CF₂H | C(O)CH₃ | CH₃ | 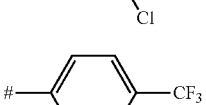 |
| II-A.519 | CF₂H | C(O)CH₃ | CH₃ | 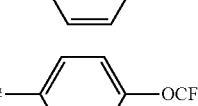 |
| II-A.520 | CF₂H | C(O)CH₃ | CH₃ | 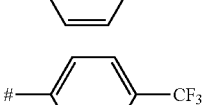 |
| II-A.521 | CF₂H | C(O)CH₃ | CH₃ | 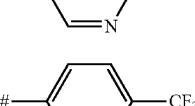 |
| II-A.522 | CF₂H | C(O)CH₃ | CH₃ | 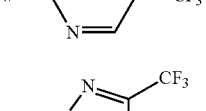 |
| II-A.523 | CF₂H | C(O)CH₃ | CH₃ | 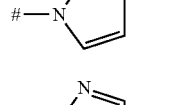 |
| II-A.524 | CF₂H | C(O)CH₃ | CH₃ | 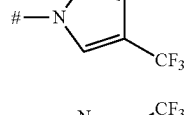 |
| II-A.525 | CF₂H | C(O)CH₃ | CH₃ | 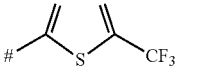 |
| II-A.526 | CF₂CF₃ | C(O)CH₃ | CH₃ | CF₂CF₃ |
| II-A.527 | CF₂CF₃ | C(O)CH₃ | CH₃ | CF₂CF₂CF₃ |
| II-A.528 | CF₂CF₃ | C(O)CH₃ | CH₃ | CF₂CF₂CF₂H |
| II-A.529 | CF₂CF₃ | C(O)CH₃ | CH₃ | CH₂CF₂CF₃ |
| II-A.530 | CF₂CF₃ | C(O)CH₃ | CH₃ | CH₂CF₂CF₂H |
| II-A.531 | CF₂CF₃ | C(O)CH₃ | CH₃ | 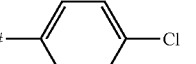 |
| II-A.532 | CF₂CF₃ | C(O)CH₃ | CH₃ | 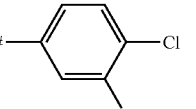 |
| II-A.533 | CF₂CF₃ | C(O)CH₃ | CH₃ | 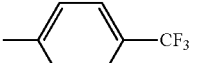 |
| II-A.534 | CF₂CF₃ | C(O)CH₃ | CH₃ | 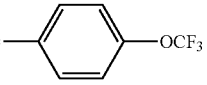 |
| II-A.535 | CF₂CF₃ | C(O)CH₃ | CH₃ | 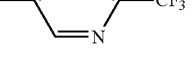 |
| II-A.536 | CF₂CF₃ | C(O)CH₃ | CH₃ | 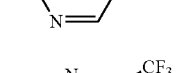 |
| II-A.537 | CF₂CF₃ | C(O)CH₃ | CH₃ | 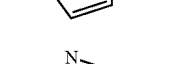 |
| II-A.538 | CF₂CF₃ | C(O)CH₃ | CH₃ | 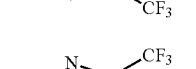 |
| II-A.539 | CF₂CF₃ | C(O)CH₃ | CH₃ | 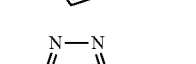 |
| II-A.540 | CF₂CF₃ | C(O)CH₃ | CH₃ | 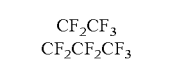 |
| II-A.541 | CF₃ | C(S)NH₂ | CH₃ | CF₂CF₃ |
| II-A.542 | CF₃ | C(S)NH₂ | CH₃ | CF₂CF₂CF₃ |
| II-A.543 | CF₃ | C(S)NH₂ | CH₃ | CF₂CF₂CF₂H |
| II-A.544 | CF₃ | C(S)NH₂ | CH₃ | CH₂CF₂CF₃ |
| II-A.545 | CF₃ | C(S)NH₂ | CH₃ | CH₂CF₂CF₂H |
| II-A.546 | CF₃ | C(S)NH₂ | CH₃ | 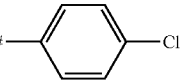 |

TABLE A-continued

| Number of compound | R¹ | R² | R³ | R⁴ |
|---|---|---|---|---|
| II-A.547 | $CF_3$ | $C(S)NH_2$ | $CH_3$ | 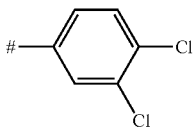 |
| II-A.548 | $CF_3$ | $C(S)NH_2$ | $CH_3$ | 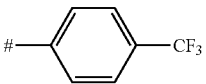 |
| II-A.549 | $CF_3$ | $C(S)NH_2$ | $CH_3$ | 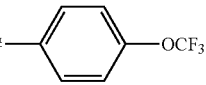 |
| II-A.550 | $CF_3$ | $C(S)NH_2$ | $CH_3$ | 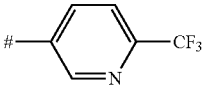 |
| II-A.551 | $CF_3$ | $C(S)NH_2$ | $CH_3$ | 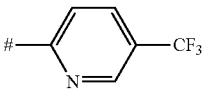 |
| II-A.552 | $CF_3$ | $C(S)NH_2$ | $CH_3$ | 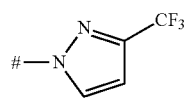 |
| II-A.553 | $CF_3$ | $C(S)NH_2$ | $CH_3$ | 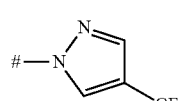 |
| II-A.554 | $CF_3$ | $C(S)NH_2$ | $CH_3$ | 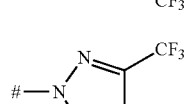 |
| II-A.555 | $CF_3$ | $C(S)NH_2$ | $CH_3$ | 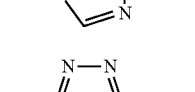 |
| II-A.556 | $CF_2H$ | $C(S)NH_2$ | $CH_3$ | $CF_2CF_3$ |
| II-A.557 | $CF_2H$ | $C(S)NH_2$ | $CH_3$ | $CF_2CF_2CF_3$ |
| II-A.558 | $CF_2H$ | $C(S)NH_2$ | $CH_3$ | $CF_2CF_2CF_2H$ |
| II-A.559 | $CF_2H$ | $C(S)NH_2$ | $CH_3$ | $CH_2CF_2CF_3$ |
| II-A.560 | $CF_2H$ | $C(S)NH_2$ | $CH_3$ | $CH_2CF_2CF_2H$ |
| II-A.561 | $CF_2H$ | $C(S)NH_2$ | $CH_3$ | 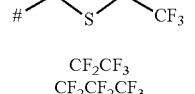 |
| II-A.562 | $CF_2H$ | $C(S)NH_2$ | $CH_3$ | 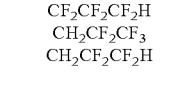 |
| II-A.563 | $CF_2H$ | $C(S)NH_2$ | $CH_3$ | 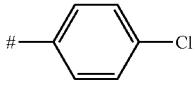 |
| II-A.564 | $CF_2H$ | $C(S)NH_2$ | $CH_3$ | 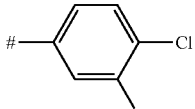 |
| II-A.565 | $CF_2H$ | $C(S)NH_2$ | $CH_3$ | 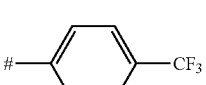 |
| II-A.566 | $CF_2H$ | $C(S)NH_2$ | $CH_3$ | 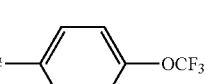 |
| II-A.567 | $CF_2H$ | $C(S)NH_2$ | $CH_3$ |  |
| II-A.568 | $CF_2H$ | $C(S)NH_2$ | $CH_3$ |  |
| II-A.569 | $CF_2H$ | $C(S)NH_2$ | $CH_3$ | 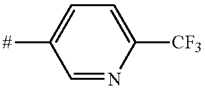 |
| II-A.570 | $CF_2H$ | $C(S)NH_2$ | $CH_3$ | 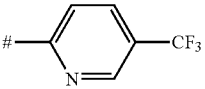 |
| II-A.571 | $CF_2CF_3$ | $C(S)NH_2$ | $CH_3$ | $CF_2CF_3$ |
| II-A.572 | $CF_2CF_3$ | $C(S)NH_2$ | $CH_3$ | $CF_2CF_2CF_3$ |
| II-A.573 | $CF_2CF_3$ | $C(S)NH_2$ | $CH_3$ | $CF_2CF_2CF_2H$ |
| II-A.574 | $CF_2CF_3$ | $C(S)NH_2$ | $CH_3$ | $CH_2CF_2CF_3$ |
| II-A.575 | $CF_2CF_3$ | $C(S)NH_2$ | $CH_3$ | $CH_2CF_2CF_2H$ |
| II-A.576 | $CF_2CF_3$ | $C(S)NH_2$ | $CH_3$ | 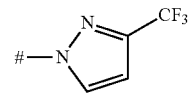 |
| II-A.577 | $CF_2CF_3$ | $C(S)NH_2$ | $CH_3$ | 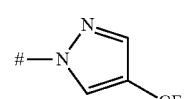 |
| II-A.578 | $CF_2CF_3$ | $C(S)NH_2$ | $CH_3$ | 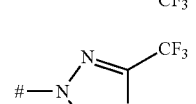 |
| II-A.579 | $CF_2CF_3$ | $C(S)NH_2$ | $CH_3$ | 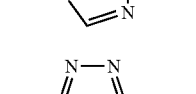 |
| II-A.580 | $CF_2CF_3$ | $C(S)NH_2$ | $CH_3$ | 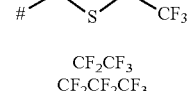 |
| II-A.581 | $CF_2CF_3$ | $C(S)NH_2$ | $CH_3$ | 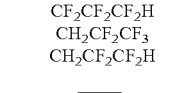 |
| II-A.582 | $CF_2CF_3$ | $C(S)NH_2$ | $CH_3$ | 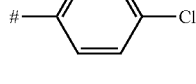 |

TABLE A-continued

| Number of compound | R¹ | R² | R³ | R⁴ |
|---|---|---|---|---|
| II-A.583 | $CF_2CF_3$ | $C(S)NH_2$ | $CH_3$ | #–pyrazole-4-$CF_3$ |
| II-A.584 | $CF_2CF_3$ | $C(S)NH_2$ | $CH_3$ | #–1,2,4-triazole-3-$CF_3$ |
| II-A.585 | $CF_2CF_3$ | $C(S)NH_2$ | $CH_3$ | #–1,3,4-thiadiazole-5-$CF_3$ |
| II-A.586 | $CF_3$ | $C(O)NHCH_3$ | $CH_3$ | $CF_2CF_3$ |
| II-A.587 | $CF_3$ | $C(O)NHCH_3$ | $CH_3$ | $CF_2CF_2CF_3$ |
| II-A.588 | $CF_3$ | $C(O)NHCH_3$ | $CH_3$ | $CF_2CF_2CF_2H$ |
| II-A.589 | $CF_3$ | $C(O)NHCH_3$ | $CH_3$ | $CH_2CF_2CF_3$ |
| II-A.590 | $CF_3$ | $C(O)NHCH_3$ | $CH_3$ | $CH_2CF_2CF_2H$ |
| II-A.591 | $CF_3$ | $C(O)NHCH_3$ | $CH_3$ | #–C₆H₄–4-Cl |
| II-A.592 | $CF_3$ | $C(O)NHCH_3$ | $CH_3$ | #–C₆H₃–3,4-Cl₂ |
| II-A.593 | $CF_3$ | $C(O)NHCH_3$ | $CH_3$ | #–C₆H₄–4-$CF_3$ |
| II-A.594 | $CF_3$ | $C(O)NHCH_3$ | $CH_3$ | #–C₆H₄–4-$OCF_3$ |
| II-A.595 | $CF_3$ | $C(O)NHCH_3$ | $CH_3$ | #–pyridine-2-$CF_3$ |
| II-A.596 | $CF_3$ | $C(O)NHCH_3$ | $CH_3$ | #–pyridine-5-$CF_3$ |
| II-A.597 | $CF_3$ | $C(O)NHCH_3$ | $CH_3$ | #–pyrazole-3-$CF_3$ |
| II-A.598 | $CF_3$ | $C(O)NHCH_3$ | $CH_3$ | #–pyrazole-4-$CF_3$ |
| II-A.599 | $CF_3$ | $C(O)NHCH_3$ | $CH_3$ | #–1,2,4-triazole-3-$CF_3$ |
| II-A.600 | $CF_3$ | $C(O)NHCH_3$ | $CH_3$ | #–1,3,4-thiadiazole-5-$CF_3$ |
| II-A.601 | $CF_2H$ | $C(O)NHCH_3$ | $CH_3$ | $CF_2CF_3$ |
| II-A.602 | $CF_2H$ | $C(O)NHCH_3$ | $CH_3$ | $CF_2CF_2CF_3$ |
| II-A.603 | $CF_2H$ | $C(O)NHCH_3$ | $CH_3$ | $CF_2CF_2CF_2H$ |
| II-A.604 | $CF_2H$ | $C(O)NHCH_3$ | $CH_3$ | $CH_2CF_2CF_3$ |
| II-A.605 | $CF_2H$ | $C(O)NHCH_3$ | $CH_3$ | $CH_2CF_2CF_2H$ |
| II-A.606 | $CF_2H$ | $C(O)NHCH_3$ | $CH_3$ | #–C₆H₄–4-Cl |
| II-A.607 | $CF_2H$ | $C(O)NHCH_3$ | $CH_3$ | #–C₆H₃–3,4-Cl₂ |
| II-A.608 | $CF_2H$ | $C(O)NHCH_3$ | $CH_3$ | #–C₆H₄–4-$CF_3$ |
| II-A.609 | $CF_2H$ | $C(O)NHCH_3$ | $CH_3$ | #–C₆H₄–4-$OCF_3$ |
| II-A.610 | $CF_2H$ | $C(O)NHCH_3$ | $CH_3$ | #–pyridine-2-$CF_3$ |
| II-A.611 | $CF_2H$ | $C(O)NHCH_3$ | $CH_3$ | #–pyridine-5-$CF_3$ |
| II-A.612 | $CF_2H$ | $C(O)NHCH_3$ | $CH_3$ | #–pyrazole-3-$CF_3$ |
| II-A.613 | $CF_2H$ | $C(O)NHCH_3$ | $CH_3$ | #–pyrazole-4-$CF_3$ |
| II-A.614 | $CF_2H$ | $C(O)NHCH_3$ | $CH_3$ | #–1,2,4-triazole-3-$CF_3$ |
| II-A.615 | $CF_2H$ | $C(O)NHCH_3$ | $CH_3$ | #–1,3,4-thiadiazole-5-$CF_3$ |
| II-A.616 | $CF_2CF_3$ | $C(O)NHCH_3$ | $CH_3$ | $CF_2CF_3$ |
| II-A.617 | $CF_2CF_3$ | $C(O)NHCH_3$ | $CH_3$ | $CF_2CF_2CF_3$ |
| II-A.618 | $CF_2CF_3$ | $C(O)NHCH_3$ | $CH_3$ | $CF_2CF_2CF_2H$ |
| II-A.619 | $CF_2CF_3$ | $C(O)NHCH_3$ | $CH_3$ | $CH_2CF_2CF_3$ |
| II-A.620 | $CF_2CF_3$ | $C(O)NHCH_3$ | $CH_3$ | $CH_2CF_2CF_2H$ |
| II-A.621 | $CF_2CF_3$ | $C(O)NHCH_3$ | $CH_3$ | #–C₆H₄–4-Cl |

TABLE A-continued

| Number of compound | R¹ | R² | R³ | R⁴ |
|---|---|---|---|---|
| II-A.622 | CF₂CF₃ | C(O)NHCH₃ | CH₃ | 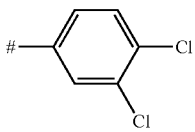 3,4-dichlorophenyl |
| II-A.623 | CF₂CF₃ | C(O)NHCH₃ | CH₃ | 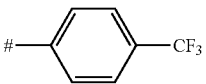 4-CF₃-phenyl |
| II-A.624 | CF₂CF₃ | C(O)NHCH₃ | CH₃ | 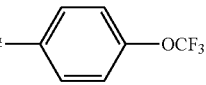 4-OCF₃-phenyl |
| II-A.625 | CF₂CF₃ | C(O)NHCH₃ | CH₃ | 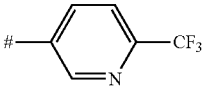 6-CF₃-pyridin-3-yl |
| II-A.626 | CF₂CF₃ | C(O)NHCH₃ | CH₃ | 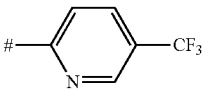 5-CF₃-pyridin-2-yl |
| II-A.627 | CF₂CF₃ | C(O)NHCH₃ | CH₃ | 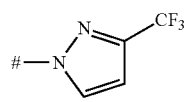 3-CF₃-pyrazol-1-yl |
| II-A.628 | CF₂CF₃ | C(O)NHCH₃ | CH₃ | 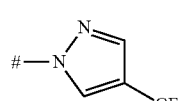 4-CF₃-pyrazol-1-yl |
| II-A.629 | CF₂CF₃ | C(O)NHCH₃ | CH₃ | 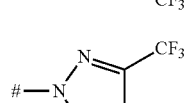 3-CF₃-1,2,4-triazol-1-yl |
| II-A.630 | CF₂CF₃ | C(O)NHCH₃ | CH₃ | 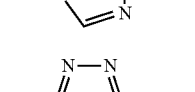 5-CF₃-1,3,4-thiadiazol-2-yl |
| II-A.631 | CF₃ | C(O)N(CH₃)₂ | CH₃ | CF₂CF₃ |
| II-A.632 | CF₃ | C(O)N(CH₃)₂ | CH₃ | CF₂CF₂CF₃ |
| II-A.633 | CF₃ | C(O)N(CH₃)₂ | CH₃ | CF₂CF₂CF₂H |
| II-A.634 | CF₃ | C(O)N(CH₃)₂ | CH₃ | CH₂CF₂CF₃ |
| II-A.635 | CF₃ | C(O)N(CH₃)₂ | CH₃ | CH₂CF₂CF₂H |
| II-A.636 | CF₃ | C(O)N(CH₃)₂ | CH₃ |  4-Cl-phenyl |
| II-A.637 | CF₃ | C(O)N(CH₃)₂ | CH₃ | 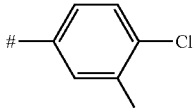 3,4-dichlorophenyl |
| II-A.638 | CF₃ | C(O)N(CH₃)₂ | CH₃ | 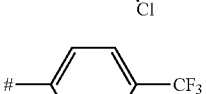 4-CF₃-phenyl |
| II-A.639 | CF₃ | C(O)N(CH₃)₂ | CH₃ | 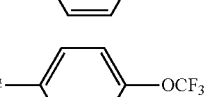 4-OCF₃-phenyl |
| II-A.640 | CF₃ | C(O)N(CH₃)₂ | CH₃ | 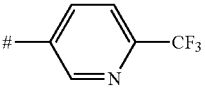 6-CF₃-pyridin-3-yl |
| II-A.641 | CF₃ | C(O)N(CH₃)₂ | CH₃ | 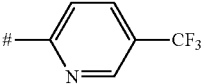 5-CF₃-pyridin-2-yl |
| II-A.642 | CF₃ | C(O)N(CH₃)₂ | CH₃ | 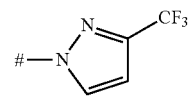 3-CF₃-pyrazol-1-yl |
| II-A.643 | CF₃ | C(O)N(CH₃)₂ | CH₃ | 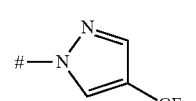 4-CF₃-pyrazol-1-yl |
| II-A.644 | CF₃ | C(O)N(CH₃)₂ | CH₃ | 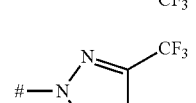 3-CF₃-1,2,4-triazol-1-yl |
| II-A.645 | CF₃ | C(O)N(CH₃)₂ | CH₃ | 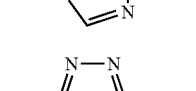 5-CF₃-1,3,4-thiadiazol-2-yl |
| II-A.646 | CF₂H | C(O)N(CH₃)₂ | CH₃ | CF₂CF₃ |
| II-A.647 | CF₂H | C(O)N(CH₃)₂ | CH₃ | CF₂CF₂CF₃ |
| II-A.648 | CF₂H | C(O)N(CH₃)₂ | CH₃ | CF₂CF₂CF₂H |
| II-A.649 | CF₂H | C(O)N(CH₃)₂ | CH₃ | CH₂CF₂CF₃ |
| II-A.650 | CF₂H | C(O)N(CH₃)₂ | CH₃ | CH₂CF₂CF₂H |
| II-A.651 | CF₂H | C(O)N(CH₃)₂ | CH₃ | 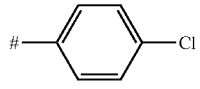 4-Cl-phenyl |
| II-A.652 | CF₂H | C(O)N(CH₃)₂ | CH₃ | 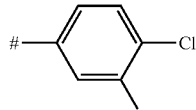 3,4-dichlorophenyl |
| II-A.653 | CF₂H | C(O)N(CH₃)₂ | CH₃ | 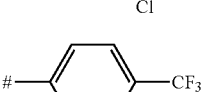 4-CF₃-phenyl |
| II-A.654 | CF₂H | C(O)N(CH₃)₂ | CH₃ | 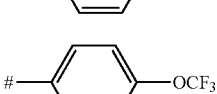 4-OCF₃-phenyl |
| II-A.655 | CF₂H | C(O)N(CH₃)₂ | CH₃ |  6-CF₃-pyridin-3-yl |
| II-A.656 | CF₂H | C(O)N(CH₃)₂ | CH₃ | 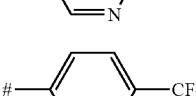 5-CF₃-pyridin-2-yl |
| II-A.657 | CF₂H | C(O)N(CH₃)₂ | CH₃ | 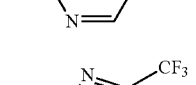 3-CF₃-pyrazol-1-yl |

TABLE A-continued

| Number of compound | R¹ | R² | R³ | R⁴ |
|---|---|---|---|---|
| II-A.658 | $CF_2H$ | $C(O)N(CH_3)_2$ | $CH_3$ | #—pyrazole-$CF_3$ |
| II-A.659 | $CF_2H$ | $C(O)N(CH_3)_2$ | $CH_3$ | #—triazole-$CF_3$ |
| II-A.660 | $CF_2H$ | $C(O)N(CH_3)_2$ | $CH_3$ | #—thiadiazole-$CF_3$ |
| II-A.661 | $CF_2CF_3$ | $C(O)N(CH_3)_2$ | $CH_3$ | $CF_2CF_3$ |
| II-A.662 | $CF_2CF_3$ | $C(O)N(CH_3)_2$ | $CH_3$ | $CF_2CF_2CF_3$ |
| II-A.663 | $CF_2CF_3$ | $C(O)N(CH_3)_2$ | $CH_3$ | $CF_2CF_2CF_2H$ |
| II-A.664 | $CF_2CF_3$ | $C(O)N(CH_3)_2$ | $CH_3$ | $CH_2CF_2CF_3$ |
| II-A.665 | $CF_2CF_3$ | $C(O)N(CH_3)_2$ | $CH_3$ | $CH_2CF_2CF_2H$ |
| II-A.666 | $CF_2CF_3$ | $C(O)N(CH_3)_2$ | $CH_3$ | #—C₆H₄—Cl |
| II-A.667 | $CF_2CF_3$ | $C(O)N(CH_3)_2$ | $CH_3$ | #—C₆H₃(Cl)₂ |
| II-A.668 | $CF_2CF_3$ | $C(O)N(CH_3)_2$ | $CH_3$ | #—C₆H₄—$CF_3$ |
| II-A.669 | $CF_2CF_3$ | $C(O)N(CH_3)_2$ | $CH_3$ | #—C₆H₄—$OCF_3$ |
| II-A.670 | $CF_2CF_3$ | $C(O)N(CH_3)_2$ | $CH_3$ | #—pyridine-$CF_3$ |
| II-A.671 | $CF_2CF_3$ | $C(O)N(CH_3)_2$ | $CH_3$ | #—pyridazine-$CF_3$ |
| II-A.672 | $CF_2CF_3$ | $C(O)N(CH_3)_2$ | $CH_3$ | #—pyrazole-$CF_3$ |
| II-A.673 | $CF_2CF_3$ | $C(O)N(CH_3)_2$ | $CH_3$ | #—pyrazole-$CF_3$ |
| II-A.674 | $CF_2CF_3$ | $C(O)N(CH_3)_2$ | $CH_3$ | #—triazole-$CF_3$ |
| II-A.675 | $CF_2CF_3$ | $C(O)N(CH_3)_2$ | $CH_3$ | #—thiadiazole-$CF_3$ | wherein # denotes the attachment in the molecule

2. Compounds of Formula II-B

Amongst compounds of the formula (II), preference is given to the following compounds of the formula II-B:

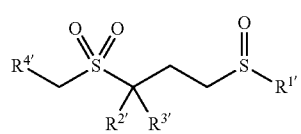

(II-B)

wherein the variables $R^{1'}$, $R^{2'}$, $R^{3'}$ and $R^{4'}$ have the meanings given below in Table B.

The definition of the variables in each line of the table represents an example of a compounds according to the present invention (Compounds II-B.1 to II-B.675).

TABLE B

| Number of compound | R¹ | R² | R³ | R⁴ |
|---|---|---|---|---|
| II-B.1 | $CF_3$ | CN | H | $CF_2CF_3$ |
| II-B.2 | $CF_3$ | CN | H | $CF_2CF_2CF_3$ |
| II-B.3 | $CF_3$ | CN | H | $CF_2CF_2CF_2H$ |
| II-B.4 | $CF_3$ | CN | H | $CH_2CF_2CF_3$ |
| II-B.5 | $CF_3$ | CN | H | $CH_2CF_2CF_2H$ |
| II-B.6 | $CF_3$ | CN | H | #—C₆H₄—Cl |
| II-B.7 | $CF_3$ | CN | H | #—C₆H₃(Cl)₂ |
| II-B.8 | $CF_3$ | CN | H | #—C₆H₄—$CF_3$ |
| II-B.9 | $CF_3$ | CN | H | #—C₆H₄—$OCF_3$ |
| II-B.10 | $CF_3$ | CN | H | #—pyridine-$CF_3$ |
| II-B.11 | $CF_3$ | CN | H | #—pyridine-$CF_3$ |
| II-B.12 | $CF_3$ | CN | H | #—pyrazole-$CF_3$ |

TABLE B-continued

| Number of compound | R$^1$ | R$^2$ | R$^3$ | R$^4$ |
|---|---|---|---|---|
| II-B.13 | CF$_3$ | CN | H | 1-(4-CF$_3$)pyrazol-1-yl |
| II-B.14 | CF$_3$ | CN | H | 3-(CF$_3$)-1,2,4-triazol-1-yl |
| II-B.15 | CF$_3$ | CN | H | 5-(CF$_3$)-1,3,4-thiadiazol-2-yl |
| II-B.16 | CF$_2$H | CN | H | CF$_2$CF$_3$ |
| II-B.17 | CF$_2$H | CN | H | CF$_2$CF$_2$CF$_3$ |
| II-B.18 | CF$_2$H | CN | H | CF$_2$CF$_2$CF$_2$H |
| II-B.19 | CF$_2$H | CN | H | CH$_2$CF$_2$CF$_3$ |
| II-B.20 | CF$_2$H | CN | H | CH$_2$CF$_2$CF$_2$H |
| II-B.21 | CF$_2$H | CN | H | 4-Cl-phenyl |
| II-B.22 | CF$_2$H | CN | H | 3,4-diCl-phenyl |
| II-B.23 | CF$_2$H | CN | H | 4-CF$_3$-phenyl |
| II-B.24 | CF$_2$H | CN | H | 4-OCF$_3$-phenyl |
| II-B.25 | CF$_2$H | CN | H | 6-(CF$_3$)pyridin-3-yl |
| II-B.26 | CF$_2$H | CN | H | 5-(CF$_3$)pyridin-2-yl |
| II-B.27 | CF$_2$H | CN | H | 3-(CF$_3$)pyrazol-1-yl |
| II-B.28 | CF$_2$H | CN | H | 4-(CF$_3$)pyrazol-1-yl |
| II-B.29 | CF$_2$H | CN | H | 3-(CF$_3$)-1,2,4-triazol-1-yl |
| II-B.30 | CF$_2$H | CN | H | 5-(CF$_3$)-1,3,4-thiadiazol-2-yl |
| II-B.31 | CF$_2$CF$_3$ | CN | H | CF$_2$CF$_3$ |
| II-B.32 | CF$_2$CF$_3$ | CN | H | CF$_2$CF$_2$CF$_3$ |
| II-B.33 | CF$_2$CF$_3$ | CN | H | CF$_2$CF$_2$CF$_2$H |
| II-B.34 | CF$_2$CF$_3$ | CN | H | CH$_2$CF$_2$CF$_3$ |
| II-B.35 | CF$_2$CF$_3$ | CN | H | CH$_2$CF$_2$CF$_2$H |
| II-B.36 | CF$_2$CF$_3$ | CN | H | 4-Cl-phenyl |
| II-B.37 | CF$_2$CF$_3$ | CN | H | 3,4-diCl-phenyl |
| II-B.38 | CF$_2$CF$_3$ | CN | H | 4-CF$_3$-phenyl |
| II-B.39 | CF$_2$CF$_3$ | CN | H | 4-OCF$_3$-phenyl |
| II-B.40 | CF$_2$CF$_3$ | CN | H | 6-(CF$_3$)pyridin-3-yl |
| II-B.41 | CF$_2$CF$_3$ | CN | H | 5-(CF$_3$)pyridin-2-yl |
| II-B.42 | CF$_2$CF$_3$ | CN | H | 3-(CF$_3$)pyrazol-1-yl |
| II-B.43 | CF$_2$CF$_3$ | CN | H | 4-(CF$_3$)pyrazol-1-yl |
| II-B.44 | CF$_2$CF$_3$ | CN | H | 3-(CF$_3$)-1,2,4-triazol-1-yl |
| II-B.45 | CF$_2$CF$_3$ | CN | H | 5-(CF$_3$)-1,3,4-thiadiazol-2-yl |
| II-B.46 | CF$_3$ | C(O)CH$_3$ | H | CF$_2$CF$_3$ |
| II-B.47 | CF$_3$ | C(O)CH$_3$ | H | CF$_2$CF$_2$CF$_3$ |
| II-B.48 | CF$_3$ | C(O)CH$_3$ | H | CF$_2$CF$_2$CF$_2$H |
| II-B.49 | CF$_3$ | C(O)CH$_3$ | H | CH$_2$CF$_2$CF$_3$ |
| II-B.50 | CF$_3$ | C(O)CH$_3$ | H | CH$_2$CF$_2$CF$_2$H |
| II-B.51 | CF$_3$ | C(O)CH$_3$ | H | 4-Cl-phenyl |
| II-B.52 | CF$_3$ | C(O)CH$_3$ | H | 3,4-diCl-phenyl |

TABLE B-continued

| Number of compound | R¹ | R² | R³ | R⁴ |
|---|---|---|---|---|
| II-B.53 | $CF_3$ | $C(O)CH_3$ | H |  |
| II-B.54 | $CF_3$ | $C(O)CH_3$ | H |  |
| II-B.55 | $CF_3$ | $C(O)CH_3$ | H | 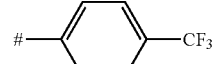 |
| II-B.56 | $CF_3$ | $C(O)CH_3$ | H | 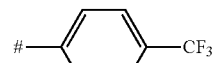 |
| II-B.57 | $CF_3$ | $C(O)CH_3$ | H | 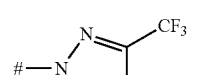 |
| II-B.58 | $CF_3$ | $C(O)CH_3$ | H | 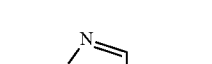 |
| II-B.59 | $CF_3$ | $C(O)CH_3$ | H |  |
| II-B.60 | $CF_3$ | $C(O)CH_3$ | H | 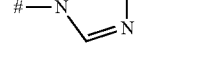 |
| II-B.61 | $CF_2H$ | $C(O)CH_3$ | H | $CF_2CF_3$ |
| II-B.62 | $CF_2H$ | $C(O)CH_3$ | H | $CF_2CF_2CF_3$ |
| II-B.63 | $CF_2H$ | $C(O)CH_3$ | H | $CF_2CF_2CF_2H$ |
| II-B.64 | $CF_2H$ | $C(O)CH_3$ | H | $CH_2CF_2CF_3$ |
| II-B.65 | $CF_2H$ | $C(O)CH_3$ | H | $CH_2CF_2CF_2H$ |
| II-B.66 | $CF_2H$ | $C(O)CH_3$ | H |  |
| II-B.67 | $CF_2H$ | $C(O)CH_3$ | H |  |
| II-B.68 | $CF_2H$ | $C(O)CH_3$ | H | 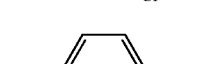 |
| II-B.69 | $CF_2H$ | $C(O)CH_3$ | H | 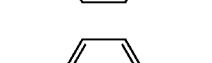 |
| II-B.70 | $CF_2H$ | $C(O)CH_3$ | H | 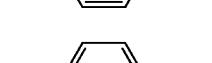 |
| II-B.71 | $CF_2H$ | $C(O)CH_3$ | H | 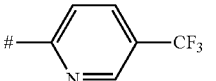 |
| II-B.72 | $CF_2H$ | $C(O)CH_3$ | H | 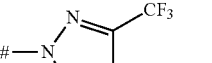 |
| II-B.73 | $CF_2H$ | $C(O)CH_3$ | H | 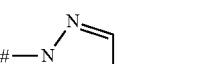 |
| II-B.74 | $CF_2H$ | $C(O)CH_3$ | H | 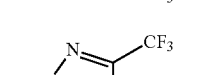 |
| II-B.75 | $CF_2H$ | $C(O)CH_3$ | H | 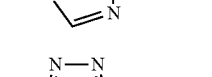 |
| II-B.76 | $CF_2CF_3$ | $C(O)CH_3$ | H | $CF_2CF_3$ |
| II-B.77 | $CF_2CF_3$ | $C(O)CH_3$ | H | $CF_2CF_2CF_3$ |
| II-B.78 | $CF_2CF_3$ | $C(O)CH_3$ | H | $CF_2CF_2CF_2H$ |
| II-B.79 | $CF_2CF_3$ | $C(O)CH_3$ | H | $CH_2CF_2CF_3$ |
| II-B.80 | $CF_2CF_3$ | $C(O)CH_3$ | H | $CH_2CF_2CF_2H$ |
| II-B.81 | $CF_2CF_3$ | $C(O)CH_3$ | H | 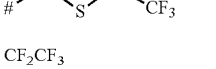 |
| II-B.82 | $CF_2CF_3$ | $C(O)CH_3$ | H | 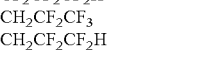 |
| II-B.83 | $CF_2CF_3$ | $C(O)CH_3$ | H | 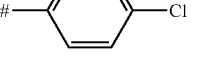 |
| II-B.84 | $CF_2CF_3$ | $C(O)CH_3$ | H | 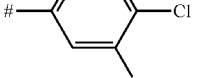 |
| II-B.85 | $CF_2CF_3$ | $C(O)CH_3$ | H | 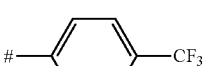 |
| II-B.86 | $CF_2CF_3$ | $C(O)CH_3$ | H | 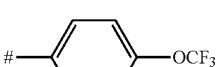 |
| II-B.87 | $CF_2CF_3$ | $C(O)CH_3$ | H | 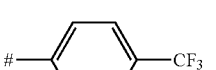 |
| II-B.88 | $CF_2CF_3$ | $C(O)CH_3$ | H | 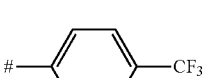 |

TABLE B-continued

| Number of compound | R¹ | R² | R³ | R⁴ |
|---|---|---|---|---|
| II-B.89 | $CF_2CF_3$ | $C(O)CH_3$ | H | 1-(3-CF₃-1,2,4-triazolyl) |
| II-B.90 | $CF_2CF_3$ | $C(O)CH_3$ | H | 2-CF₃-1,3,4-thiadiazol-5-yl |
| II-B.91 | $CF_3$ | $C(S)NH_2$ | H | $CF_2CF_3$ |
| II-B.92 | $CF_3$ | $C(S)NH_2$ | H | $CF_2CF_2CF_3$ |
| II-B.93 | $CF_3$ | $C(S)NH_2$ | H | $CF_2CF_2CF_2H$ |
| II-B.94 | $CF_3$ | $C(S)NH_2$ | H | $CH_2CF_2CF_3$ |
| II-B.95 | $CF_3$ | $C(S)NH_2$ | H | $CH_2CF_2CF_2H$ |
| II-B.96 | $CF_3$ | $C(S)NH_2$ | H | 4-Cl-phenyl |
| II-B.97 | $CF_3$ | $C(S)NH_2$ | H | 3,4-diCl-phenyl |
| II-B.98 | $CF_3$ | $C(S)NH_2$ | H | 4-CF₃-phenyl |
| II-B.99 | $CF_3$ | $C(S)NH_2$ | H | 4-OCF₃-phenyl |
| II-B.100 | $CF_3$ | $C(S)NH_2$ | H | 6-CF₃-pyridin-3-yl |
| II-B.101 | $CF_3$ | $C(S)NH_2$ | H | 5-CF₃-pyridin-2-yl |
| II-B.102 | $CF_3$ | $C(S)NH_2$ | H | 3-CF₃-pyrazol-1-yl |
| II-B.103 | $CF_3$ | $C(S)NH_2$ | H | 4-CF₃-pyrazol-1-yl |
| II-B.104 | $CF_3$ | $C(S)NH_2$ | H | 3-CF₃-1,2,4-triazol-1-yl |
| II-B.105 | $CF_3$ | $C(S)NH_2$ | H | 2-CF₃-1,3,4-thiadiazol-5-yl |
| II-B.106 | $CF_2H$ | $C(S)NH_2$ | H | $CF_2CF_3$ |
| II-B.107 | $CF_2H$ | $C(S)NH_2$ | H | $CF_2CF_2CF_3$ |
| II-B.108 | $CF_2H$ | $C(S)NH_2$ | H | $CF_2CF_2CF_2H$ |
| II-B.109 | $CF_2H$ | $C(S)NH_2$ | H | $CH_2CF_2CF_3$ |
| II-B.110 | $CF_2H$ | $C(S)NH_2$ | H | $CH_2CF_2CF_2H$ |
| II-B.111 | $CF_2H$ | $C(S)NH_2$ | H | 4-Cl-phenyl |
| II-B.112 | $CF_2H$ | $C(S)NH_2$ | H | 3,4-diCl-phenyl |
| II-B.113 | $CF_2H$ | $C(S)NH_2$ | H | 4-CF₃-phenyl |
| II-B.114 | $CF_2H$ | $C(S)NH_2$ | H | 4-OCF₃-phenyl |
| II-B.115 | $CF_2H$ | $C(S)NH_2$ | H | 6-CF₃-pyridin-3-yl |
| II-B.116 | $CF_2H$ | $C(S)NH_2$ | H | 5-CF₃-pyridin-2-yl |
| II-B.117 | $CF_2H$ | $C(S)NH_2$ | H | 3-CF₃-pyrazol-1-yl |
| II-B.118 | $CF_2H$ | $C(S)NH_2$ | H | 4-CF₃-pyrazol-1-yl |
| II-B.119 | $CF_2H$ | $C(S)NH_2$ | H | 3-CF₃-1,2,4-triazol-1-yl |
| II-B.120 | $CF_2H$ | $C(S)NH_2$ | H | 2-CF₃-1,3,4-thiadiazol-5-yl |
| II-B.121 | $CF_2CF_3$ | $C(S)NH_2$ | H | $CF_2CF_3$ |
| II-B.122 | $CF_2CF_3$ | $C(S)NH_2$ | H | $CF_2CF_2CF_3$ |
| II-B.123 | $CF_2CF_3$ | $C(S)NH_2$ | H | $CF_2CF_2CF_2H$ |
| II-B.124 | $CF_2CF_3$ | $C(S)NH_2$ | H | $CH_2CF_2CF_3$ |
| II-B.125 | $CF_2CF_3$ | $C(S)NH_2$ | H | $CH_2CF_2CF_2H$ |
| II-B.126 | $CF_2CF_3$ | $C(S)NH_2$ | H | 4-Cl-phenyl |
| II-B.127 | $CF_2CF_3$ | $C(S)NH_2$ | H | 3,4-diCl-phenyl |
| II-B.128 | $CF_2CF_3$ | $C(S)NH_2$ | H | 4-CF₃-phenyl |

TABLE B-continued

| Number of compound | R¹ | R² | R³ | R⁴ |
|---|---|---|---|---|
| II-B.129 | CF₂CF₃ | C(S)NH₂ | H | #—⟨C₆H₄⟩—OCF₃ (para) |
| II-B.130 | CF₂CF₃ | C(S)NH₂ | H | #—(pyridin-5-yl)-2-CF₃ |
| II-B.131 | CF₂CF₃ | C(S)NH₂ | H | #—(pyridin-2-yl)-5-CF₃ |
| II-B.132 | CF₂CF₃ | C(S)NH₂ | H | #—N-pyrazol-3-CF₃ |
| II-B.133 | CF₂CF₃ | C(S)NH₂ | H | #—N-pyrazol-4-CF₃ |
| II-B.134 | CF₂CF₃ | C(S)NH₂ | H | #—N-(1,2,4-triazol-3-yl)-CF₃ |
| II-B.135 | CF₂CF₃ | C(S)NH₂ | H | #—(1,3,4-thiadiazol-2,5-diyl)-CF₃ |
| II-B.136 | CF₃ | C(O)NHCH₃ | H | CF₂CF₃ |
| II-B.137 | CF₃ | C(O)NHCH₃ | H | CF₂CF₂CF₃ |
| II-B.138 | CF₃ | C(O)NHCH₃ | H | CF₂CF₂CF₂H |
| II-B.139 | CF₃ | C(O)NHCH₃ | H | CH₂CF₂CF₃ |
| II-B.140 | CF₃ | C(O)NHCH₃ | H | CH₂CF₂CF₂H |
| II-B.141 | CF₃ | C(O)NHCH₃ | H | #—⟨C₆H₄⟩—Cl (para) |
| II-B.142 | CF₃ | C(O)NHCH₃ | H | #—⟨C₆H₃⟩—3,4-Cl₂ |
| II-B.143 | CF₃ | C(O)NHCH₃ | H | #—⟨C₆H₄⟩—CF₃ (para) |
| II-B.144 | CF₃ | C(O)NHCH₃ | H | #—⟨C₆H₄⟩—OCF₃ (para) |
| II-B.145 | CF₃ | C(O)NHCH₃ | H | #—(pyridin-5-yl)-2-CF₃ |
| II-B.146 | CF₃ | C(O)NHCH₃ | H | #—(pyridin-2-yl)-5-CF₃ |
| II-B.147 | CF₃ | C(O)NHCH₃ | H | #—N-pyrazol-3-CF₃ |
| II-B.148 | CF₃ | C(O)NHCH₃ | H | #—N-pyrazol-4-CF₃ |
| II-B.149 | CF₃ | C(O)NHCH₃ | H | #—N-(1,2,4-triazol-3-yl)-CF₃ |
| II-B.150 | CF₃ | C(O)NHCH₃ | H | #—(1,3,4-thiadiazol-2,5-diyl)-CF₃ |
| II-B.151 | CF₂H | C(O)NHCH₃ | H | CF₂CF₃ |
| II-B.152 | CF₂H | C(O)NHCH₃ | H | CF₂CF₂CF₃ |
| II-B.153 | CF₂H | C(O)NHCH₃ | H | CF₂CF₂CF₂H |
| II-B.154 | CF₂H | C(O)NHCH₃ | H | CH₂CF₂CF₃ |
| II-B.155 | CF₂H | C(O)NHCH₃ | H | CH₂CF₂CF₂H |
| II-B.156 | CF₂H | C(O)NHCH₃ | H | #—⟨C₆H₄⟩—Cl (para) |
| II-B.157 | CF₂H | C(O)NHCH₃ | H | #—⟨C₆H₃⟩—3,4-Cl₂ |
| II-B.158 | CF₂H | C(O)NHCH₃ | H | #—⟨C₆H₄⟩—CF₃ (para) |
| II-B.159 | CF₂H | C(O)NHCH₃ | H | #—⟨C₆H₄⟩—OCF₃ (para) |
| II-B.160 | CF₂H | C(O)NHCH₃ | H | #—(pyridin-5-yl)-2-CF₃ |
| II-B.161 | CF₂H | C(O)NHCH₃ | H | #—(pyridin-2-yl)-5-CF₃ |
| II-B.162 | CF₂H | C(O)NHCH₃ | H | #—N-pyrazol-3-CF₃ |
| II-B.163 | CF₂H | C(O)NHCH₃ | H | #—N-pyrazol-4-CF₃ |
| II-B.164 | CF₂H | C(O)NHCH₃ | H | #—N-(1,2,4-triazol-3-yl)-CF₃ |

TABLE B-continued

| Number of compound | R¹ | R² | R³ | R⁴ |
|---|---|---|---|---|
| II-B.165 | CF₂H | C(O)NHCH₃ | H | 1,3,4-thiadiazole-2-yl with CF₃ (#-[5-CF₃-1,3,4-thiadiazol-2-yl]) |
| II-B.166 | CF₂CF₃ | C(O)NHCH₃ | H | CF₂CF₃ |
| II-B.167 | CF₂CF₃ | C(O)NHCH₃ | H | CF₂CF₂CF₃ |
| II-B.168 | CF₂CF₃ | C(O)NHCH₃ | H | CF₂CF₂CF₂H |
| II-B.169 | CF₂CF₃ | C(O)NHCH₃ | H | CH₂CF₂CF₃ |
| II-B.170 | CF₂CF₃ | C(O)NHCH₃ | H | CH₂CF₂CF₂H |
| II-B.171 | CF₂CF₃ | C(O)NHCH₃ | H | #–(4-Cl-phenyl) |
| II-B.172 | CF₂CF₃ | C(O)NHCH₃ | H | #–(3,4-diCl-phenyl) |
| II-B.173 | CF₂CF₃ | C(O)NHCH₃ | H | #–(4-CF₃-phenyl) |
| II-B.174 | CF₂CF₃ | C(O)NHCH₃ | H | #–(4-OCF₃-phenyl) |
| II-B.175 | CF₂CF₃ | C(O)NHCH₃ | H | #–(6-CF₃-pyridin-3-yl) |
| II-B.176 | CF₂CF₃ | C(O)NHCH₃ | H | #–(5-CF₃-pyridin-2-yl) |
| II-B.177 | CF₂CF₃ | C(O)NHCH₃ | H | #–(3-CF₃-pyrazol-1-yl) |
| II-B.178 | CF₂CF₃ | C(O)NHCH₃ | H | #–(4-CF₃-pyrazol-1-yl) |
| II-B.179 | CF₂CF₃ | C(O)NHCH₃ | H | #–(3-CF₃-1,2,4-triazol-1-yl) |
| II-B.180 | CF₂CF₃ | C(O)NHCH₃ | H | #–(5-CF₃-1,3,4-thiadiazol-2-yl) |
| II-B.181 | CF₃ | C(O)N(CH₃)₂ | H | CF₂CF₃ |
| II-B.182 | CF₃ | C(O)N(CH₃)₂ | H | CF₂CF₂CF₃ |
| II-B.183 | CF₃ | C(O)N(CH₃)₂ | H | CF₂CF₂CF₂H |
| II-B.184 | CF₃ | C(O)N(CH₃)₂ | H | CH₂CF₂CF₃ |
| II-B.185 | CF₃ | C(O)N(CH₃)₂ | H | CH₂CF₂CF₂H |
| II-B.186 | CF₃ | C(O)N(CH₃)₂ | H | #–(4-Cl-phenyl) |
| II-B.187 | CF₃ | C(O)N(CH₃)₂ | H | #–(3,4-diCl-phenyl) |
| II-B.188 | CF₃ | C(O)N(CH₃)₂ | H | #–(4-CF₃-phenyl) |
| II-B.189 | CF₃ | C(O)N(CH₃)₂ | H | #–(4-OCF₃-phenyl) |
| II-B.190 | CF₃ | C(O)N(CH₃)₂ | H | #–(6-CF₃-pyridin-3-yl) |
| II-B.191 | CF₃ | C(O)N(CH₃)₂ | H | #–(5-CF₃-pyridin-2-yl) |
| II-B.192 | CF₃ | C(O)N(CH₃)₂ | H | #–(3-CF₃-pyrazol-1-yl) |
| II-B.193 | CF₃ | C(O)N(CH₃)₂ | H | #–(4-CF₃-pyrazol-1-yl) |
| II-B.194 | CF₃ | C(O)N(CH₃)₂ | H | #–(3-CF₃-1,2,4-triazol-1-yl) |
| II-B.195 | CF₃ | C(O)N(CH₃)₂ | H | #–(5-CF₃-1,3,4-thiadiazol-2-yl) |
| II-B.196 | CF₂H | C(O)N(CH₃)₂ | H | CF₂CF₃ |
| II-B.197 | CF₂H | C(O)N(CH₃)₂ | H | CF₂CF₂CF₃ |
| II-B.198 | CF₂H | C(O)N(CH₃)₂ | H | CF₂CF₂CF₂H |
| II-B.199 | CF₂H | C(O)N(CH₃)₂ | H | CH₂CF₂CF₃ |
| II-B.200 | CF₂H | C(O)N(CH₃)₂ | H | CH₂CF₂CF₂H |
| II-B.201 | CF₂H | C(O)N(CH₃)₂ | H | #–(4-Cl-phenyl) |
| II-B.202 | CF₂H | C(O)N(CH₃)₂ | H | #–(3,4-diCl-phenyl) |
| II-B.203 | CF₂H | C(O)N(CH₃)₂ | H | #–(4-CF₃-phenyl) |
| II-B.204 | CF₂H | C(O)N(CH₃)₂ | H | #–(4-OCF₃-phenyl) |

TABLE B-continued

| Number of compound | R¹ | R² | R³ | R⁴ |
|---|---|---|---|---|
| II-B.205 | CF₂H | C(O)N(CH₃)₂ | H | 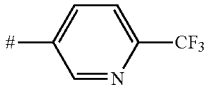 |
| II-B.206 | CF₂H | C(O)N(CH₃)₂ | H | 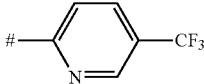 |
| II-B.207 | CF₂H | C(O)N(CH₃)₂ | H | 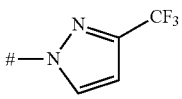 |
| II-B.208 | CF₂H | C(O)N(CH₃)₂ | H | 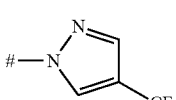 |
| II-B.209 | CF₂H | C(O)N(CH₃)₂ | H | 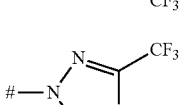 |
| II-B.210 | CF₂H | C(O)N(CH₃)₂ | H | 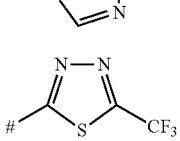 |
| II-B.211 | CF₂CF₃ | C(O)N(CH₃)₂ | H | CF₂CF₃ |
| II-B.212 | CF₂CF₃ | C(O)N(CH₃)₂ | H | CF₂CF₂CF₃ |
| II-B.213 | CF₂CF₃ | C(O)N(CH₃)₂ | H | CF₂CF₂CF₂H |
| II-B.214 | CF₂CF₃ | C(O)N(CH₃)₂ | H | CH₂CF₂CF₃ |
| II-B.215 | CF₂CF₃ | C(O)N(CH₃)₂ | H | CH₂CF₂CF₂H |
| II-B.216 | CF₂CF₃ | C(O)N(CH₃)₂ | H | 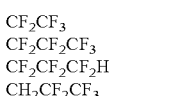 |
| II-B.217 | CF₂CF₃ | C(O)N(CH₃)₂ | H |  |
| II-B.218 | CF₂CF₃ | C(O)N(CH₃)₂ | H | 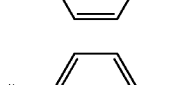 |
| II-B.219 | CF₂CF₃ | C(O)N(CH₃)₂ | H | 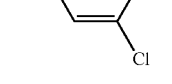 |
| II-B.220 | CF₂CF₃ | C(O)N(CH₃)₂ | H | 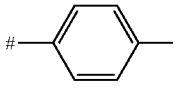 |
| II-B.221 | CF₂CF₃ | C(O)N(CH₃)₂ | H | 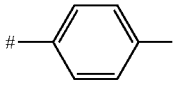 |
| II-B.222 | CF₂CF₃ | C(O)N(CH₃)₂ | H | 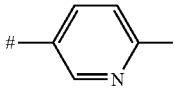 |
| II-B.223 | CF₂CF₃ | C(O)N(CH₃)₂ | H | 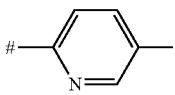 |
| II-B.224 | CF₂CF₃ | C(O)N(CH₃)₂ | H | 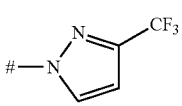 |
| II-B.225 | CF₂CF₃ | C(O)N(CH₃)₂ | H |  |
| II-B.226 | CF₃ | CN | Cl | CF₂CF₃ |
| II-B.227 | CF₃ | CN | Cl | CF₂CF₂CF₃ |
| II-B.228 | CF₃ | CN | Cl | CF₂CF₂CF₂H |
| II-B.229 | CF₃ | CN | Cl | CH₂CF₂CF₃ |
| II-B.230 | CF₃ | CN | Cl | CH₂CF₂CF₂H |
| II-B.231 | CF₃ | CN | Cl |  |
| II-B.232 | CF₃ | CN | Cl | 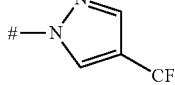 |
| II-B.233 | CF₃ | CN | Cl | 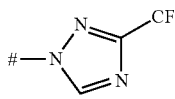 |
| II-B.234 | CF₃ | CN | Cl | 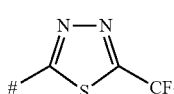 |
| II-B.235 | CF₃ | CN | Cl | 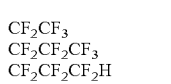 |
| II-B.236 | CF₃ | CN | Cl | 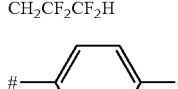 |
| II-B.237 | CF₃ | CN | Cl | 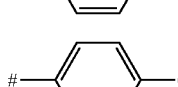 |
| II-B.238 | CF₃ | CN | Cl | 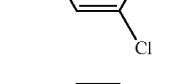 |
| II-B.239 | CF₃ | CN | Cl | 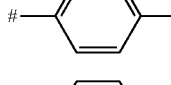 |
| II-B.240 | CF₃ | CN | Cl | 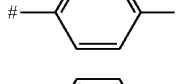 |
| II-B.241 | CF₂H | CN | Cl | CF₂CF₃ |

TABLE B-continued

| Number of compound | R¹ | R² | R³ | R⁴ |
|---|---|---|---|---|
| II-B.242 | $CF_2H$ | CN | Cl | $CF_2CF_2CF_3$ |
| II-B.243 | $CF_2H$ | CN | Cl | $CF_2CF_2CF_2H$ |
| II-B.244 | $CF_2H$ | CN | Cl | $CH_2CF_2CF_3$ |
| II-B.245 | $CF_2H$ | CN | Cl | $CH_2CF_2CF_2H$ |
| II-B.246 | $CF_2H$ | CN | Cl | #—(4-Cl-phenyl) |
| II-B.247 | $CF_2H$ | CN | Cl | #—(3,4-diCl-phenyl) |
| II-B.248 | $CF_2H$ | CN | Cl | #—(4-$CF_3$-phenyl) |
| II-B.249 | $CF_2H$ | CN | Cl | #—(4-$OCF_3$-phenyl) |
| II-B.250 | $CF_2H$ | CN | Cl | #—(6-$CF_3$-pyridin-3-yl) |
| II-B.251 | $CF_2H$ | CN | Cl | #—(5-$CF_3$-pyridin-2-yl) |
| II-B.252 | $CF_2H$ | CN | Cl | #—(3-$CF_3$-pyrazol-1-yl) |
| II-B.253 | $CF_2H$ | CN | Cl | #—(4-$CF_3$-pyrazol-1-yl) |
| II-B.254 | $CF_2H$ | CN | Cl | #—(3-$CF_3$-1,2,4-triazol-1-yl) |
| II-B.255 | $CF_2H$ | CN | Cl | #—(5-$CF_3$-1,3,4-thiadiazol-2-yl) |
| II-B.256 | $CF_2CF_3$ | CN | Cl | $CF_2CF_3$ |
| II-B.257 | $CF_2CF_3$ | CN | Cl | $CF_2CF_2CF_3$ |
| II-B.258 | $CF_2CF_3$ | CN | Cl | $CF_2CF_2CF_2H$ |
| II-B.259 | $CF_2CF_3$ | CN | Cl | $CH_2CF_2CF_3$ |
| II-B.260 | $CF_2CF_3$ | CN | Cl | $CH_2CF_2CF_2H$ |
| II-B.261 | $CF_2CF_3$ | CN | Cl | #—(4-Cl-phenyl) |
| II-B.262 | $CF_2CF_3$ | CN | Cl | #—(3,4-diCl-phenyl) |
| II-B.263 | $CF_2CF_3$ | CN | Cl | #—(4-$CF_3$-phenyl) |
| II-B.264 | $CF_2CF_3$ | CN | Cl | #—(4-$OCF_3$-phenyl) |
| II-B.265 | $CF_2CF_3$ | CN | Cl | #—(6-$CF_3$-pyridin-3-yl) |
| II-B.266 | $CF_2CF_3$ | CN | Cl | #—(5-$CF_3$-pyridin-2-yl) |
| II-B.267 | $CF_2CF_3$ | CN | Cl | #—(3-$CF_3$-pyrazol-1-yl) |
| II-B.268 | $CF_2CF_3$ | CN | Cl | #—(4-$CF_3$-pyrazol-1-yl) |
| II-B.269 | $CF_2CF_3$ | CN | Cl | #—(3-$CF_3$-1,2,4-triazol-1-yl) |
| II-B.270 | $CF_2CF_3$ | CN | Cl | #—(5-$CF_3$-1,3,4-thiadiazol-2-yl) |
| II-B.271 | $CF_3$ | $C(O)CH_3$ | Cl | $CF_2CF_3$ |
| II-B.272 | $CF_3$ | $C(O)CH_3$ | Cl | $CF_2CF_2CF_3$ |
| II-B.273 | $CF_3$ | $C(O)CH_3$ | Cl | $CF_2CF_2CF_2H$ |
| II-B.274 | $CF_3$ | $C(O)CH_3$ | Cl | $CH_2CF_2CF_3$ |
| II-B.275 | $CF_3$ | $C(O)CH_3$ | Cl | $CH_2CF_2CF_2H$ |
| II-B.276 | $CF_3$ | $C(O)CH_3$ | Cl | #—(4-Cl-phenyl) |
| II-B.277 | $CF_3$ | $C(O)CH_3$ | Cl | #—(3,4-diCl-phenyl) |
| II-B.278 | $CF_3$ | $C(O)CH_3$ | Cl | #—(4-$CF_3$-phenyl) |
| II-B.279 | $CF_3$ | $C(O)CH_3$ | Cl | #—(4-$OCF_3$-phenyl) |
| II-B.280 | $CF_3$ | $C(O)CH_3$ | Cl | #—(6-$CF_3$-pyridin-3-yl) |

TABLE B-continued

| Number of compound | R¹ | R² | R³ | R⁴ |
|---|---|---|---|---|
| II-B.281 | $CF_3$ | $C(O)CH_3$ | Cl | 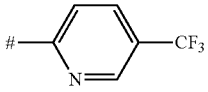 |
| II-B.282 | $CF_3$ | $C(O)CH_3$ | Cl | 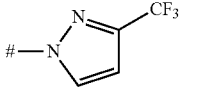 |
| II-B.283 | $CF_3$ | $C(O)CH_3$ | Cl | 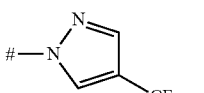 |
| II-B.284 | $CF_3$ | $C(O)CH_3$ | Cl | 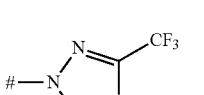 |
| II-B.285 | $CF_3$ | $C(O)CH_3$ | Cl | 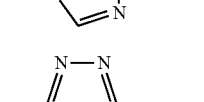 |
| II-B.286 | $CF_2H$ | $C(O)CH_3$ | Cl | $CF_2CF_3$ |
| II-B.287 | $CF_2H$ | $C(O)CH_3$ | Cl | $CF_2CF_2CF_3$ |
| II-B.288 | $CF_2H$ | $C(O)CH_3$ | Cl | $CF_2CF_2CF_2H$ |
| II-B.289 | $CF_2H$ | $C(O)CH_3$ | Cl | $CH_2CF_2CF_3$ |
| II-B.290 | $CF_2H$ | $C(O)CH_3$ | Cl | $CH_2CF_2CF_2H$ |
| II-B.291 | $CF_2H$ | $C(O)CH_3$ | Cl | 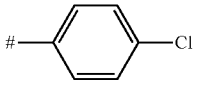 |
| II-B.292 | $CF_2H$ | $C(O)CH_3$ | Cl | 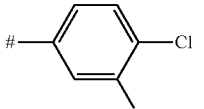 |
| II-B.293 | $CF_2H$ | $C(O)CH_3$ | Cl | 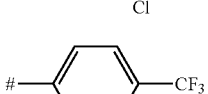 |
| II-B.294 | $CF_2H$ | $C(O)CH_3$ | Cl | 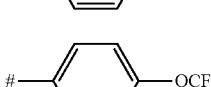 |
| II-B.295 | $CF_2H$ | $C(O)CH_3$ | Cl | 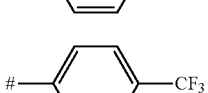 |
| II-B.296 | $CF_2H$ | $C(O)CH_3$ | Cl | 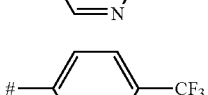 |
| II-B.297 | $CF_2H$ | $C(O)CH_3$ | Cl | 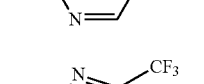 |
| II-B.298 | $CF_2H$ | $C(O)CH_3$ | Cl | 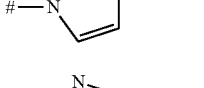 |
| II-B.299 | $CF_2H$ | $C(O)CH_3$ | Cl | 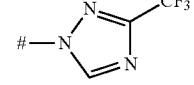 |
| II-B.300 | $CF_2H$ | $C(O)CH_3$ | Cl | 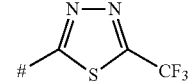 |
| II-B.301 | $CF_2CF_3$ | $C(O)CH_3$ | Cl | $CF_2CF_3$ |
| II-B.302 | $CF_2CF_3$ | $C(O)CH_3$ | Cl | $CF_2CF_2CF_3$ |
| II-B.303 | $CF_2CF_3$ | $C(O)CH_3$ | Cl | $CF_2CF_2CF_2H$ |
| II-B.304 | $CF_2CF_3$ | $C(O)CH_3$ | Cl | $CH_2CF_2CF_3$ |
| II-B.305 | $CF_2CF_3$ | $C(O)CH_3$ | Cl | $CH_2CF_2CF_2H$ |
| II-B.306 | $CF_2CF_3$ | $C(O)CH_3$ | Cl | 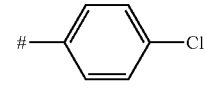 |
| II-B.307 | $CF_2CF_3$ | $C(O)CH_3$ | Cl | 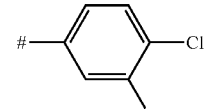 |
| II-B.308 | $CF_2CF_3$ | $C(O)CH_3$ | Cl | 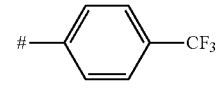 |
| II-B.309 | $CF_2CF_3$ | $C(O)CH_3$ | Cl | 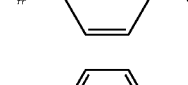 |
| II-B.310 | $CF_2CF_3$ | $C(O)CH_3$ | Cl | 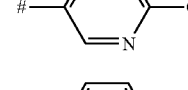 |
| II-B.311 | $CF_2CF_3$ | $C(O)CH_3$ | Cl | 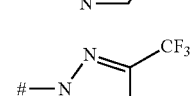 |
| II-B.312 | $CF_2CF_3$ | $C(O)CH_3$ | Cl | 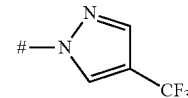 |
| II-B.313 | $CF_2CF_3$ | $C(O)CH_3$ | Cl | 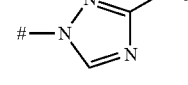 |
| II-B.314 | $CF_2CF_3$ | $C(O)CH_3$ | Cl | 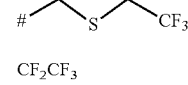 |
| II-B.315 | $CF_2CF_3$ | $C(O)CH_3$ | Cl | 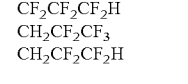 |
| II-B.316 | $CF_3$ | $C(S)NH_2$ | Cl | $CF_2CF_3$ |
| II-B.317 | $CF_3$ | $C(S)NH_2$ | Cl | $CF_2CF_2CF_3$ |
| II-B.318 | $CF_3$ | $C(S)NH_2$ | Cl | $CF_2CF_2CF_2H$ |
| II-B.319 | $CF_3$ | $C(S)NH_2$ | Cl | $CH_2CF_2CF_3$ |
| II-B.320 | $CF_3$ | $C(S)NH_2$ | Cl | $CH_2CF_2CF_2H$ |

TABLE B-continued

| Number of compound | R¹ | R² | R³ | R⁴ |
|---|---|---|---|---|
| II-B.321 | CF₃ | C(S)NH₂ | Cl | 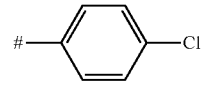 #—⟨C₆H₄⟩—Cl |
| II-B.322 | CF₃ | C(S)NH₂ | Cl | 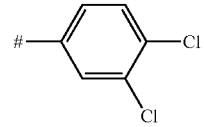 #—⟨C₆H₃⟩(Cl)(Cl) |
| II-B.323 | CF₃ | C(S)NH₂ | Cl |  #—⟨C₆H₄⟩—CF₃ |
| II-B.324 | CF₃ | C(S)NH₂ | Cl | 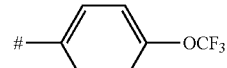 #—⟨C₆H₄⟩—OCF₃ |
| II-B.325 | CF₃ | C(S)NH₂ | Cl | 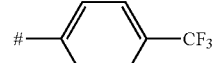 #—⟨pyridyl⟩—CF₃ |
| II-B.326 | CF₃ | C(S)NH₂ | Cl | 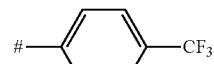 #—⟨pyridyl⟩—CF₃ |
| II-B.327 | CF₃ | C(S)NH₂ | Cl | 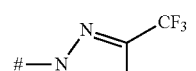 #—pyrazolyl—CF₃ |
| II-B.328 | CF₃ | C(S)NH₂ | Cl | 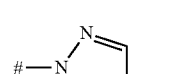 #—pyrazolyl—CF₃ |
| II-B.329 | CF₃ | C(S)NH₂ | Cl | 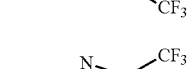 #—triazolyl—CF₃ |
| II-B.330 | CF₃ | C(S)NH₂ | Cl | 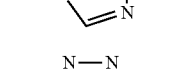 #—thiadiazolyl—CF₃ |
| II-B.331 | CF₂H | C(S)NH₂ | Cl | CF₂CF₃ |
| II-B.332 | CF₂H | C(S)NH₂ | Cl | CF₂CF₂CF₃ |
| II-B.333 | CF₂H | C(S)NH₂ | Cl | CF₂CF₂CF₂H |
| II-B.334 | CF₂H | C(S)NH₂ | Cl | CH₂CF₂CF₃ |
| II-B.335 | CF₂H | C(S)NH₂ | Cl | CH₂CF₂CF₂H |
| II-B.336 | CF₂H | C(S)NH₂ | Cl | 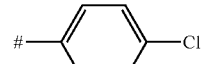 #—⟨C₆H₄⟩—Cl |
| II-B.337 | CF₂H | C(S)NH₂ | Cl | 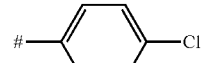 #—⟨C₆H₃⟩(Cl)(Cl) |
| II-B.338 | CF₂H | C(S)NH₂ | Cl | 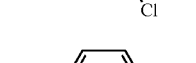 #—⟨C₆H₄⟩—CF₃ |
| II-B.339 | CF₂H | C(S)NH₂ | Cl | 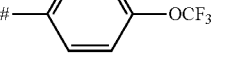 #—⟨C₆H₄⟩—OCF₃ |
| II-B.340 | CF₂H | C(S)NH₂ | Cl | 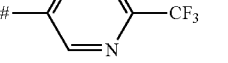 #—⟨pyridyl⟩—CF₃ |
| II-B.341 | CF₂H | C(S)NH₂ | Cl | 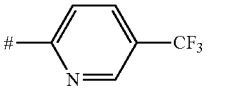 #—⟨pyridyl⟩—CF₃ |
| II-B.342 | CF₂H | C(S)NH₂ | Cl | 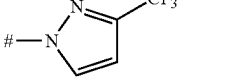 #—pyrazolyl—CF₃ |
| II-B.343 | CF₂H | C(S)NH₂ | Cl | 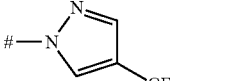 #—pyrazolyl—CF₃ |
| II-B.344 | CF₂H | C(S)NH₂ | Cl | 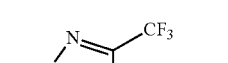 #—triazolyl—CF₃ |
| II-B.345 | CF₂H | C(S)NH₂ | Cl | 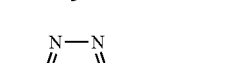 #—thiadiazolyl—CF₃ |
| II-B.346 | CF₂CF₃ | C(S)NH₂ | Cl | CF₂CF₃ |
| II-B.347 | CF₂CF₃ | C(S)NH₂ | Cl | CF₂CF₂CF₃ |
| II-B.348 | CF₂CF₃ | C(S)NH₂ | Cl | CF₂CF₂CF₂H |
| II-B.349 | CF₂CF₃ | C(S)NH₂ | Cl | CH₂CF₂CF₃ |
| II-B.350 | CF₂CF₃ | C(S)NH₂ | Cl | CH₂CF₂CF₂H |
| II-B.351 | CF₂CF₃ | C(S)NH₂ | Cl | 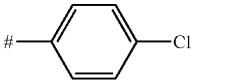 #—⟨C₆H₄⟩—Cl |
| II-B.352 | CF₂CF₃ | C(S)NH₂ | Cl | 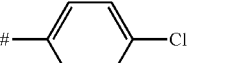 #—⟨C₆H₃⟩(Cl)(Cl) |
| II-B.353 | CF₂CF₃ | C(S)NH₂ | Cl | 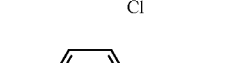 #—⟨C₆H₄⟩—CF₃ |
| II-B.354 | CF₂CF₃ | C(S)NH₂ | Cl | 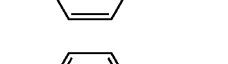 #—⟨C₆H₄⟩—OCF₃ |
| II-B.355 | CF₂CF₃ | C(S)NH₂ | Cl | 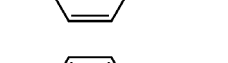 #—⟨pyridazinyl⟩—CF₃ |
| II-B.356 | CF₂CF₃ | C(S)NH₂ | Cl | 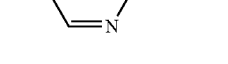 #—⟨pyridazinyl⟩—CF₃ |

TABLE B-continued

| Number of compound | R¹ | R² | R³ | R⁴ |
|---|---|---|---|---|
| II-B.357 | $CF_2CF_3$ | $C(S)NH_2$ | Cl | #-N(pyrazole)-N=C-$CF_3$ (3-CF₃-pyrazol-1-yl) |
| II-B.358 | $CF_2CF_3$ | $C(S)NH_2$ | Cl | #-N(pyrazole), 4-$CF_3$ |
| II-B.359 | $CF_2CF_3$ | $C(S)NH_2$ | Cl | #-N(1,2,4-triazole), 3-$CF_3$ |
| II-B.360 | $CF_2CF_3$ | $C(S)NH_2$ | Cl | #-(1,3,4-thiadiazol-2-yl), 5-$CF_3$ |
| II-B.361 | $CF_3$ | $C(O)NHCH_3$ | Cl | $CF_2CF_3$ |
| II-B.362 | $CF_3$ | $C(O)NHCH_3$ | Cl | $CF_2CF_2CF_3$ |
| II-B.363 | $CF_3$ | $C(O)NHCH_3$ | Cl | $CF_2CF_2CF_2H$ |
| II-B.364 | $CF_3$ | $C(O)NHCH_3$ | Cl | $CH_2CF_2CF_3$ |
| II-B.365 | $CF_3$ | $C(O)NHCH_3$ | Cl | $CH_2CF_2CF_2H$ |
| II-B.366 | $CF_3$ | $C(O)NHCH_3$ | Cl | #-C₆H₄-4-Cl |
| II-B.367 | $CF_3$ | $C(O)NHCH_3$ | Cl | #-C₆H₃-3,4-Cl₂ |
| II-B.368 | $CF_3$ | $C(O)NHCH_3$ | Cl | #-C₆H₄-4-$CF_3$ |
| II-B.369 | $CF_3$ | $C(O)NHCH_3$ | Cl | #-C₆H₄-4-$OCF_3$ |
| II-B.370 | $CF_3$ | $C(O)NHCH_3$ | Cl | #-(pyridin-3-yl), 6-$CF_3$ |
| II-B.371 | $CF_3$ | $C(O)NHCH_3$ | Cl | #-(pyridin-2-yl), 5-$CF_3$ |
| II-B.372 | $CF_3$ | $C(O)NHCH_3$ | Cl | #-N(pyrazol-1-yl), 3-$CF_3$ |
| II-B.373 | $CF_3$ | $C(O)NHCH_3$ | Cl | #-N(pyrazol-1-yl), 4-$CF_3$ |
| II-B.374 | $CF_3$ | $C(O)NHCH_3$ | Cl | #-N(1,2,4-triazol-1-yl), 3-$CF_3$ |
| II-B.375 | $CF_3$ | $C(O)NHCH_3$ | Cl | #-(1,3,4-thiadiazol-2-yl), 5-$CF_3$ |
| II-B.376 | $CF_2H$ | $C(O)NHCH_3$ | Cl | $CF_2CF_3$ |
| II-B.377 | $CF_2H$ | $C(O)NHCH_3$ | Cl | $CF_2CF_2CF_3$ |
| II-B.378 | $CF_2H$ | $C(O)NHCH_3$ | Cl | $CF_2CF_2CF_2H$ |
| II-B.379 | $CF_2H$ | $C(O)NHCH_3$ | Cl | $CH_2CF_2CF_3$ |
| II-B.380 | $CF_2H$ | $C(O)NHCH_3$ | Cl | $CH_2CF_2CF_2H$ |
| II-B.381 | $CF_2H$ | $C(O)NHCH_3$ | Cl | #-C₆H₄-4-Cl |
| II-B.382 | $CF_2H$ | $C(O)NHCH_3$ | Cl | #-C₆H₃-3,4-Cl₂ |
| II-B.383 | $CF_2H$ | $C(O)NHCH_3$ | Cl | #-C₆H₄-4-$CF_3$ |
| II-B.384 | $CF_2H$ | $C(O)NHCH_3$ | Cl | #-C₆H₄-4-$OCF_3$ |
| II-B.385 | $CF_2H$ | $C(O)NHCH_3$ | Cl | #-(pyridin-3-yl), 6-$CF_3$ |
| II-B.386 | $CF_2H$ | $C(O)NHCH_3$ | Cl | #-(pyridin-2-yl), 5-$CF_3$ |
| II-B.387 | $CF_2H$ | $C(O)NHCH_3$ | Cl | #-N(pyrazol-1-yl), 3-$CF_3$ |
| II-B.388 | $CF_2H$ | $C(O)NHCH_3$ | Cl | #-N(pyrazol-1-yl), 4-$CF_3$ |
| II-B.389 | $CF_2H$ | $C(O)NHCH_3$ | Cl | #-N(1,2,4-triazol-1-yl), 3-$CF_3$ |
| II-B.390 | $CF_2H$ | $C(O)NHCH_3$ | Cl | #-(1,3,4-thiadiazol-2-yl), 5-$CF_3$ |
| II-B.391 | $CF_2CF_3$ | $C(O)NHCH_3$ | Cl | $CF_2CF_3$ |
| II-B.392 | $CF_2CF_3$ | $C(O)NHCH_3$ | Cl | $CF_2CF_2CF_3$ |
| II-B.393 | $CF_2CF_3$ | $C(O)NHCH_3$ | Cl | $CF_2CF_2CF_2H$ |
| II-B.394 | $CF_2CF_3$ | $C(O)NHCH_3$ | Cl | $CH_2CF_2CF_3$ |
| II-B.395 | $CF_2CF_3$ | $C(O)NHCH_3$ | Cl | $CH_2CF_2CF_2H$ |
| II-B.396 | $CF_2CF_3$ | $C(O)NHCH_3$ | Cl | #-C₆H₄-4-Cl |

TABLE B-continued

| Number of compound | R¹ | R² | R³ | R⁴ |
|---|---|---|---|---|
| II-B.397 | CF₂CF₃ | C(O)NHCH₃ | Cl | 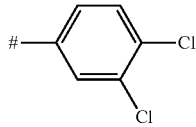 |
| II-B.398 | CF₂CF₃ | C(O)NHCH₃ | Cl | 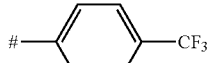 |
| II-B.399 | CF₂CF₃ | C(O)NHCH₃ | Cl | 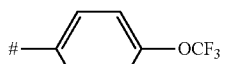 |
| II-B.400 | CF₂CF₃ | C(O)NHCH₃ | Cl | 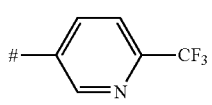 |
| II-B.401 | CF₂CF₃ | C(O)NHCH₃ | Cl | 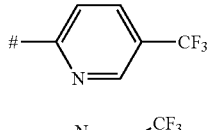 |
| II-B.402 | CF₂CF₃ | C(O)NHCH₃ | Cl | 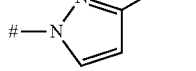 |
| II-B.403 | CF₂CF₃ | C(O)NHCH₃ | Cl | 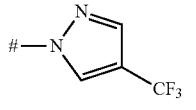 |
| II-B.404 | CF₂CF₃ | C(O)NHCH₃ | Cl | 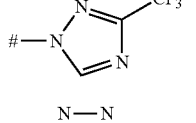 |
| II-B.405 | CF₂CF₃ | C(O)NHCH₃ | Cl | 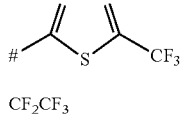 |
| II-B.406 | CF₃ | C(O)N(CH₃)₂ | Cl | CF₂CF₃ |
| II-B.407 | CF₃ | C(O)N(CH₃)₂ | Cl | CF₂CF₂CF₃ |
| II-B.408 | CF₃ | C(O)N(CH₃)₂ | Cl | CF₂CF₂CF₂H |
| II-B.409 | CF₃ | C(O)N(CH₃)₂ | Cl | CH₂CF₂CF₃ |
| II-B.410 | CF₃ | C(O)N(CH₃)₂ | Cl | CH₂CF₂CF₂H |
| II-B.411 | CF₃ | C(O)N(CH₃)₂ | Cl |  |
| II-B.412 | CF₃ | C(O)N(CH₃)₂ | Cl | 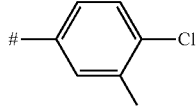 |
| II-B.413 | CF₃ | C(O)N(CH₃)₂ | Cl | 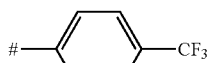 |
| II-B.414 | CF₃ | C(O)N(CH₃)₂ | Cl | 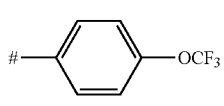 |
| II-B.415 | CF₃ | C(O)N(CH₃)₂ | Cl |  |
| II-B.416 | CF₃ | C(O)N(CH₃)₂ | Cl |  |
| II-B.417 | CF₃ | C(O)N(CH₃)₂ | Cl | 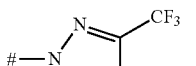 |
| II-B.418 | CF₃ | C(O)N(CH₃)₂ | Cl | 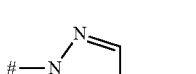 |
| II-B.419 | CF₃ | C(O)N(CH₃)₂ | Cl | 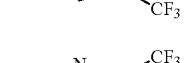 |
| II-B.420 | CF₃ | C(O)N(CH₃)₂ | Cl | 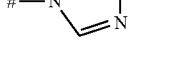 |
| II-B.421 | CF₂H | C(O)N(CH₃)₂ | Cl | CF₂CF₃ |
| II-B.422 | CF₂H | C(O)N(CH₃)₂ | Cl | CF₂CF₂CF₃ |
| II-B.423 | CF₂H | C(O)N(CH₃)₂ | Cl | CF₂CF₂CF₂H |
| II-B.424 | CF₂H | C(O)N(CH₃)₂ | Cl | CH₂CF₂CF₃ |
| II-B.425 | CF₂H | C(O)N(CH₃)₂ | Cl | CH₂CF₂CF₂H |
| II-B.426 | CF₂H | C(O)N(CH₃)₂ | Cl | 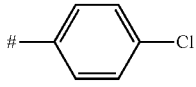 |
| II-B.427 | CF₂H | C(O)N(CH₃)₂ | Cl |  |
| II-B.428 | CF₂H | C(O)N(CH₃)₂ | Cl | 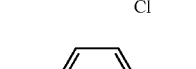 |
| II-B.429 | CF₂H | C(O)N(CH₃)₂ | Cl |  |
| II-B.430 | CF₂H | C(O)N(CH₃)₂ | Cl | 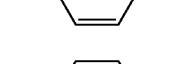 |
| II-B.431 | CF₂H | C(O)N(CH₃)₂ | Cl | 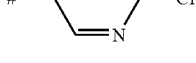 |
| II-B.432 | CF₂H | C(O)N(CH₃)₂ | Cl | 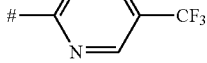 |

TABLE B-continued

| Number of compound | R¹ | R² | R³ | R⁴ |
|---|---|---|---|---|
| II-B.433 | CF₂H | C(O)N(CH₃)₂ | Cl | 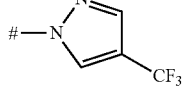 |
| II-B.434 | CF₂H | C(O)N(CH₃)₂ | Cl | 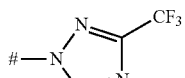 |
| II-B.435 | CF₂H | C(O)N(CH₃)₂ | Cl | 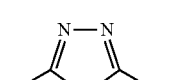 |
| II-B.436 | CF₂CF₃ | C(O)N(CH₃)₂ | Cl | CF₂CF₃ |
| II-B.437 | CF₂CF₃ | C(O)N(CH₃)₂ | Cl | CF₂CF₂CF₃ |
| II-B.438 | CF₂CF₃ | C(O)N(CH₃)₂ | Cl | CF₂CF₂CF₂H |
| II-B.439 | CF₂CF₃ | C(O)N(CH₃)₂ | Cl | CH₂CF₂CF₃ |
| II-B.440 | CF₂CF₃ | C(O)N(CH₃)₂ | Cl | CH₂CF₂CF₂H |
| II-B.441 | CF₂CF₃ | C(O)N(CH₃)₂ | Cl | 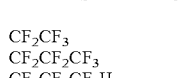 |
| II-B.442 | CF₂CF₃ | C(O)N(CH₃)₂ | Cl | 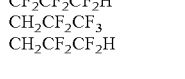 |
| II-B.443 | CF₂CF₃ | C(O)N(CH₃)₂ | Cl | 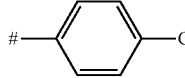 |
| II-B.444 | CF₂CF₃ | C(O)N(CH₃)₂ | Cl | 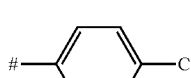 |
| II-B.445 | CF₂CF₃ | C(O)N(CH₃)₂ | Cl | 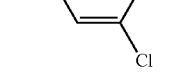 |
| II-B.446 | CF₂CF₃ | C(O)N(CH₃)₂ | Cl | 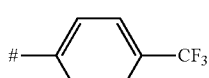 |
| II-B.447 | CF₂CF₃ | C(O)N(CH₃)₂ | Cl |  |
| II-B.448 | CF₂CF₃ | C(O)N(CH₃)₂ | Cl | 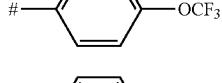 |
| II-B.449 | CF₂CF₃ | C(O)N(CH₃)₂ | Cl | 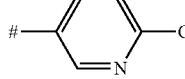 |
| II-B.450 | CF₂CF₃ | C(O)N(CH₃)₂ | Cl | 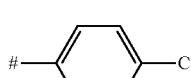 |
| II-B.451 | CF₃ | CN | CH₃ | CF₂CF₃ |
| II-B.452 | CF₃ | CN | CH₃ | CF₂CF₂CF₃ |
| II-B.453 | CF₃ | CN | CH₃ | CF₂CF₂CF₂H |
| II-B.454 | CF₃ | CN | CH₃ | CH₂CF₂CF₃ |
| II-B.455 | CF₃ | CN | CH₃ | CH₂CF₂CF₂H |
| II-B.456 | CF₃ | CN | CH₃ | 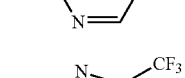 |
| II-B.457 | CF₃ | CN | CH₃ | 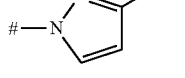 |
| II-B.458 | CF₃ | CN | CH₃ | 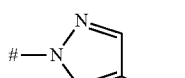 |
| II-B.459 | CF₃ | CN | CH₃ | 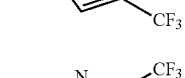 |
| II-B.460 | CF₃ | CN | CH₃ | 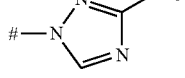 |
| II-B.461 | CF₃ | CN | CH₃ | 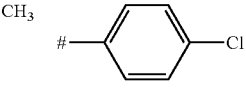 |
| II-B.462 | CF₃ | CN | CH₃ | 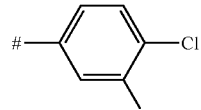 |
| II-B.463 | CF₃ | CN | CH₃ | 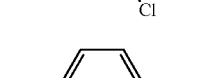 |
| II-B.464 | CF₃ | CN | CH₃ | 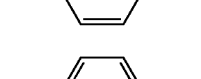 |
| II-B.465 | CF₃ | CN | CH₃ | 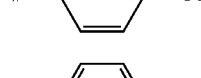 |
| II-B.466 | CF₂H | CN | CH₃ | CF₂CF₃ |
| II-B.467 | CF₂H | CN | CH₃ | CF₂CF₂CF₃ |
| II-B.468 | CF₂H | CN | CH₃ | CF₂CF₂CF₂H |
| II-B.469 | CF₂H | CN | CH₃ | CH₂CF₂CF₃ |
| II-B.470 | CF₂H | CN | CH₃ | CH₂CF₂CF₂H |
| II-B.471 | CF₂H | CN | CH₃ | 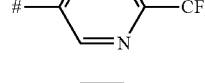 |
| II-B.472 | CF₂H | CN | CH₃ | 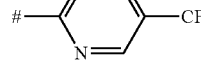 |

TABLE B-continued

| Number of compound | R¹ | R² | R³ | R⁴ |
|---|---|---|---|---|
| II-B.473 | CF₂H | CN | CH₃ | #—⟨C₆H₄⟩—CF₃ (para) |
| II-B.474 | CF₂H | CN | CH₃ | #—⟨C₆H₄⟩—OCF₃ (para) |
| II-B.475 | CF₂H | CN | CH₃ | #—⟨pyridyl⟩—CF₃ |
| II-B.476 | CF₂H | CN | CH₃ | #—⟨pyridyl⟩—CF₃ |
| II-B.477 | CF₂H | CN | CH₃ | #—⟨pyrazolyl⟩—CF₃ |
| II-B.478 | CF₂H | CN | CH₃ | #—⟨pyrazolyl⟩—CF₃ |
| II-B.479 | CF₂H | CN | CH₃ | #—⟨triazolyl⟩—CF₃ |
| II-B.480 | CF₂H | CN | CH₃ | #—⟨thiadiazolyl⟩—CF₃ |
| II-B.481 | CF₂CF₃ | CN | CH₃ | CF₂CF₃ |
| II-B.482 | CF₂CF₃ | CN | CH₃ | CF₂CF₂CF₃ |
| II-B.483 | CF₂CF₃ | CN | CH₃ | CF₂CF₂CF₂H |
| II-B.484 | CF₂CF₃ | CN | CH₃ | CH₂CF₂CF₃ |
| II-B.485 | CF₂CF₃ | CN | CH₃ | CH₂CF₂CF₂H |
| II-B.486 | CF₂CF₃ | CN | CH₃ | #—⟨C₆H₄⟩—Cl (para) |
| II-B.487 | CF₂CF₃ | CN | CH₃ | #—⟨C₆H₃⟩—Cl,Cl (3,4) |
| II-B.488 | CF₂CF₃ | CN | CH₃ | #—⟨C₆H₄⟩—CF₃ (para) |
| II-B.489 | CF₂CF₃ | CN | CH₃ | #—⟨C₆H₄⟩—OCF₃ (para) |
| II-B.490 | CF₂CF₃ | CN | CH₃ | #—⟨pyridyl⟩—CF₃ |
| II-B.491 | CF₂CF₃ | CN | CH₃ | #—⟨pyridyl⟩—CF₃ |
| II-B.492 | CF₂CF₃ | CN | CH₃ | #—⟨pyrazolyl⟩—CF₃ |
| II-B.493 | CF₂CF₃ | CN | CH₃ | #—⟨pyrazolyl⟩—CF₃ |
| II-B.494 | CF₂CF₃ | CN | CH₃ | #—⟨triazolyl⟩—CF₃ |
| II-B.495 | CF₂CF₃ | CN | CH₃ | #—⟨thiadiazolyl⟩—CF₃ |
| II-B.496 | CF₃ | C(O)CH₃ | CH₃ | CF₂CF₃ |
| II-B.497 | CF₃ | C(O)CH₃ | CH₃ | CF₂CF₂CF₃ |
| II-B.498 | CF₃ | C(O)CH₃ | CH₃ | CF₂CF₂CF₂H |
| II-B.499 | CF₃ | C(O)CH₃ | CH₃ | CH₂CF₂CF₃ |
| II-B.500 | CF₃ | C(O)CH₃ | CH₃ | CH₂CF₂CF₂H |
| II-B.501 | CF₃ | C(O)CH₃ | CH₃ | #—⟨C₆H₄⟩—Cl (para) |
| II-B.502 | CF₃ | C(O)CH₃ | CH₃ | #—⟨C₆H₃⟩—Cl,Cl (3,4) |
| II-B.503 | CF₃ | C(O)CH₃ | CH₃ | #—⟨C₆H₄⟩—CF₃ (para) |
| II-B.504 | CF₃ | C(O)CH₃ | CH₃ | #—⟨C₆H₄⟩—OCF₃ (para) |
| II-B.505 | CF₃ | C(O)CH₃ | CH₃ | #—⟨pyridyl⟩—CF₃ |
| II-B.506 | CF₃ | C(O)CH₃ | CH₃ | #—⟨pyridyl⟩—CF₃ |
| II-B.507 | CF₃ | C(O)CH₃ | CH₃ | #—⟨pyrazolyl⟩—CF₃ |
| II-B.508 | CF₃ | C(O)CH₃ | CH₃ | #—⟨pyrazolyl⟩—CF₃ |

TABLE B-continued

| Number of compound | R¹ | R² | R³ | R⁴ |
|---|---|---|---|---|
| II-B.509 | $CF_3$ | $C(O)CH_3$ | $CH_3$ | 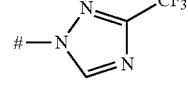 |
| II-B.510 | $CF_3$ | $C(O)CH_3$ | $CH_3$ | 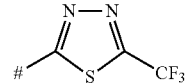 |
| II-B.511 | $CF_2H$ | $C(O)CH_3$ | $CH_3$ | $CF_2CF_3$ |
| II-B.512 | $CF_2H$ | $C(O)CH_3$ | $CH_3$ | $CF_2CF_2CF_3$ |
| II-B.513 | $CF_2H$ | $C(O)CH_3$ | $CH_3$ | $CF_2CF_2CF_2H$ |
| II-B.514 | $CF_2H$ | $C(O)CH_3$ | $CH_3$ | $CH_2CF_2CF_3$ |
| II-B.515 | $CF_2H$ | $C(O)CH_3$ | $CH_3$ | $CH_2CF_2CF_2H$ |
| II-B.516 | $CF_2H$ | $C(O)CH_3$ | $CH_3$ | 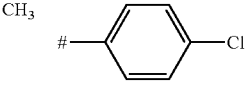 |
| II-B.517 | $CF_2H$ | $C(O)CH_3$ | $CH_3$ | 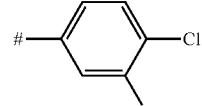 |
| II-B.518 | $CF_2H$ | $C(O)CH_3$ | $CH_3$ | 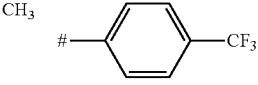 |
| II-B.519 | $CF_2H$ | $C(O)CH_3$ | $CH_3$ | 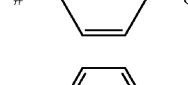 |
| II-B.520 | $CF_2H$ | $C(O)CH_3$ | $CH_3$ | 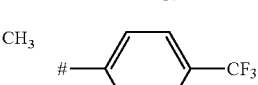 |
| II-B.521 | $CF_2H$ | $C(O)CH_3$ | $CH_3$ | 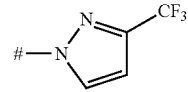 |
| II-B.522 | $CF_2H$ | $C(O)CH_3$ | $CH_3$ | 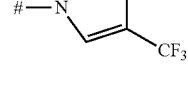 |
| II-B.523 | $CF_2H$ | $C(O)CH_3$ | $CH_3$ | 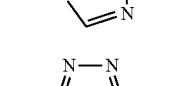 |
| II-B.524 | $CF_2H$ | $C(O)CH_3$ | $CH_3$ | 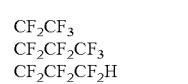 |
| II-B.525 | $CF_2H$ | $C(O)CH_3$ | $CH_3$ |  |
| II-B.526 | $CF_2CF_3$ | $C(O)CH_3$ | $CH_3$ | $CF_2CF_3$ |
| II-B.527 | $CF_2CF_3$ | $C(O)CH_3$ | $CH_3$ | $CF_2CF_2CF_3$ |
| II-B.528 | $CF_2CF_3$ | $C(O)CH_3$ | $CH_3$ | $CF_2CF_2CF_2H$ |
| II-B.529 | $CF_2CF_3$ | $C(O)CH_3$ | $CH_3$ | $CH_2CF_2CF_3$ |
| II-B.530 | $CF_2CF_3$ | $C(O)CH_3$ | $CH_3$ | $CH_2CF_2CF_2H$ |
| II-B.531 | $CF_2CF_3$ | $C(O)CH_3$ | $CH_3$ | 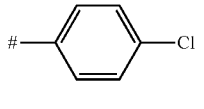 |
| II-B.532 | $CF_2CF_3$ | $C(O)CH_3$ | $CH_3$ | 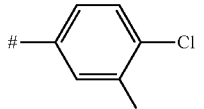 |
| II-B.533 | $CF_2CF_3$ | $C(O)CH_3$ | $CH_3$ | 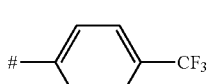 |
| II-B.534 | $CF_2CF_3$ | $C(O)CH_3$ | $CH_3$ | 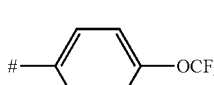 |
| II-B.535 | $CF_2CF_3$ | $C(O)CH_3$ | $CH_3$ | 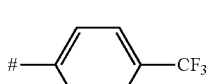 |
| II-B.536 | $CF_2CF_3$ | $C(O)CH_3$ | $CH_3$ | 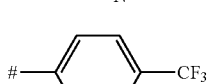 |
| II-B.537 | $CF_2CF_3$ | $C(O)CH_3$ | $CH_3$ | 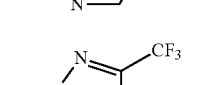 |
| II-B.538 | $CF_2CF_3$ | $C(O)CH_3$ | $CH_3$ | 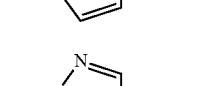 |
| II-B.539 | $CF_2CF_3$ | $C(O)CH_3$ | $CH_3$ | 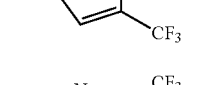 |
| II-B.540 | $CF_2CF_3$ | $C(O)CH_3$ | $CH_3$ | 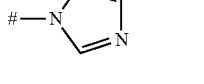 |
| II-B.541 | $CF_3$ | $C(S)NH_2$ | $CH_3$ | $CF_2CF_3$ |
| II-B.542 | $CF_3$ | $C(S)NH_2$ | $CH_3$ | $CF_2CF_2CF_3$ |
| II-B.543 | $CF_3$ | $C(S)NH_2$ | $CH_3$ | $CF_2CF_2CF_2H$ |
| II-B.544 | $CF_3$ | $C(S)NH_2$ | $CH_3$ | $CH_2CF_2CF_3$ |
| II-B.545 | $CF_3$ | $C(S)NH_2$ | $CH_3$ | $CH_2CF_2CF_2H$ |
| II-B.546 | $CF_3$ | $C(S)NH_2$ | $CH_3$ | 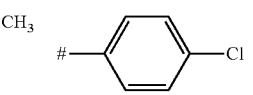 |
| II-B.547 | $CF_3$ | $C(S)NH_2$ | $CH_3$ | 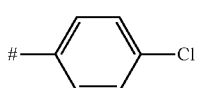 |
| II-B.548 | $CF_3$ | $C(S)NH_2$ | $CH_3$ | 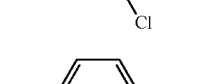 |

TABLE B-continued

| Number of compound | R¹ | R² | R³ | R⁴ |
|---|---|---|---|---|
| II-B.549 | $CF_3$ | $C(S)NH_2$ | $CH_3$ | 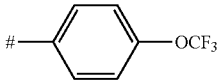 |
| II-B.550 | $CF_3$ | $C(S)NH_2$ | $CH_3$ | 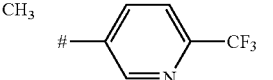 |
| II-B.551 | $CF_3$ | $C(S)NH_2$ | $CH_3$ | 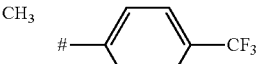 |
| II-B.552 | $CF_3$ | $C(S)NH_2$ | $CH_3$ | 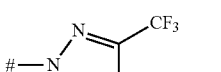 |
| II-B.553 | $CF_3$ | $C(S)NH_2$ | $CH_3$ | 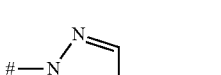 |
| II-B.554 | $CF_3$ | $C(S)NH_2$ | $CH_3$ |  |
| II-B.555 | $CF_3$ | $C(S)NH_2$ | $CH_3$ | 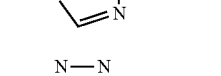 |
| II-B.556 | $CF_2H$ | $C(S)NH_2$ | $CH_3$ | $CF_2CF_3$ |
| II-B.557 | $CF_2H$ | $C(S)NH_2$ | $CH_3$ | $CF_2CF_2CF_3$ |
| II-B.558 | $CF_2H$ | $C(S)NH_2$ | $CH_3$ | $CF_2CF_2CF_2H$ |
| II-B.559 | $CF_2H$ | $C(S)NH_2$ | $CH_3$ | $CH_2CF_2CF_3$ |
| II-B.560 | $CF_2H$ | $C(S)NH_2$ | $CH_3$ | $CH_2CF_2CF_2H$ |
| II-B.561 | $CF_2H$ | $C(S)NH_2$ | $CH_3$ | 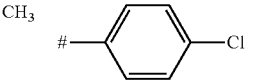 |
| II-B.562 | $CF_2H$ | $C(S)NH_2$ | $CH_3$ | 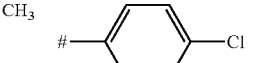 |
| II-B.563 | $CF_2H$ | $C(S)NH_2$ | $CH_3$ | 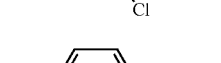 |
| II-B.564 | $CF_2H$ | $C(S)NH_2$ | $CH_3$ | 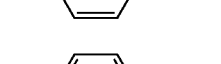 |
| II-B.565 | $CF_2H$ | $C(S)NH_2$ | $CH_3$ | 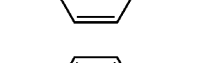 |
| II-B.566 | $CF_2H$ | $C(S)NH_2$ | $CH_3$ | 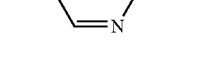 |
| II-B.567 | $CF_2H$ | $C(S)NH_2$ | $CH_3$ | 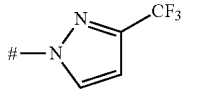 |
| II-B.568 | $CF_2H$ | $C(S)NH_2$ | $CH_3$ | 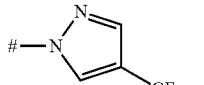 |
| II-B.569 | $CF_2H$ | $C(S)NH_2$ | $CH_3$ | 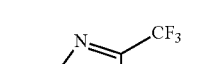 |
| II-B.570 | $CF_2H$ | $C(S)NH_2$ | $CH_3$ | 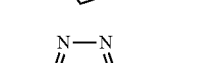 |
| II-B.571 | $CF_2CF_3$ | $C(S)NH_2$ | $CH_3$ | $CF_2CF_3$ |
| II-B.572 | $CF_2CF_3$ | $C(S)NH_2$ | $CH_3$ | $CF_2CF_2CF_3$ |
| II-B.573 | $CF_2CF_3$ | $C(S)NH_2$ | $CH_3$ | $CF_2CF_2CF_2H$ |
| II-B.574 | $CF_2CF_3$ | $C(S)NH_2$ | $CH_3$ | $CH_2CF_2CF_3$ |
| II-B.575 | $CF_2CF_3$ | $C(S)NH_2$ | $CH_3$ | $CH_2CF_2CF_2H$ |
| II-B.576 | $CF_2CF_3$ | $C(S)NH_2$ | $CH_3$ | 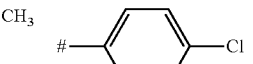 |
| II-B.577 | $CF_2CF_3$ | $C(S)NH_2$ | $CH_3$ | 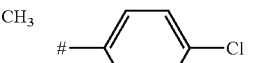 |
| II-B.578 | $CF_2CF_3$ | $C(S)NH_2$ | $CH_3$ | 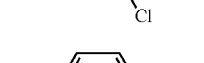 |
| II-B.579 | $CF_2CF_3$ | $C(S)NH_2$ | $CH_3$ | 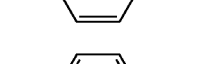 |
| II-B.580 | $CF_2CF_3$ | $C(S)NH_2$ | $CH_3$ | 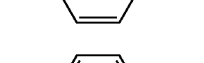 |
| II-B.581 | $CF_2CF_3$ | $C(S)NH_2$ | $CH_3$ | 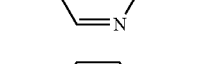 |
| II-B.582 | $CF_2CF_3$ | $C(S)NH_2$ | $CH_3$ | 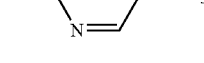 |
| II-B.583 | $CF_2CF_3$ | $C(S)NH_2$ | $CH_3$ | 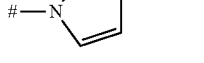 |
| II-B.584 | $CF_2CF_3$ | $C(S)NH_2$ | $CH_3$ | 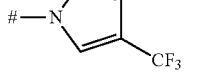 |

TABLE B-continued

| Number of compound | R¹ | R² | R³ | R⁴ |
|---|---|---|---|---|
| II-B.585 | CF₂CF₃ | C(S)NH₂ | CH₃ | ![1,3,4-thiadiazole-CF₃] |
| II-B.586 | CF₃ | C(O)NHCH₃ | CH₃ | CF₂CF₃ |
| II-B.587 | CF₃ | C(O)NHCH₃ | CH₃ | CF₂CF₂CF₃ |
| II-B.588 | CF₃ | C(O)NHCH₃ | CH₃ | CF₂CF₂CF₂H |
| II-B.589 | CF₃ | C(O)NHCH₃ | CH₃ | CH₂CF₂CF₃ |
| II-B.590 | CF₃ | C(O)NHCH₃ | CH₃ | CH₂CF₂CF₂H |
| II-B.591 | CF₃ | C(O)NHCH₃ | CH₃ | 4-Cl-phenyl |
| II-B.592 | CF₃ | C(O)NHCH₃ | CH₃ | 3,4-diCl-phenyl |
| II-B.593 | CF₃ | C(O)NHCH₃ | CH₃ | 4-CF₃-phenyl |
| II-B.594 | CF₃ | C(O)NHCH₃ | CH₃ | 4-OCF₃-phenyl |
| II-B.595 | CF₃ | C(O)NHCH₃ | CH₃ | 6-CF₃-pyridin-3-yl |
| II-B.596 | CF₃ | C(O)NHCH₃ | CH₃ | 5-CF₃-pyridin-2-yl |
| II-B.597 | CF₃ | C(O)NHCH₃ | CH₃ | 3-CF₃-pyrazol-1-yl |
| II-B.598 | CF₃ | C(O)NHCH₃ | CH₃ | 4-CF₃-pyrazol-1-yl |
| II-B.599 | CF₃ | C(O)NHCH₃ | CH₃ | 3-CF₃-1,2,4-triazol-1-yl |
| II-B.600 | CF₃ | C(O)NHCH₃ | CH₃ | 1,3,4-thiadiazole-CF₃ |
| II-B.601 | CF₂H | C(O)NHCH₃ | CH₃ | CF₂CF₃ |
| II-B.602 | CF₂H | C(O)NHCH₃ | CH₃ | CF₂CF₂CF₃ |
| II-B.603 | CF₂H | C(O)NHCH₃ | CH₃ | CF₂CF₂CF₂H |
| II-B.604 | CF₂H | C(O)NHCH₃ | CH₃ | CH₂CF₂CF₃ |
| II-B.605 | CF₂H | C(O)NHCH₃ | CH₃ | CH₂CF₂CF₂H |
| II-B.606 | CF₂H | C(O)NHCH₃ | CH₃ | 4-Cl-phenyl |
| II-B.607 | CF₂H | C(O)NHCH₃ | CH₃ | 3,4-diCl-phenyl |
| II-B.608 | CF₂H | C(O)NHCH₃ | CH₃ | 4-CF₃-phenyl |
| II-B.609 | CF₂H | C(O)NHCH₃ | CH₃ | 4-OCF₃-phenyl |
| II-B.610 | CF₂H | C(O)NHCH₃ | CH₃ | 6-CF₃-pyridin-3-yl |
| II-B.611 | CF₂H | C(O)NHCH₃ | CH₃ | 5-CF₃-pyridin-2-yl |
| II-B.612 | CF₂H | C(O)NHCH₃ | CH₃ | 3-CF₃-pyrazol-1-yl |
| II-B.613 | CF₂H | C(O)NHCH₃ | CH₃ | 4-CF₃-pyrazol-1-yl |
| II-B.614 | CF₂H | C(O)NHCH₃ | CH₃ | 3-CF₃-1,2,4-triazol-1-yl |
| II-B.615 | CF₂H | C(O)NHCH₃ | CH₃ | 1,3,4-thiadiazole-CF₃ |
| II-B.616 | CF₂CF₃ | C(O)NHCH₃ | CH₃ | CF₂CF₃ |
| II-B.617 | CF₂CF₃ | C(O)NHCH₃ | CH₃ | CF₂CF₂CF₃ |
| II-B.618 | CF₂CF₃ | C(O)NHCH₃ | CH₃ | CF₂CF₂CF₂H |
| II-B.619 | CF₂CF₃ | C(O)NHCH₃ | CH₃ | CH₂CF₂CF₃ |
| II-B.620 | CF₂CF₃ | C(O)NHCH₃ | CH₃ | CH₂CF₂CF₂H |
| II-B.621 | CF₂CF₃ | C(O)NHCH₃ | CH₃ | 4-Cl-phenyl |
| II-B.622 | CF₂CF₃ | C(O)NHCH₃ | CH₃ | 3,4-diCl-phenyl |
| II-B.623 | CF₂CF₃ | C(O)NHCH₃ | CH₃ | 4-CF₃-phenyl |
| II-B.624 | CF₂CF₃ | C(O)NHCH₃ | CH₃ | 4-OCF₃-phenyl |

TABLE B-continued

| Number of compound | R¹ | R² | R³ | R⁴ |
|---|---|---|---|---|
| II-B.625 | CF₂CF₃ | C(O)NHCH₃ | CH₃ | 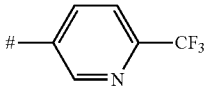 |
| II-B.626 | CF₂CF₃ | C(O)NHCH₃ | CH₃ | 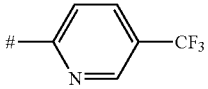 |
| II-B.627 | CF₂CF₃ | C(O)NHCH₃ | CH₃ | 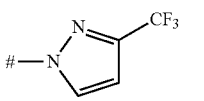 |
| II-B.628 | CF₂CF₃ | C(O)NHCH₃ | CH₃ | 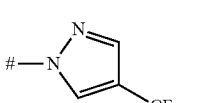 |
| II-B.629 | CF₂CF₃ | C(O)NHCH₃ | CH₃ | 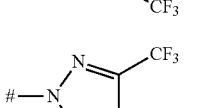 |
| II-B.630 | CF₂CF₃ | C(O)NHCH₃ | CH₃ | 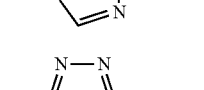 |
| II-B.631 | CF₃ | C(O)N(CH₃)₂ | CH₃ | CF₂CF₃ |
| II-B.632 | CF₃ | C(O)N(CH₃)₂ | CH₃ | CF₂CF₂CF₃ |
| II-B.633 | CF₃ | C(O)N(CH₃)₂ | CH₃ | CF₂CF₂CF₂H |
| II-B.634 | CF₃ | C(O)N(CH₃)₂ | CH₃ | CH₂CF₂CF₃ |
| II-B.635 | CF₃ | C(O)N(CH₃)₂ | CH₃ | CH₂CF₂CF₂H |
| II-B.636 | CF₃ | C(O)N(CH₃)₂ | CH₃ | 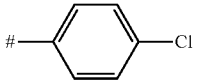 |
| II-B.637 | CF₃ | C(O)N(CH₃)₂ | CH₃ | 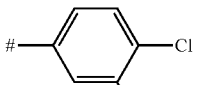 |
| II-B.638 | CF₃ | C(O)N(CH₃)₂ | CH₃ | 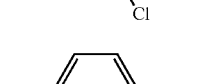 |
| II-B.639 | CF₃ | C(O)N(CH₃)₂ | CH₃ | 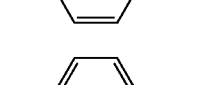 |
| II-B.640 | CF₃ | C(O)N(CH₃)₂ | CH₃ | 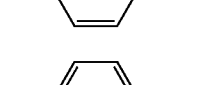 |
| II-B.641 | CF₃ | C(O)N(CH₃)₂ | CH₃ | 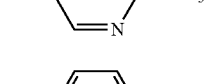 |
| II-B.642 | CF₃ | C(O)N(CH₃)₂ | CH₃ | 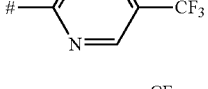 |
| II-B.643 | CF₃ | C(O)N(CH₃)₂ | CH₃ | 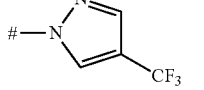 |
| II-B.644 | CF₃ | C(O)N(CH₃)₂ | CH₃ | 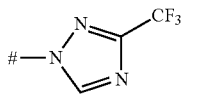 |
| II-B.645 | CF₃ | C(O)N(CH₃)₂ | CH₃ | 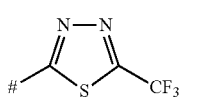 |
| II-B.646 | CF₂H | C(O)N(CH₃)₂ | CH₃ | CF₂CF₃ |
| II-B.647 | CF₂H | C(O)N(CH₃)₂ | CH₃ | CF₂CF₂CF₃ |
| II-B.648 | CF₂H | C(O)N(CH₃)₂ | CH₃ | CF₂CF₂CF₂H |
| II-B.649 | CF₂H | C(O)N(CH₃)₂ | CH₃ | CH₂CF₂CF₃ |
| II-B.650 | CF₂H | C(O)N(CH₃)₂ | CH₃ | CH₂CF₂CF₂H |
| II-B.651 | CF₂H | C(O)N(CH₃)₂ | CH₃ | 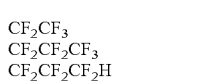 |
| II-B.652 | CF₂H | C(O)N(CH₃)₂ | CH₃ |  |
| II-B.653 | CF₂H | C(O)N(CH₃)₂ | CH₃ | 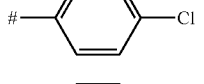 |
| II-B.654 | CF₂H | C(O)N(CH₃)₂ | CH₃ | 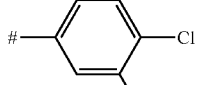 |
| II-B.655 | CF₂H | C(O)N(CH₃)₂ | CH₃ | 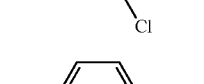 |
| II-B.656 | CF₂H | C(O)N(CH₃)₂ | CH₃ | 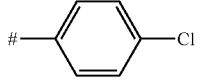 |
| II-B.657 | CF₂H | C(O)N(CH₃)₂ | CH₃ | 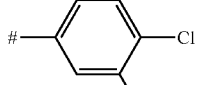 |
| II-B.658 | CF₂H | C(O)N(CH₃)₂ | CH₃ | 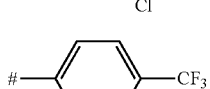 |
| II-B.659 | CF₂H | C(O)N(CH₃)₂ | CH₃ | 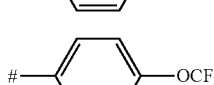 |
| II-B.660 | CF₂H | C(O)N(CH₃)₂ | CH₃ | 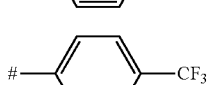 |
| II-B.661 | CF₂CF₃ | C(O)N(CH₃)₂ | CH₃ | CF₂CF₃ |

TABLE B-continued

| Number of compound | R$^1$ | R$^2$ | R$^3$ | R$^4$ |
|---|---|---|---|---|
| II-B.662 | CF$_2$CF$_3$ | C(O)N(CH$_3$)$_2$ | CH$_3$ | CF$_2$CF$_2$CF$_3$ |
| II-B.663 | CF$_2$CF$_3$ | C(O)N(CH$_3$)$_2$ | CH$_3$ | CF$_2$CF$_2$CF$_2$H |
| II-B.664 | CF$_2$CF$_3$ | C(O)N(CH$_3$)$_2$ | CH$_3$ | CH$_2$CF$_2$CF$_3$ |
| II-B.665 | CF$_2$CF$_3$ | C(O)N(CH$_3$)$_2$ | CH$_3$ | CH$_2$CF$_2$CF$_2$H |
| II-B.666 | CF$_2$CF$_3$ | C(O)N(CH$_3$)$_2$ | CH$_3$ | #—⟨C$_6$H$_4$⟩—Cl (4-Cl-phenyl) |
| II-B.667 | CF$_2$CF$_3$ | C(O)N(CH$_3$)$_2$ | CH$_3$ | #—⟨C$_6$H$_3$⟩(Cl)(Cl) (3,4-dichlorophenyl) |
| II-B.668 | CF$_2$CF$_3$ | C(O)N(CH$_3$)$_2$ | CH$_3$ | #—⟨C$_6$H$_4$⟩—CF$_3$ |
| II-B.669 | CF$_2$CF$_3$ | C(O)N(CH$_3$)$_2$ | CH$_3$ | #—⟨C$_6$H$_4$⟩—OCF$_3$ |
| II-B.670 | CF$_2$CF$_3$ | C(O)N(CH$_3$)$_2$ | CH$_3$ | #—⟨pyridyl⟩—CF$_3$ |
| II-B.671 | CF$_2$CF$_3$ | C(O)N(CH$_3$)$_2$ | CH$_3$ | #—⟨pyridyl⟩—CF$_3$ |
| II-B.672 | CF$_2$CF$_3$ | C(O)N(CH$_3$)$_2$ | CH$_3$ | #—N(pyrazolyl)—CF$_3$ |
| II-B.673 | CF$_2$CF$_3$ | C(O)N(CH$_3$)$_2$ | CH$_3$ | #—N(pyrazolyl)—CF$_3$ |
| II-B.674 | CF$_2$CF$_3$ | C(O)N(CH$_3$)$_2$ | CH$_3$ | #—N(triazolyl)—CF$_3$ |
| II-B.675 | CF$_2$CF$_3$ | C(O)N(CH$_3$)$_2$ | CH$_3$ | #—⟨thiadiazolyl⟩—CF$_3$ | wherein # denotes the attachment in the molecule

3. Compounds of Formula II-C

Amongst the compounds of the formula II, preference is also given to compounds of the formula II-C:

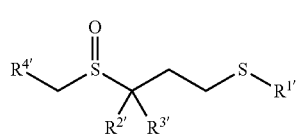

(II-C)

wherein the variables R$^{1'}$, R$^{2'}$, R$^{3'}$ and R$^{4'}$ have the meanings as given above in table A (or table B) for compounds of formula II-A, respectively of formula II-B.

Table C: In analogy to compounds of formula II-A and formula II-B as described above, the definition and combination of the variables in each line of the table A (or table B) given above represent also preferred examples of compounds of formula II-C according to the present invention (Compounds II-C.1 to II-C.675).

4. Formula II-D

Amongst compounds of the formula II, preference is also given to the following compounds of the formula II-D:

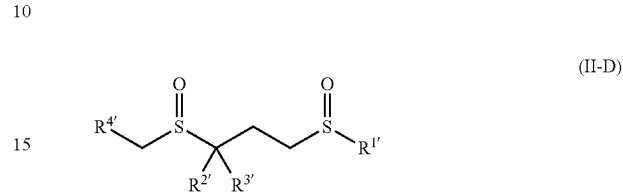

(II-D)

wherein the variables R$^1$, R$^2$, R$^3$ and R$^4$ have the meanings given above in table A (or table B) for compounds of formula II-A, respectively of formula II-B.

Table D: In analogy to compounds of formula II-A and formula II-B as described above, the definition and combination of the variables in each line of the table A (or table B) given above represent also preferred examples of compounds of formula II-D according to the present invention (Compounds II-D.1 to II-D.675).

5. Formula II-E

Amongst compounds of the formula II, preference is also given to the following compounds of the formula II-E:

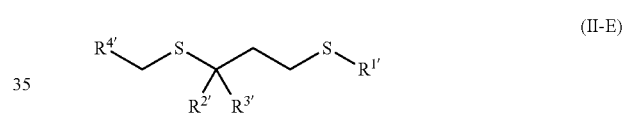

(II-E)

wherein the variables R$^1$, R$^2$, R$^3$ and R$^4$ have the meanings given above in table A (or table B) for compounds of formula II-A, respectively of formula II-B.

Table E: In analogy to compounds of formula II-A and formula II-B as described above, the definition and combination of the variables in each line of the table A (or table B) given above represent also preferred examples of compounds of formula II-E according to the present invention (Compounds II-E.1 to II-E.675).

6. Formula II-F

Amongst compounds of the formula (II), preference is also given to the following compounds of the formula (II-F):

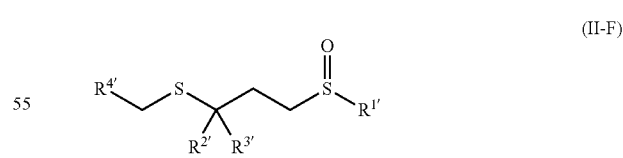

(II-F)

wherein the variables R$^1$, R$^2$, R$^3$ and R$^4$ have the meanings given above in table A (or table B) for compounds of formula II-A, respectively of formula II-B.

Table F: In analogy to compounds of formula II-A and formula II-B as described above, the definition and combination of the variables in each line of the table A (or table B) given above represent also preferred examples of compounds of formula II-F according to the present invention (Compounds II-F.1 to II-F.675).

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) or (II) are also the subject of the invention.

Salts

In addition to the neutral compounds of formula (I) or (II), salt forms of the compounds are also active against animal pests. The terms "veterinarily acceptable salt" and "agriculturally acceptable salt" are used throughout the specification to describe any salts of the compounds that are acceptable for administration for veterinary and agricultural applications, and which provides the active compound upon administration.

In cases where compounds are sufficiently basic or acidic to form stable non-toxic acid or base salts, the compounds may be in the form of a veterinarily or agriculturally acceptable salt. Veterinarily or agriculturally acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily and agriculturally acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Processes for the Preparation of Compounds of Formulae (I) and (II):

The compounds of formula (I) or (II) may be prepared by processes adapted from those described in WO 2008/14332 or WO 2009/005110, both which are hereby incorporated by reference in their entirety. In particular, the compounds of formulae (I) and (II) may be prepared by the processes which are described below. It will be understood by those skilled in the art that certain functional groups in the compounds and intermediates may be unprotected or protected by suitable protecting groups, as taught by Greene et al. *Protective Groups in Organic Synthesis*, John Wiley and Sons, Inc., 3$^{rd}$ edition 1999. Further, it will be apparent to those skilled in the art that the compounds and intermediates may be isolated by standard aqueous work-up conditions and optionally purified. For example, the compounds or intermediates may be purified by chromatographic methods or crystallized to yield the desired product in suitable purity.

In one embodiment, the compounds of formula (I) or (II) may be prepared by reacting an organosulfur compound of formula (A) with a compound of formula (B) as shown in Scheme 1 below, wherein variables m, n, p, $R^1$, $R^2$, $R^3$, $R^4$, $R^5$ and $R^6$ are as described above for the compounds of formula (I) and X represents a leaving group.

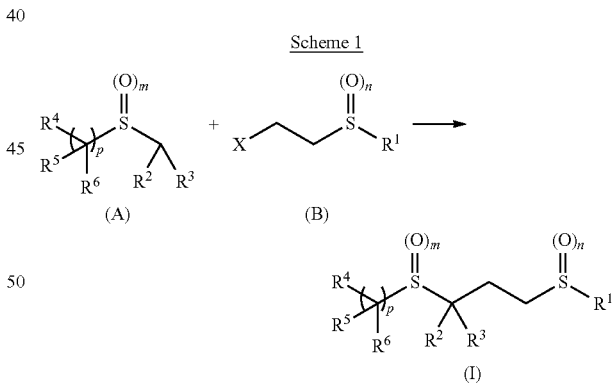

The leaving group X in the compound of formula B is not limited as long as it is sufficiently reactive to be displaced by a reactive anion derived from compound (A). Suitable leaving groups for the reaction are well known in the art and include, but are not limited to, halides such as chloride, bromide, iodide; diazonium salts; aryl-, alkyl- and haloalkyl sulfonates such as tosylate, mesylate and triflate groups; alkylsulfates such as methylsulfate; acetates, trifluoroacetates and the like. The reaction is typically performed in the presence of a suitable base, which is capable of deprotonating the α-proton from compound (A) to form a reactive ion. The specific base is not limited as long as it is capable of forming the anion of compound (A). Suitable bases include strong non-nucleophilic bases such as lithium diisopropyl amide (LDA), lithium bis(trimethylsilyl)amide, potassium t-butoxide and the like. In some embodiments, where $R^2$ or $R^3$ is an electron withdrawing group, such as an ester, amide or a cyano moiety, weak bases such as sodium or potassium carbonate are preferred. In some embodiments, the reaction may be conducted in a solvent, preferably, a polar aprotic solvent.

Compound (A) may be prepared by oxidation of a suitable thioether precursor (C), as shown in Scheme 2 below. Thus, alkylation of thiols (D1) or (E2) with alkylating agents (E1) and (D2), respectively, yields sulfide intermediates (C), which can be oxidized to give sulfoxide or sulfone intermediates (A) by treatment with an oxidizing agent such as a suitable peroxide, peracid, hypochlorite, periodate, or permanganate derivative. Alkylation of thiols is well known in the art, and various conditions may be used (see for example, *J. Org. Chem. USSR* 1960, vol. 2, 16-21 and 24-29; *J. Org. Chem. USSR* 1960, vol. 3, 11-14; Peach, in Patai, "The Chemistry of the Thiol Group," pt. 2, pp. 721-735). X denotes a leaving group such as a halogen atom, methane sulfonate, trifluoromethane sulfonate or toluenesulfonate, or the like. The alkylation reaction is preferably carried out in the presence of a base in a polar aprotic solvent.

Preferred methods for the selective conversion of sulfides (C) to sulfoxides (A), for which m is 1, are the use of hydrogen peroxide as the oxidant in the presence of hexafluoroisopropanol as described in Tetrahedron Lett. 1998, 39, 3141-3144, or the use of meta-chloroperbenzoic acid as the oxidizing agent in the presence or absence of a base in an aprotic solvent such as chloroform or dichloromethane at temperatures below ambient temperature. Other methods for the oxidation of sulfide compounds to sulfoxides and to sulfone products are well known in the art, and any suitable procedure known in the art may be used (for example, for synthesis of sulfoxides see Varma et al., *Org. Lett.*, 1999, 1, 189-191; Kim et al., *Synthesis*, 2002, 2484-2486; Qian et al., *Synlett*, 2006, 709-712; Matteucci et al., *Org. Lett.*, 2003, 5, 235-237; Mba et al., *Org. Lett.*, 2007, 9, 21-24; Karimi et al.; *Org. Leu.*, 2005, 7, 625-628; for preparation of sulfones, see Varma et al., *Org. Lett*, 1999, 1, 189-191; Jana et al., Org. Lett., 2003, 5, 3787-3790; Karimi et al., Org. Lett., 2005, 7, 625-628; Shaabania et al, Tetrahedron, 2004, 60, 11415-11420).

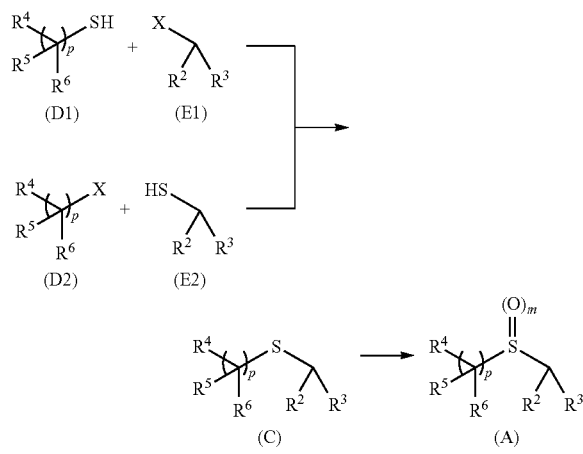

Scheme 4 below illustrates the general preparation of alkylating agents (B) from hydroxy-substituted precursors (F) by activation of the hydroxy functional group as a suitable leaving group X. The synthesis of intermediates of formula (F) is described in WO 2007/147888, which is incorporated herein by reference. As described above, there are no limitations on the leaving group X in the compounds, as long as they impart sufficient reactivity to the intermediates to enable reaction with the desired sulfur nucleophile. Suitable leaving groups X include, but are not limited to, halides, mesylate, triflate or tosylate groups. In some embodiments, the hydroxy group may be converted to a reactive halogen leaving group according to known methods (for example, see Brown, in Patai, "The Chemistry of the Hydroxyl Group," pt. 1, pp. 595-622). Suitable halogenating agents include but are not limited to, thionyl chloride ($SOCl_2$, see Pizey, "Synthetic Reagents," vol. 1, pp. 321-357, Wiley, New York 1974), $PCl_5$, $PCl_3$, $POCl_3$ and the like. In other embodiments, the halide may be formed by reaction of the alcohol with a hydrogen halide acid, optionally in the presence of a catalyst such as zinc chloride. Various other processes known in the art may be used to prepare the desired alkyl halide precursor.

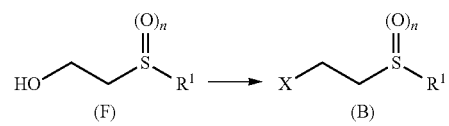

As illustrated in Scheme 5 below, compounds of formula (I), wherein $R^1$, $R^2$, $R^3$, $R^4$, $R^5$, $R^6$, n, m and p are as previously defined, can also be prepared by alkylation of intermediate (D1) with an alkylating agent (G), wherein X denotes a suitable leaving group. This method is preferred for compounds (I), for which m=0.

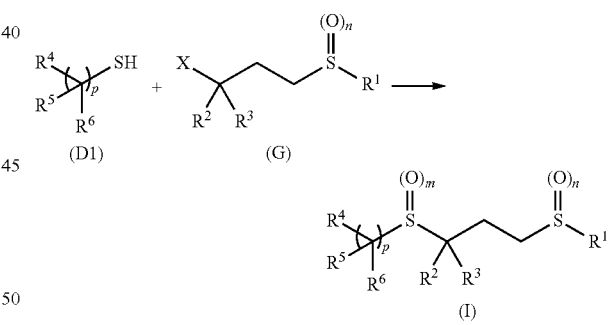

It will be understood by those of skill in the art that compounds of formula (I) may also be prepared by derivatization of other compounds (I) or by customary modifications of the synthesis routes described.

When the compounds of formula (I) or (II) contain suitably acidic or basic residues that enable the formation of veterinarily or agriculturally acceptable salts, the compounds may be reacted with suitable acids such as hydrochloric acid, hydrobromic acid, hydroiodic acid, sulfuric acid, phosphoric acid, formic acid, acetic acid, oxalic acid, benzene sulfonic acid, p-toluene sulfonic acid, dodecylbenzene sulfonic acid, methyl bromide, dimethyl sulfate or diethyl sulfate, and the like, typically at a temperature range of about −5° C. to about 150° C., preferably about 0 to about 20° C., in a suitable solvent.

Alternatively, compounds of formula (I) or (II) that contain acidic residues may be reacted with suitable bases, including organic amine bases or inorganic bases such as hydroxides, carbonates or bicarbonates of alkali metals or alkaline earth metals.

The formation of the salt is usually conducted in a dissolving or diluting agent. Suitable are e.g. aliphatic hydrocarbons as n-pentane, n-hexane or petrol ether, aromatic hydrocarbons, as toluene or xylenes, or ethers such as diethyl ether, methyl-tert.-butyl ether, tetrahydrofuran or dioxane, further ketones, as acetone, methyl-ethyl-ketone or methyl-isopropyl-ketone, as well as halogenated hydrocarbons as chlorobenzene, methylene chloride, ethylene chloride, chloroform or tetrachloroethylene. Also mixtures of those solvents can be used.

For the preparation of salts of compounds of formula (I) or (II) the compounds and salt forming agents are employed usually in a stoichiometric ratio. The excess of one or the other component can be useful.

If individual compounds cannot be prepared via the above-described routes, they can be prepared by derivatization of other compounds or by customary modifications of the synthesis routes described.

The reaction mixtures are typically worked up in a customary manner, for example by mixing a reaction product mixture containing an organic solvent with water, separating the phases, and, if appropriate, purifying the crude products by chromatography, for example on alumina or silica gel. If the intermediates and end products are obtained as solids, they may be purified by recrystallization or digestion.

Pests Controlled:

The compounds of formulae (I) and (II) and their salts are particularly effective for efficiently controlling arthropodal pests such as arachnids, myriapedes and insects as well endoparasites.

Pests controlled by the compounds of formulae (I) and (II) include, for example: Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ipstypographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* spp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes favicollis, Leucotermes favipes, Heterotermes aureus, Reticulitermes favipes, Reticulitermes virginicus, Reticulitermes lucifugus, Reticulitermes santonensis, Reticulitermes* grassei, Termes natalensis, and *Coptotermes formosanus;* cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris,*

*Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Amblyomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius, Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (*Thysanura*), e.g. *Lepisma saccharina* and *Thermobia domestica,* centipedes (*Chilopoda*), e.g. *Scutigera coleoptrata,* millipedes (*Diplopoda*), e.g. *Narceus* spp.,

Earwigs (*Dermaptera*), e.g. *forficula auricularia,* lice (*Phthiraptera*), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* Collembola (springtails), e.g. *Onychiurus* ssp.

They are also effective for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formulae (I) and (II) and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Chorioptes* spp., *Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus*

*telarius* and *Tetranychus urticae, Panonychus ulmi, Panonychus citri,* and *oligonychus pratensis.*

Compounds of the formulae (I) and (II) are particularly useful for controlling insects, preferably sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza fiorum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

Compounds of formulae (I) and (II) are also particularly useful for controlling insects of the orders Hemiptera and Thysanoptera.

Animal Health Applications:

One important aspect of the invention is the use of the compounds of formula (I) or (II) or compositions comprising the compounds for the treatment of parasite infestation/infection in or on animals. The compositions of the invention comprise an effective amount of at least one compound of formula (I) or (II) in combination with a veterinarily acceptable carrier or diluent and optionally other non-active excipients. The compositions may be in a variety of solid and liquid forms which are suitable for various forms of application or administration to an animal. For example, the veterinary compositions comprising the inventive compounds may be in formulations suitable for oral administration, injectable administration, including subcutaneous and parenteral administration, and topical, pour-on, dermal or subdermal administration. The formulations are intended to be administered to an animal including, but is not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

I. Veterinary Compositions:

As discussed above, the compositions of the invention may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and U.S. Pat. No. 4,265,874 (all incorporated herein by reference in their entirety) to form osmotic therapeutic tablets for controlled release.

Oral formulations include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In another embodiment of the invention, the active composition may be administered via a drench, and may be administered either topically or orally. Drench formulations are those in which the liquid-containing compositions of the invention are administered to the mouth or throat of the animal, or poured onto the skin or coat of the animal.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polyinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or polyoxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol.

Among the acceptable vehicles and solvents that may be employed are water, Ringer's solution and isotonic sodium chloride solution. Cosolvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g. a stripe from head to tail of the animal.

Pour-on formulations are described in U.S. Pat. No. 6,010, 710, also incorporated herein by reference. Pour-on formulations may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the formulation is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the formulation.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to about 10% weight/volume. In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

II. Methods of Treatment:

As discussed above, the compounds of formulae (I) and (II) are effective against ectoparasites and endoparasites and may be used to treat and prevent parasitic infestations in or on animals. In one embodiment, the present invention provides a method of treating or preventing an ectoparasitic infection in or on an animal (e.g. a mammal or bird) comprising administering an ectoparasiticidally effective amount of a compound of formula (I) or (II), or verinarily acceptable salts thereof, or a composition of the invention, to the animal.

In another embodiment, the invention provides a method for treating or preventing an endoparasitic infection in an animal, comprising administering an endoparasitically effective amount of a compound of formula (I) or (II), or verinarily acceptable salts thereof, or a composition comprising the compounds, to the animal.

In still another embodiment of the invention, a method is provided for the treatment or prevention of a parasitic infestation at a locus, which comprises administering or applying a parasiticidally effective amount of a compound of formula (I) or (II), or verinarily acceptable salts thereof, to the locus. With respect to animal health applications, "locus" is intended to mean a habitat, breeding ground, area, material or environment in which a parasite is growing or may grow, including in or on an animal.

Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyoma* spp. and the like), and mites (*Demodex* spp., *Sarcoptes* spp., *Otodectes* spp. and the like), lice (*Trichodectes* spp., *Cheyletiella* spp., *Lignonathus* spp., and the like), mosquitoes (*Aedes* spp., *Culex* spp., *Anopheles* spp., and the like) and flies (*Hematobia* spp., *Musca* spp., *Stomoxys* spp., *Dematobia* spp., *Cochliomyia* spp., and the like). In yet another embodiment for the treatment against ectoparasites, the ectoparasite is a flea and/or tick.

Additional examples of ectoparasites include but are not limited to the tick genus *Boophilus*, especially those of the species microplus (cattle tick), decoloratus and annulatus; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesopha-*

*gostumum, Ostertagia, Oxyuris* spp., *Toxocara, Strongyloides, Strongylus* spp., *Toxascaris, Trichinella, Trichuris,* and *Trichostrongylus.*

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna congostumum*, *Ostertagia, Oxyuris* spp., *Toxocara, Strongyloides, Strongylus* spp., *Toxascaris, Trichinella, Trichuris,* and *Trichostrongylus.*

*sanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Anion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lubricoides, Ascaris* spp., *Brugia malayi, Brugia timoni, Bunostomum* spp., *Chabertia* spp., *Clonorchis* spp., *Cooperia* spp., *Dicrocoelium* spp, *Dictyocaulus filaria, Diphyllobothrium Tatum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eniosoma* spp., *Erythroneura* spp., *Eus-* celis bilobatus, Geococcus coffeae, Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva fimbriolata, Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes vaporariorum, Trioza spp., Typhlocyba spp., Unaspis spp., Viteus vitifolii;

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., Rhipiphorothrips cruentatus, *Scirtothrips* spp., *Taeniothrips cardamoni, Thrips* spp.;

(23) from the class of Protozoa, for example, *Eimeria* spp.

In each aspect of the invention, the compounds and compositions of the invention can be applied against a single pest or combinations thereof.

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents may include both ectoparasiticidal and endoparasiticidal agents. Veterinary pharmaceutical agents are well-known in the art (see e.g. *Plumb' Veterinary Drug Handbook*, 5th Edition, ed. Donald C. Plumb, Blackwell Publishing, (2005) or *The Merck Veterinary Manual*, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, penicillins including penicillin G and penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds may be added to the compositions of the invention. Arylpyrazoles may include but are not limited to those described in U.S. Pat. Nos. 6,001,384; 6,010,710; 6,083,519; 6,096,329; 6,174,540; 6,685,954 and U.S. Pat. No. 6,998, 131, all of which are hereby incorporated by reference in their entirety, —each assigned to Merial, Ltd., Duluth, Ga.). A particularly preferred arylpyrazole compound that may be combined with the compounds of the invention is fipronil (5-amino-1-[2,6-dichloro-4-(trifluoromethyl)phenyl]-4-(trifluoromethylsulfinyl)pyrazole-3-carbonitrile, CAS No. 120068-37-3).

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962, 499, 6,221,894 and U.S. Pat. No. 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

The compositions of the invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In another embodiment, the compositions of the invention may be combined with cyclo-depsipeptide anthelmintic compounds including emodepside (see Willson et al., *Parasitology,* January 2003, 126(Pt 1):79-86).

In another embodiment of the invention, the class of acaricides or insecticides known as insect growth regulators (IGRs) may also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748, 356; U.S. Pat. No. 3,818,047; U.S. Pat. No. 4,225,598; U.S. Pat. No. 4,798,837; U.S. Pat. No. 4,751,225, EP 0 179 022 or GB 2 140 010 as well as U.S. Pat. Nos. 6,096,329 and 6,685, 954, all of which are hereby incorporated by reference in their entirety. Examples of IGRs suitable for use may include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that may be combined with the compositions of the invention may be a benzenedisulfonamide compound, which includes but is not limited to clorsulon; or a cestodal agent, which includes but is not limited to praziquantel, pyrantel or morantel.

In some embodiments, a parasiticidal agent that may be combined with the compositions of the invention may be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide may be emodepside.

In other embodiments, an insecticidal agent that may be combined with the compositions of the invention may be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are hereby incorporated by reference in their entirety.

For endoparasites, parasiticides which may be combined include but are not limited to pyrantel, morantel, the benzimidazoles (including albendazole, cambendazole, thiabendazole, fenbendazole, febantel, oxfendazole, oxibendazole, triclabendazole, mebendazole and netobimin), levamisole, closantel, rafoxanide, nitroxynil, disophenol and paraherquamide. For ectoparasites, insecticides which may be combined also include but are not limited to pyrethoids, organophosphates and neonicotinoids such as imidacloprid, as well as compounds such as metaflumizone, amitraz and ryanodine receptor antagonists.

The compositions of the invention may also comprise an antiparasitic macrocyclic lactone compound in combination with the active compound of the invention. The macrocyclic lactones include, but are not limited to, avermectins, such as abamectin, dimadectin, doramectin, emamectin, eprinomectin, ivermectin, latidectin, lepimectin, selamectin, ML-1,694, 554 and milbemycins, such as milbemectin, milbemycin D, moxidectin and nemadectin. Also included are the 5-oxo and 5-oxime derivatives of said avermectins and milbemycins. Examples of compositions comprising macrocyclic lactones include but are not limited to those described in U.S. Pat. Nos. 6,426,333; 6,482,425; 6,962,713 and 6,998,131, all of which are incorporated by reference in their entirety; —each assigned to Merial, Ltd., Duluth, Ga.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569, each of which is incorporated herein by reference. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all of which are incorporated by reference in their entirety. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871, 719, 4,874,749, 4,427,663, 4,310,519, 4,199,569, 5,055,596, 4,973,711, 4,978,677, 4,920,148 and EP 0 667 054, all of which are incorporated by reference in their entirety.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, organophosphate (which included but are not limited to chlorfenvinphos, crotoxyphos, dichlorvos, heptenophos, mevinphos, monocrotophos, naled, TEPP, tetrachlorvinphos) and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In addition to the other active agents mentioned above, combinations of two or more active agents may be used with the compounds of the invention in a composition to treat a desired spectrum of pests and parasites. It would be well within the skill level of the practitioner to decide which individual compound can be used in the inventive formulation to treat a particular infection of an insect.

Agricultural Applications

For use in a method for combating pests that damage plants, plant propagation material and crops, or material derived from wood, according to the present invention, the compounds of formulae (I) and (II) can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula (I) or (II) according to the present invention.

I. Agricultural Compositions

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8, all of which are hereby incorporated by reference in their entirety), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

The following solvents/carriers are suitable for compositions of the invention:

solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methylpyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers include nonionic and anionic emulsifiers (for example polyoxyethylene fatty alcohol ethers, alkylsulfonates and arylsulfonates).

Examples of suitable dispersants include lignin-sulfite waste liquors and methylcellulose.

Suitable surfactants include alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, In some embodiments, anti-freezing agents such as glycerin, ethylene glycol, propylene glycol and bactericides such as can be added to the formulation.

In other embodiments, antifoaming agents may be included in the formulations. Suitable antifoaming agents include antifoaming agents based on silicon or magnesium stearate.

The formulations of the invention may comprise preservatives. Suitable preservatives include, for example, dichlorophenyl and benzyl alcohol hemiformal In other embodiments, the formulations of the invention may include thickeners known in the art. Suitable thickeners include compounds which confer a pseudoplastic flow behavior to the formulation, i.e. high viscosity at rest and low viscosity in the agitated stage. These thickeners include, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations typically comprise from about 0.01 to about 95% by weight, preferably from about 0.1 to about 90% by weight, of the active ingredient. The active ingredients are employed typically have a purity of from about 90% to about 100%, preferably about 95% to about 100% (according to NMR spectrum).

For seed treatment purposes, respective formulations can be diluted 2-10 fold leading to concentrations in the ready to use preparations of about 0.01 to about 60% by weight active compound by weight, preferably about 0.1 to about 40% by weight.

The compound of formula (I) or (II) can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:

1. Products for dilution with water. For seed treatment purposes, such products may be applied to the seed diluted or undiluted.

A) Water-soluble concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-dispersible granules and water-soluble granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-dispersible powders and water-soluble powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from about 0.0001 to about 10%, preferably from about 0.01 to about 1%.

The active ingredients may also be used successfully in the ultra-low-volume process (ULV), it being possible to apply formulations comprising over 95% by weight of active ingredient, or even to apply the active ingredient without additives.

II. Mixtures

In the method of this invention compounds of formula (I) or (II) I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cyloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) 4-[5-(3,5-Dichlorophenyl)-5-trifluoromethyl-4,5-dihydro-isoxazol-3-yl]-N-[(methoxyimino)methyl]-2-methylbenzamide (M22.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2H$—$CF_2$—$CF_2$—$CF_2$—$CH_2$—$C(CN)_2$—$CH_2$—$CH_2$—$CF_3$) (M24.1) and 2-(2,2,3,3,4,4,5,5-octafluoropentyl)-2-(3,3,4,4,4-pentafluorobutyl)-malonodinitrile ($CF_2H$—$CF_2$—$CF_2$—$CF_2$—$CH_2$—$C(CN)_2$—$CH_2$—$CH_2$—$CF_2$—$CF_3$) (M24.2);

M.25. Microbial disruptors: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis;*

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro-1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694. All of the documents referred to above are hereby incorporated by reference in their entirety.

Fungicides that may be mixed with the compounds of the invention include, but are not limited to, acylalanines such as benalaxyl, metalaxyl, ofurace, oxadixyl; amine derivatives such as aldimorph, dodine, dodemorph, fenpropimorph, fenpropidin, guazatine, iminoctadine, spiroxamin, tridemorph; anilinopyrimidines such as pyrimethanil, mepanipyrim or cyrodinyl; antibiotics such as cycloheximid, griseofulvin, kasugamycin, natamycin, polyoxin or streptomycin; azoles such as bitertanol, bromoconazole, cyproconazole, difenoconazole, dinicona-zole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol; dicarboximides such as iprodion, myclozolin, procymidon, vinclozolin; dithiocarbamates such as ferbam, nabam, maneb, mancozeb, metam, metiram, propineb, polycarbamate, thiram, ziram, zineb; heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine; copper fungicides such as Bordeaux mixture, copper acetate, copper oxychloride, basic copper sulfate; nitrophenyl derivatives such as binapacryl, dinocap, dinobuton, nitrophthalisopropyl; phenylpyrroles such as fenpiclonil or fludioxonil, Sulfur; other fungicides such as acibenzolar-S-methyl, benthiavalicarb, carpropamid, chlorothalonil, cyflufenamid, cymoxanil, diclomezin, diclocymet, diethofencarb, edifen-phos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid; strobilurins such as azoxystrobin, dimoxystrobin, fluoxastrobin, kresoxim-methyl, me-tominostrobin, orysastrobin, picoxystrobin or trifloxystrobin; sulfenic acid derivatives such as captafol, captan, dichlofluanid, folpet, tolylfluanid; cinnemamides and analogs such as dimethomorph, flumetover or flumorph.

III. Uses and Methods

Due to their excellent activity, the compounds of formulae (I) and (II) may be used for controlling animal pests. Accordingly, the present invention also provides a method for controlling animal pests, which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula (I) or (II), or a salt thereof, or a composition as defined above.

In one embodiment, the method of the invention serves for protecting plant propagation material (such as seed) and the plant which grows therefrom from animal pest attack or infestation and comprises treating the plant propagation material (such as seed) with a pesticidally effective amount of a compound of formula (I) or (II) or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In one embodiment of the present invention related to agricultural applications, "animal pests" are preferably selected from arthropods and nematodes, more preferably from harmful insects, arachnids and nematodes, and even more preferably from insects, acarids and nematodes.

The invention further provides an agricultural composition for combating such animal pests, which comprises such an amount of at least one compound of formula (I) or (II) or at least one agriculturally useful salt thereof, and at least one inert liquid and/or solid agriculturally acceptable carrier that has a pesticidal action and, if desired, at least one surfactant. Such a composition may contain a single active compound of formula (I) or (II), or a salt thereof, or a mixture of several active compounds of formula (I) or (II), or their salts, according to the present invention. The composition according to the present invention may comprise an individual isomer or mixtures of isomers as well as individual tautomers or mixtures of tautomers.

The animal pest, i.e. the insects, arachnids and nematodes, the plant, soil or water in which the plant is growing can be contacted with the present compounds of formula (I) or (II) or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula (I) or (II) or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habitat, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound of formula (I) or (II). Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

In one embodiment, the compounds of the invention can also be applied preventively to places at which occurrence of the pests is expected.

The compounds of formula (I) or (II) may be also used to protect growing plants from attack or infestation by pests by contacting the plant with a pesticidally effective amount of compounds of formula (I) or (II). As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" refers to any parts of a plant which are propagable. In general, a plant propagation material includes the product of the ripened ovule of gymnosperm and angiosperm plants which occurs after fertilization and some growth within the mother plant and includes seed, fruits, spurious fruits, infructescences and also rhizomes (rootstocks), corms, tubers, bulbs and scions.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35., Curr Opin Chem Biol. 2006 October; 10(5):487-91.

Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from about 0.0001 to about 500 g per 100 m$^2$, preferably from about 0.001 to about 20 g per 100 m$^2$.

Customary application rates in the protection of materials are, for example, from about 0.01 g to about 1000 g of active compound per m$^2$ treated material, desirably from about 0.1 g to about 50 g per m$^2$.

Insecticidal compositions for use in the impregnation of materials typically contain from about 0.001 to about 95 weight %, preferably from about 0.1 to about 45 weight %, and more preferably from about 1 to about 25 weight % of at least one repellent and/or insecticide.

For use in treating crop plants, the rate of application of the active ingredients of this invention may be in the range of about 0.1 g to about 4000 g per hectare, desirably from about 25 g to about 600 g per hectare, more desirably from about 50 g to about 500 g per hectare.

The compounds of formula (I) or (II) are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula (I) or (II) are preferably used in a bait composition. The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from about 0.001 weight % to about 15 weight %, desirably from about 0.001 weight % to about 5% weight % of active compound.

Formulations of compounds of formula (I) or (II) as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used. For use in spray compositions, the content of active ingredient is from about 0.001 to about 80 weights %, preferably from about 0.01 to about 50 weight % and most preferably from about 0.01 to about 15 weight %.

The compounds of formula (I) or (II), or salts thereof, and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula (I) or (II), or salts thereof, and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1, 3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic dienes, such as butadiene. The impregnation of curtains and bednets is done in general by dipping the textile material into emulsions or dispersions of the insecticide or spraying them onto the nets.

The compounds of formula (I) or (II) and their compositions can also be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula (I) or (II) are applied not only to the surrounding soil surface or into the under-floor soil in order to protect wooden materials but can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

IV. Seed Treatment

In some embodiments of the invention, the compounds of formula (I) or (II) are also suitable for the treatment of seeds in order to protect the seed from insect pest, in particular from soil-living insect pests and the resulting plant's roots and shoots against soil pests and foliar insects.

The compounds of formula (I) or (II) are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula (I) or (II), or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed includes, but is not limited to, seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compounds may also be used for the treatment seeds from plants, which tolerate the action of herbicides or fungicides or insecticides owing to breeding, including genetic engineering methods. For example, the active compounds can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259).

Furthermore, the active compounds of the invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is typically carried out by spraying or by dusting the seeds before sowing of the plants and before emergence of the plants.

Compositions which are especially useful for seed treatment include:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include, for example, flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise about 1-800 g/l of active ingredient, about 1-200 g/l Surfactant, about 0 to 200 g/l antifreezing agent, about 0 to 400 g/l of binder, about 0 to 200 g/l of a pigment and up to about 1 liter of a solvent, preferably water.

Especially preferred FS formulations of compounds of formula I for seed treatment usually comprise from about 0.1 to about 80% by weight (1 to 800 g/l) of the active ingredient, from about 0.1 to about 20% by weight (1 to 200 g/l) of at least one surfactant, e.g. about 0.05 to about 5% by weight of a wetter and from about 0.5 to about 15% by weight of a dispersing agent, up to about 20% by weight, e.g. from about 5 to about 20% of an anti-freeze agent, from about 0 to about 15% by weight, e.g. about 1 to about 15% by weight of a pigment and/or a dye, from about 0 to about 40% by weight, e.g. about 1 to about 40% by weight of a binder (sticker/adhesion agent), optionally up to about 5% by weight, e.g. from about 0.1 to about 5% by weight of a thickener, optionally from about 0.1 to about 2% of an anti-foam agent, and optionally a preservative such as a biocide, antioxidant or the like, e.g. in an amount from about 0.01 to about 1% by weight and a filler/vehicle up to 100% by weight.

Seed Treatment formulations may additionally also comprise binders and optionally colorants. Binders can be added to improve the adhesion of the active materials on the seeds after treatment. Suitable binders include, but are not limited to, homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, colorants or dyes may also be included in the formulation. Suitable colorants or dyes for seed treatment formulations include, but are not limited to, Rhodamin B, C.I. Pigment Red 112, C.I. Solvent Red 1, pigment blue 15:4, pigment blue 15:3, pigment blue 15:2, pigment blue 15:1, pigment yellow 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

A gelling agent may also be used in some formulations of the invention. One non-limiting example of a gelling agent is carrageen (Satiagel®)

In the treatment of seed, the application rates of the compounds of formula (I) or (II) are generally from about 0.1 g to about 10 kg per 100 kg of seed, preferably from about 1 g to about 5 kg per 100 kg of seed, more preferably from about 1 g to about 1000 g per 100 kg of seed and in particular from about 1 g to about 200 g per 100 kg of seed.

The invention therefore also relates to seed comprising a compound of formula (I) or (II), or an agriculturally useful salt thereof, as defined herein. The amount of the compound of formula (I) or (II), or the agriculturally useful salt thereof, will in general vary from about 0.1 g to about 10 kg per 100 kg of seed, preferably from about 1 g to about 5 kg per 100 kg of seed, in particular from about 1 g to about 1000 g per 100 kg of seed. The application rate will vary depending on the specific crop, as known to those in skill in the art. For specific crops such as lettuce the rate may be higher than specified above.

EXAMPLES

The following examples are provided to illustrate certain embodiments of the invention and are not to be construed in any way as limiting the scope of the invention.

Synthesis of Representative Compounds

The compounds described in Table 1 below were prepared according to the general synthetic processes described. It will be apparent to those skilled in the art that other compounds of formulae (I) and (II) may be prepared using similar methods by adapting the reagents and conditions to achieve the desired products.

TABLE 1

| Compound | $R^1$ | $R^2$ | $R^3$ | $R^4$ | $R^5$ | $R^6$ | m | n | p |
|---|---|---|---|---|---|---|---|---|---|
| II-1 | $CF_3$ | CN | H | $CF_3$—$CF_2$—$CH_2$— | H | H | 2 | 0 | 1 |
| II-2 | $CF_3$ | CN | $CH_3$ | $CF_3$—$CF_2$—$CH_2$— | H | H | 2 | 0 | 1 |
| II-3 | $CF_3$ | $CO_2Et$ | H | $CF_3$—$CF_2$—$CH_2$— | H | H | 2 | 0 | 1 |
| II-4 | $CF_3$ | $CO_2Et$ | $CH_3$ | $CF_3$—$CF_2$—$CH_2$— | H | H | 2 | 0 | 1 |
| II-5 | $CF_3$ | CN | H | 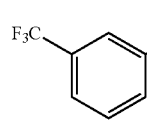 | H | H | 2 | 0 | 1 |
| II-6 | $CF_3$ | CN | $CH_3$ | 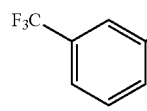 | H | H | 2 | 0 | 1 |
| II-7 | $CF_3$ | CN | H | 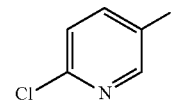 | H | H | 2 | 0 | 1 |
| II-8 | $CF_3$ | CN | $CH_3$ | 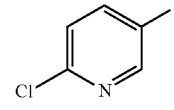 | H | H | 2 | 0 | 1 |
| II-9 | $CF_3$ | CN | H | 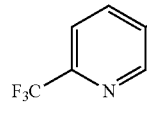 | H | H | 2 | 0 | 1 |
| II-10 | $CF_3$ | CN | $CH_3$ | 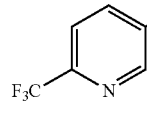 | H | H | 2 | 0 | 1 |
| II-11 | $CF_3$ | CN | H | 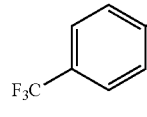 | H | H | 2 | 0 | 1 |
| II-12 | $CF_3$ | CN | $CH_3$ | 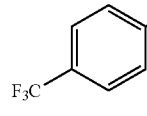 | H | H | 2 | 0 | 1 |

TABLE 1-continued

| Compound | R¹ | R² | R³ | R⁴ | R⁵ | R⁶ | m | n | p |
|---|---|---|---|---|---|---|---|---|---|
| II-13 | $CF_3$ | CN | H | 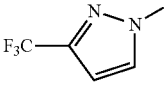 | H | H | 2 | 0 | 1 |
| II-14 | $CF_3$ | CN | $CH_3$ | 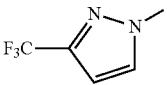 | H | H | 2 | 0 | 1 |
| II-15 | $CF_3$ | CN | H | $CF_3$—$CF_2$—$CH_2$— | H | H | 0 | 0 | 1 |
| II-16 | $CF_3$ | CN | H | $CF_3$—$CF_2$—$CH_2$— | H | H | 1 | 0 | 1 |
| II-17 | $CF_3$ | CN | $CH_3$—$CH_2$— | $CF_3$—$CF_2$—$CH_2$— | H | H | 2 | 0 | 1 |
| II-18 | $CF_3$ | CN | $CH_3$—$CH_2$—$CH_2$— | $CF_3$—$CF_2$—$CH_2$— | H | H | 2 | 0 | 1 |
| II-19 | $CF_3$ | $CO_2H$ | $CH_3$ | $CF_3$—$CF_2$—$CH_2$— | H | H | 2 | 0 | 1 |
| II-20 | $CF_3$ | 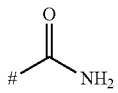 | $CH_3$ | $CF_3$—$CF_2$—$CH_2$— | H | H | 2 | 0 | 1 |
| II-21 | $CF_3$ | 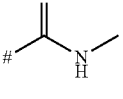 | $CH_3$ | $CF_3$—$CF_2$—$CH_2$— | H | H | 2 | 0 | 1 |
| II-22 | $CF_3$ | 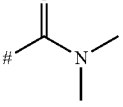 | $CH_3$ | $CF_3$—$CF_2$—$CH_2$— | H | H | 2 | 0 | 1 |
| II-23 | $CF_3$ | 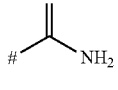 | $CH_3$ | $CF_3$—$CF_2$—$CH_2$— | H | H | 2 | 0 | 1 |
| II-24 | $CF_3$ | CN | H | $CF_3$—$CF_2$—$CF_2$—$CH_2$— | H | H | 2 | 0 | 1 |
| II-25 | $CF_3$ | CN | $CH_3$ | $CF_3$—$CF_2$—$CF_2$—$CH_2$— | H | H | 2 | 0 | 1 |
| II-26 | $CF_3$ | CN | $CH_3$ | $CF_3$—S—$CH_2$— | H | H | 2 | 0 | 1 |
| II-27 | $CF_3$ | $CO_2Et$ | H | 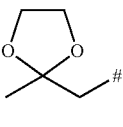 | H | H | 2 | 0 | 1 |
| II-28 | $CF_3$ | CN | H | 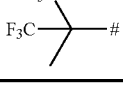 | H | H | 2 | 0 | 1 |

The procedures described in the synthesis examples below can be used to prepare further compounds of formula (I) by appropriate modification of starting materials and intermediates.

Example A 2-(3,3,4,4,4-Pentafluoro-butane-1-sulfonyl)-4-trifluoromethylsulfanyl-butyronitrile (Compound II-1)

A mixture of (3,3,4,4,4-Pentafluoro-butane-1-sulfonyl)-acetonitrile (WO2007/060839) (0.50 g, 1.99 mmol), trifluoro-methanesulfonic acid 2-trifluoromethylsulfanyl-ethyl ester (WO 2007/147888) (0.55 g, 1.99 mmol), and $K_2CO_3$ (0.82 g, 5.97 mmol) in 1,2-dimethoxyethane (20 mL) was stirred under nitrogen at room temperature overnight. The reaction mixture was diluted with $H_2O$ (50 mL) and extracted with ethyl acetate (2×50 mL). The combined organic extracts were washed with brine (100 mL), dried over $Na_2SO_4$ and concentrated under reduced pressure. The residue was purified by column chromatography ($SiO_2$, hexanes/EtOAc 19:1) to afford compound II-1 (0.28 g, 37%) as a white solid.

Mp 95-97° C.; ¹H NMR (300 MHz, $CDCl_3$) δ 4.23 (dd, J=5.7 Hz, 1H), 3.56 (m, 2H), 3.36 (m, 1H), 3.16 (m, 1H) 2.65 (m, 4H) ppm; ¹⁹F NMR (282 MHz, $CDCl_3$) δ −40.9, −85.6, −117.9 ppm; $t_R$=8.16 min.

Example B

2-Methyl-2-(3,3,4,4,4-pentafluoro-butane-1-sulfonyl)-4-trifluoromethyl-sulfanyl-butyronitrile (Compound II-2)

A mixture of compound II-1 (0.35 g, 0.92 mmol), iodomethane (0.26 g, 1.84 mmol), and potassium carbonate (0.38 g, 2.76 mmol) in 1,2-dimethoxyethane (10 mL) was stirred under nitrogen at room temperature overnight. The reaction mixture was diluted with H$_2$O (50 mL) and extracted with ethyl acetate (2×50 mL). The combined organic extracts were washed with saturated NaCl solution (100 mL), dried over Na$_2$SO$_4$ and concentrated under reduced pressure. The residue was purified by column chromatography (SiO$_2$, hexanes/EtOAc 49:1) to yield compound II-2 (0.26 g, 71%) as an off-white solid.

Mp 47-49° C.; $^1$H NMR (300 MHz, CDCl$_3$) δ 3.53 (m, 2H), 3.16 (m, 2H), 2.73 (m, 3H), 2.34 (m, 1H) 1.84 (s, 3H) ppm; $^{19}$F NMR (282 MHz, CDCl$_3$) δ −41.4, −85.6, −118.0 ppm; t$_R$=8.22 min.

Example C

Ethyl 2-(3,3,4,4-Pentafluoro-butane-1-sulfonyl)-4-trifluoromethylsulfanyl-butyrate (Compound II-3)

A mixture of ethyl (3,3,4,4-pentafluoro-butane-1-sulfonyl)-acetate (J. Fluorine Chem. 1985, 28(4), 425-440) (2.00 g, 6.70 mmol), trifluoro-methanesulfonic acid 2-trifluoromethylsulfanyl-ethyl ester (1.50 g, 5.36 mmol), and potassium carbonate (2.77 g, 5.36 mmol) in 1,2-dimethoxyethane (100 mL) was stirred overnight at room temperature under nitrogen. The reaction mixture was diluted with H$_2$O (200 mL) and extracted with ethyl acetate (2×150 mL). The combined organic extracts were washed with brine (200 mL), dried over Na$_2$SO$_4$ and concentrated under reduced pressure. The residue was purified by column chromatography (SiO$_2$, hexanes/CH$_2$Cl$_2$ 1:1) to provide compound II-3 (0.28 g, 37%) as a white solid.

Mp 32-34° C.; $^1$H NMR (300 MHz, CDCl$_3$) δ 4.35 (m, 2H), 4.09 (dd, J=6.6 Hz, 1H), 3.50 (m, 2H), 3.16 (m, 1H) 2.99 (m, 1H); 2.64 (m, 2H), 2.54 (q, J=7.3 Hz, 2H), 1.35 (t, J=7.2 Hz, 3H) ppm; $^{19}$F NMR (282 MHz, CDCl$_3$) δ −41.3, −85.7, −118.2 ppm; t$_R$=8.97 min.

Example D

Ethyl 2-methyl-2-(3,3,4,4,4-pentafluoro-butane-1-sulfonyl)-4-trifluoromethylsulfanyl-butyrate (Compound II-4)

A mixture of compound II-3 (0.85 g, 1.99 mmol), iodomethane (0.56 g, 3.98 mmol), and potassium carbonate (0.82 g, 5.98 mmol) in 1,2-dimethoxyethane (16 mL) was stirred under nitrogen at room temperature overnight. The reaction mixture was diluted with H$_2$O (50 mL) and extracted with ethyl acetate (2×50 mL). The combined organic extracts were washed with brine (100 mL), dried over Na$_2$SO$_4$ and concentrated under reduced pressure. The residue was purified by column chromatography (SiO$_2$, hexanes/CHCl$_3$ 7:3) to provide compound II-4 (0.26 g, 71%) as a colorless liquid.

$^1$H NMR (300 MHz, CDCl$_3$) δ 4.32 (q, J=7.2 Hz, 2H), 3.49 (m, 2H), 3.06 (m, 1H), 2.94 (m, 1H) 2.66 (m, 3H), 2.41 (m, 1H), 1.70 (s, 3H); 1.34 (t, J=7.2 Hz, 3H) ppm; $^{19}$F NMR (282 MHz, CDCl$_3$) δ −41.6, −85.7, −118.2 ppm; t$_R$=9.24 min.

Example E 2-(3-Trifluoromethyl-phenylmethanesulfonyl)-4-trifluoromethylsulfanyl-butyronitrile (Compound II-5)

Compound II-5 was prepared from (3-trifluoromethyl-phenylmethanesulfonyl)-acetonitrile and trifluoro-methanesulfonic acid 2-trifluoromethylsulfanyl-ethyl ester as described for compound II-1.

White solid. Mp 100-102° C.; $^1$H NMR (300 MHz, CDCl$_3$) δ 7.64 (m, 4H), 4.63 (dd, J=14.1 Hz, 2H), 3.94 (dd, J=5.9 Hz, 1H), 3.26 (m, 1H), 3.03 (m, 1H), 2.47 (m, 2H) ppm; $^{19}$F NMR (282 MHz, CDCl$_3$) δ −41.2, −62.3 ppm; t$_R$=11.2 min.

Example F

2-Methyl-2-(3-trifluoromethyl-phenylmethanesulfonyl)-4-trifluoromethylsulfanyl-butyronitrile (Compound II-6)

Compound II-6 was prepared from compound II-5 as described for compound II-2. White solid. Mp 92-94° C.; $^1$H NMR (300 MHz, CDCl$_3$) δ 7.69 (m, 4H), 4.58 (d, J=4.0 Hz, 2H), 3.13 (m, 2H), 2.58 (m, 1H), 2.31 (m, 1H), 1.79 (s, 3H) ppm; $^{19}$F NMR (282 MHz, CDCl$_3$) δ −41.4, −63.2 ppm.

Example G 2-(6-Chloro-pyridin-3-ylmethanesulfonyl)-4-trifluoromethylsulfanyl-butyronitrile (Compound II-7)

Compound II-7 was prepared from (6-chloro-pyridin-3-ylmethanesulfonyl)-acetonitrile and trifluoro-methanesulfonic acid 2-trifluoromethylsulfanyl-ethyl ester as described for compound II-1.

Off-white solid. Mp 122-124° C.; $^1$H NMR (300 MHz, CDCl$_3$) δ 8.44 (s, 1H), 7.86 (dd, J=2.4 Hz, 1H), 7.49 (d, J=8.2 Hz, 1H), 4.66 (s, 2H), 4.48 (dd, J=5.7 Hz, 1H), 3.22 (m, 1H), 3.11 (m, 1H), 2.47 (m, 2H) ppm; $^{19}$F NMR (282 MHz, CDCl$_3$) δ −36.9 ppm; t$_R$=4.74 min.

Example H 2-(6-Chloro-pyridin-3-ylmethanesulfonyl)-2-methyl-4-trifluoromethylsulfanyl-butyronitrile (Compound II-8)

Compound II-8 was prepared from compound II-7 as described for compound II-2.

$^1$H NMR (300 MHz, CDCl$_3$) δ 8.45 (s, 1H), 7.80 (d, J=2.5 Hz, 1H), 7.43 (d, J=8.16 Hz, 1H), 4.48 (dd, J=3.45 Hz, 2H), 3.14 (m, 2H), 2.64 (m, 2H), 2.38 (m, 2H), 1.82 (s, 3H) ppm; $^{19}$F NMR (282 MHz, CDCl$_3$) δ −41.4 ppm.

Example I 2-(6-Trifluoromethyl-pyridin-3-ylmethanesulfonyl)-4-trifluoromethylsulfanyl-butyronitrile (Compound II-9)

Compound II-9 was prepared from (6-trifluoromethyl-pyridin-3-ylmethanesulfonyl)-acetonitrile and trifluoro-methanesulfonic acid 2-trifluoromethylsulfanyl-ethyl ester as described for compound II-1.

Mp 129-130° C.; $^1$H NMR (300 MHz, acetone-d$_6$) δ 8.90 (s, 1H), 8.28 (d, J=8.1 Hz, 1H), 7.97 (d, J=8.1 Hz, 1H), 5.10 (s, 2H), 4.97 (m, 1H), 3.34 (m, 2H), 2.64 (m, 2H) ppm; $^{19}$F NMR (282 MHz, acetone-d$_6$) δ −135.09, −108.46 ppm.

Example J

2-Methyl-2-(6-trifluoromethyl-pyridin-3-ylmethanesulfonyl)-4-trifluoromethylsulfanyl-butyronitrile (Compound II-10)

Compound II-10 was prepared from compound II-9 as described for compound II-2. Mp 109-110° C.; $^1$H NMR (300

MHz, CDCl$_3$) δ 8.78 (s, 1H), 8.04 (d, J=7.8 Hz, 1H), 7.78 (d, J=8.1 Hz, 1H), 4.59 (qd, J=13.2, 5.4 Hz, 2H), 3.16 (m, 2H), 2.63 (m, 1H), 2.36 (m, 1H), 1.85 (s, 3H) ppm; $^{19}$F NMR (282 MHz, CDCl$_3$) δ −68.57, −41.43 ppm.

Example K

2-(4-Trifluoromethyl-phenylmethanesulfonyl)-4-trifluoromethylsulfanyl-butyronitrile (Compound II-11)

Compound II-11 was prepared from (4-trifluoromethyl-phenylmethanesulfonyl)-acetonitrile and trifluoro-methanesulfonic acid 2-trifluoromethylsulfanyl-ethyl ester as described for compound II-1.

Mp 153-155° C.; $^1$H NMR (300 MHz, CDCl$_3$) δ 7.74 (d, J=8.2 Hz, 2H), 7.64 (d, J=8.1 Hz, 2H), 4.61 (qd, J=23.1, 14.0 Hz, 2H), 3.92 (dd, J=6.0 Hz, 1H), 3.25 (m, 1H), 3.02 (m, 1H), 2.47 (m, 2H) ppm; $^{19}$F NMR (282 MHz, CDCl$_3$) δ −41.3, −63.4 ppm.

Example L

2-Methyl-2-(4-trifluoromethyl-phenylmethanesulfonyl)-4-trifluoromethylsulfanyl-butyronitrile (Compound II-12)

Compound II-12 was prepared from compound II-11 as described for compound II-2. Mp 102-104° C.; $^1$H NMR (300 MHz, CDCl$_3$) δ 7.71 (d, J=8.2 Hz, 2H), 7.61 (d, J=8.0 Hz, 2H), 4.61 (qd, J=23.1, 14.0 Hz, 2H), 3.12 (m, 2H), 2.36 (m, 1H), 2.23 (m, 1H), 1.78 (s, 3H) ppm; $^{19}$F NMR (282 MHz, CDCl$_3$) δ −41.4, −63.4 ppm.

Example M

2-(3-Trifluoromethyl-pyrazol-1-ylmethanesulfonyl)-4-trifluoromethylsulfanyl-butyronitrile (Compound II-13)

To a stirred solution of (3-trifluoromethyl-pyrazol-1-yl-methanesulfonyl)-acetonitrile (0.804 g, 3.17 mmol) in anhydrous THF (5 mL) at −30° C. under nitrogen was added LDA (1.58 mL, 3.17 mmol). The reaction mixture was stirred at −30° C. for 30 min, followed by slow addition of a solution of trifluoro-methanesulfonic acid 2-trifluoromethylsulfanyl-ethyl ester (883 mg, 3.17 mmol) in anhydrous THF (5 mL) at −30° C. The mixture was allowed to warm to 20° C. and stirring was continued for additional 3 h. The reaction mixture was quenched with saturated aqueous NH$_4$Cl solution (20 mL) and extracted with EtOAc (3×25 mL). The combined organic layers were washed with saturated aqueous NaCl solution (2×10 mL), dried over Na$_2$SO$_4$ and concentrated under reduced pressure. The residue was purified by column chromatography (SiO$_2$, gradient of hexanes/EtOAc, 1:1→3:7) and then recrystallized from diethyl ether/hexanes to afford compound II-13 (0.35 g, 28%) as a yellow solid.

Mp 65-67° C.; $^1$H NMR (300 MHz, CDCl$_3$) δ 7.73 (d, J=1.5 Hz, 1H), 6.73 (d, J=1.5 Hz, 1H), 5.83 (br d, J=15.0 Hz, 1H), 5.39 (br d, J=15.0 Hz, 1H), 4.54 (q, J=6.15 Hz, 1H), 3.33 (m, 1H), 3.06 (m, 1H), 2.53 (m, 2H) ppm; $^{19}$F NMR (282 MHz, CDCl$_3$) δ −41.19, −63.08 ppm.

Example N

2-Methyl-2-(3-trifluoromethyl-pyrazol-1-ylmethanesulfonyl)-4-trifluoromethylsulfanyl-butyronitrile (Compound II-14)

Compound II-14 was prepared from compound II-13 as described for compound II-2. Yellowish oil. $^1$H NMR (300 MHz, CDCl$_3$) δ 7.79 (dd, J=0.45, 2.5 Hz, 1H), 6.73 (dd, J=0.45, 2.5 Hz, 1H), 5.68 (br d, J=3.0 Hz, 2H), 3.17 (m, 2H), 2.68 (m, 1H), 2.28 (m, 1H), 1.80 (s, 3H) ppm; $^{19}$F NMR (282 MHz, CDCl$_3$) δ −41.52, −63.08 ppm.

Example O

2-(3,3,4,4,4-Pentafluoro-butylsulfanyl)-4-trifluoromethylsulfanyl-butyronitrile (Compound II-15)

To a stirred solution of (3,3,4,4,4-pentafluoro-butylsulfanyl)-acetonitrile (3.4 g, 15.5 mmol) in anhydrous THF (20 mL) at −78° C. was added LDA (8.5 mL, 17.1 mmol). The mixture was stirred at the same temperature for 20 min, followed by dropwise addition of trifluoro-methanesulfonic acid 2-trifluoromethylsulfanyl-ethyl ester (5.4 g, 15.5 mmol) in anhydrous THF (20 mL) at −78° C. The temperature was allowed to rise slowly to room temperature, and the mixture was stirred for 18 h. Upon quenching with saturated aqueous NH$_4$Cl solution (100 mL) and extraction with EtOAc (2×70 mL), the combined organic layers were dried over Na$_2$SO$_4$ and concentrated under reduced pressure. The residue was purified by column chromatography (SiO$_2$, gradient of hexanes/EtOAc 10:0→8:2) to afford the compound II-15 (0.92 g, 17%) as a yellow oil.

$^1$H NMR (300 MHz, CDCl$_3$) δ 3.79 (t, J=7.4 Hz, 1H), 3.20-2.93 (m, 4H), 2.57-2.15 (m, 4H) ppm; $^{19}$F NMR (282 MHz, CDCl$_3$) δ −118.60, −85.76, −41.18 ppm.

Example P

2-(3,3,4,4,4-Pentafluoro-butane-1-sulfinyl)-4-trifluoromethylsulfanyl-butyronitrile (Compound II-16)

To a stirred solution of compound II-15 (110 mg, 0.32 mmol) in a mixture of acetone/H$_2$O (3:2, 2.5 mL) was added aqueous H$_2$O$_2$ solution (30%, 36 mg, 0.32 mmol) and MoO$_2$Cl$_2$ (1 mg, 0.005 mmol) at room temperature. The mixture was stirred for 18 h, then saturated aqueous Na$_2$S$_2$O$_5$ solution (30 mL) was added and the solution was extracted with EtOAc (2×20 mL). The combined organic layers were dried over Na$_2$SO$_4$ and concentrated under reduced pressure. The residue was purified by column chromatography (SiO$_2$, gradient of hexanes/EtOAc 10:0→8:2) to afford compound II-16 (84 mg, 73%) as an off-white solid. Mp 41-43° C.; $^1$H NMR (300 MHz, CDCl$_3$) δ 3.87-3.73 (m, 1H), 3.41-2.93 (m, 4H), 2.77-2.15 (m, 4H) ppm; $^{19}$F NMR (282 MHz, CDCl$_3$) δ −117.77, −85.64, −40.96 ppm.

Example Q

2-Ethyl-2-(3,3,4,4,4-pentafluoro-butane-1-sulfonyl)-4-trifluoromethylsulfanyl-butyronitrile (Compound II-17)

Compound II-17 was prepared from compound II-1 and ethyl iodide as described for compound II-2.

¹H NMR (500 MHz, CDCl₃) δ 3.55 (m, 1H), 3.45 (m, 1H), 3.18 (m, 2H), 2.73 (m, 2H), 2.52 (m, 2H), 2.16 (m, 2H), 1.28 (t, J=7.6 Hz, 3H) ppm.

Example R

2-(3,3,4,4,4-Pentafluoro-butane-1-sulfonyl)-2-(2-trifluoromethylsulfanyl-ethyl)-pentanenitrile (Compound II-18)

Compound II-18 was prepared from compound II-1 and propyl iodide as described for compound II-2.
¹H NMR (500 MHz, CDCl₃) δ 3.55 (m, 1H), 3.45 (m, 1H), 3.18 (m, 2H), 2.73 (m, 2H), 2.53 (m, 2H), 2.03 (m, 2H), 1.65 (m, 2H), 1.10 (t, J=7.3 Hz, 3H) ppm.

Example S

2-Methyl-2-(3,3,4,4,4-pentafluoro-butane-1-sulfonyl)-4-trifluoromethylsulfanyl-butyric acid (Compound II-19)

Acetic acid (4 mL) and conc. H₂SO₄ (4 mL) were added to a solution of compound II-2 (400 mg, 1.02 mmol) in H₂O (4 mL) at 0° C. The solution was stirred at reflux for 3 d, then allowed to cool to room temperature and poured onto ice water. The resulting solution was extracted with CH₂Cl₂ (3×20 mL) and the combined organic phases were washed twice with 3% aqueous HCl solution, dried over Na₂SO₄ and evaporated under reduced pressure. The residue was purified by flash column chromatography (SiO₂, gradient of EtOAc/cyclohexane) to provide compound II-19 (90 mg, 21%).
¹H NMR (500 MHz, CDCl₃) δ 3.53 (m, 2H), 3.04 (m, 2H), 2.67 (m, 3H), 2.44 (ddd, J=13.9, 11.5, 4.8 Hz, 1H), 1.75 (s, 3H) ppm.

Example T

2-Methyl-2-(3,3,4,4,4-pentafluoro-butane-1-sulfonyl)-4-trifluoromethylsulfanyl-butyramide (Compound II-20)

Oxalyl chloride (44 mg, 0.35 mmol) was added to a solution of compound II-19 (95 mg, 0.23 mmol) in CH₂Cl₂ at 0° C. The solution was stirred for 2 h at 20° C. and concentrated under reduced pressure. The residue was redissolved in THF (10 mL) and added dropwise to a saturated solution of NH₃ in THF (30 mL) at 0° C. The solution was stirred 1.5 h at 20° C., then partitioned between saturated aqueous NaHCO₃ solution and EtOAc. The aqueous phase was extracted with EtOAc and the combined organic phases were washed with H₂O and saturated aqueous NaCl solution, dried over Na₂SO₄ and evaporated under reduced pressure. The residue was purified by flash column chromatography (SiO₂, gradient of EtOAc/cyclohexane with 1% MeOH) to provide compound II-20 (50 mg, 53%).
¹H NMR (500 MHz, CDCl₃) δ 6.60 (bs, 1H), 5.74 (bs, 1H), 3.39 (m, 1H), 3.25 (m, 1H), 2.96 (m, 2H), 2.64 (m, 3H), 2.39 (ddd, J=13.7, 11.7, 5.3 Hz, 1H), 1.71 (s, 3H) ppm.

Example U

2,N-Dimethyl-2-(3,3,4,4,4-pentafluoro-butane-1-sulfonyl)-4-trifluoromethylsulfanyl-butyramide (Compound II-21)

Compound II-21 was prepared from compound II-19 and methyl amine as described for compound II-20.
¹H NMR (500 MHz, CDCl₃) δ 3.37 (m, 1H), 3.20 (m, 1H), 2.96 (ddd, J=13.7, 11.9, 5.0 Hz, 1H), 2.91 (d, J=5.0 Hz, 3H), 2.86 (ddd, J=13.7, 11.9, 5.0 Hz, 1H), 2.61 (m, 3H), 2.36 (ddd, J=13.7, 11.9, 5.0 Hz, 1H), 1.70 (s, 3H) ppm.

Example V

2,N,N-Trimethyl-2-(3,3,4,4,4-pentafluoro-butane-1-sulfonyl)-4-trifluoromethylsulfanyl-butyramide (Compound II-22)

Compound II-22 was prepared from compound II-19 and dimethyl amine as described for compound II-20.
¹H NMR (400 MHz, CDCl₃) δ 3.40 (dd, J=10.3, 6.6 Hz, 2H), 3.16 (bs, 6H), 2.92 (m, 4H), 2.61 (m, 2H), 2.25 (m, 1H), 1.85 (s, 3H) ppm.

Example W

2-Methyl-2-(3,3,4,4,4-pentafluoro-butane-1-sulfonyl)-4-trifluoromethylsulfanyl-thiobutyramide (Compound II-23)

Lawesson's reagent (71 mg, 0.18 mmol) was added to a solution of compound II-20 (60 mg, 0.15 mmol) in toluene (5 mL). The solution was heated to reflux for 4 h, then concentrated under reduced pressure. The residue was purified by flash column chromatography (SiO₂, gradient of EtOAc/cyclohexane) to provide compound II-23 (24 mg, 39%).
¹H NMR (500 MHz, CDCl₃) δ 8.03 (bs, 1H), 7.83 (bs, 1H), 3.41 (m, 1H), 3.25 (m, 1H), 2.96 (m, 2H), 2.68 (m, 3H), 2.50 (m, 1H), 1.88 (s, 3H) ppm.

Example X

2-(3,3,4,4,5,5,5-Heptafluoro-pentane-1-sulfonyl)-4-trifluoromethylsulfanyl-butyronitrile (Compound II-24)

Compound II-24 was prepared from (3,3,4,4,5,5,5-heptafluoro-pentane-1-sulfonyl)-acetonitrile and trifluoro-methanesulfonic acid 2-trifluoromethylsulfanyl-ethyl ester as described for compound II-1.
¹H NMR (500 MHz, CDCl₃) δ 4.25 (dd, J=9.2, 5.5 Hz, 1H), 3.62 (ddd, J=13.7, 10.8, 5.8 Hz, 1H), 3.53 (ddd, J=13.7, 10.8, 5.8 Hz, 1H), 3.38 (m, 1H), 3.09 (m, 1H), 3.09 (quint., J=7.6 Hz, 1H), 2.78 (m, 2H), 2.63 (m, 1H), 2.56 (m, 1H).

Example Y

2-(3,3,4,4,5,5,5-Heptafluoro-pentane-1-sulfonyl)-2-methyl-4-trifluoromethylsulfanyl-butyronitrile (Compound II-25)

Compound II-25 was prepared from compound II-24 and methyl iodide as described for compound II-2.
¹H NMR (500 MHz, CDCl₃) δ 3.55 (m, 1H), 3.47 (m, 1H), 3.16 (m, 2H), 2.78 (m, 2H), 2.65 (ddd, J=14.4, 11.8, 5.0 Hz, 1H), 2.35 (ddd, J=14.4, 11.8, 5.0 Hz, 1H), 1.85 (s, 3H) ppm.

Example Z

2-Methyl-4-trifluoromethylsulfanyl-2-(2-trifluoromethylsulfanyl-ethanesulfonyl)-butyronitrile (Compound II-26)

A mixture of (2-trifluoromethylsulfanyl-ethanesulfonyl)-acetonitrile (190 mg, 0.81 mmol), trifluoro-methanesulfonic acid 2-trifluoromethylsulfanyl-ethyl ester (340 mg, 1.22 mmol) and $K_2CO_3$ (340 mg, 2.44 mmol) in 1,2-dimethoxyethane (10 mL) was stirred under nitrogen at room temperature overnight. The reaction mixture was diluted with $H_2O$ (40 mL) and extracted with ethyl acetate (3×30 mL). The combined organic extracts were washed with saturated aqueous NaCl solution, dried over $Na_2SO_4$ and concentrated under reduced pressure. The residue was purified by flash column chromatography ($SiO_2$, gradient of EtOAc/cyclohexane) to afford compound II-26 (20 mg, 7%).

$^1$H NMR (500 MHz, $CDCl_3$) δ 3.68 (m, 1H), 3.60 (m, 1H), 3.44 (m, 2H), 3.15 (m, 3H), 2.62 (ddd, J=14.2, 11.6, 5.3 Hz, 1H), 2.33 (ddd, J=14.2, 11.6, 5.3 Hz, 1H), 1.82 (s, 3H) ppm.

Example AA

2-[2-(2-Methyl-[1,3]-dioxolan-2-yl)-ethanesulfonyl]-4-trifluoromethylsulfanyl-butyric acid ethyl ester (Compound II-27)

Compound II-27 was prepared from [2-(2-methyl-[1,3]dioxolan-2-yl)-ethanesulfonyl]-acetic acid ethyl ester and trifluoro-methanesulfonic acid 2-trifluoromethylsulfanyl-ethyl ester as described for compound II-1.

$^1$H NMR (500 MHz, $CDCl_3$) δ 4.32 (m, 2H), 4.05 (dd, J=8.2, 5.5 Hz, 1H), 3.97 (m, 4H), 3.36 (m, 1H), 3.28 (m, 1H), 3.14 (m, 1H), 2.98 (m, 1H), 2.52 (m, 2H), 2.23 (m, 2H), 1.37 (s, 3H), 1.35 (t, J=7.3 Hz, 3H) ppm.

Example AB

4-Trifluoromethylsulfanyl-2-(3,3,3-trifluoro-2-methyl-2-trifluoromethyl-propane-1-sulfonyl)-butyronitrile (Compound II-28)

Compound II-28 was prepared from (3,3,3-trifluoro-2-methyl-2-trifluoromethyl-propane-1-sulfonyl)-acetonitrile and trifluoro-methanesulfonic acid 2-trifluoromethylsulfanyl-ethyl ester as described for compound II-1.

$^1$H NMR (500 MHz, $CDCl_3$) δ 4.27 (dd, J=9.2, 5.5 Hz, 1H), 3.72 (s, 2H), 3.37 (m, 1H), 3.07 (m, 1H), 3.58 (m, 2H), 1.82 (s, 3H) ppm.

Activity Against Insects

Green Peach Aphid (*Myzus persicae*)

For evaluating control of green peach aphid (*Myzus persicae*) the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds II-1, II-3, II-4, II-15, II-16, II-17, II-22, II-24 and II-25 at 2500 ppm showed over 90% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compounds II-1, II-3, II-4, II-15, II-16, II-19, II-22, II-24 and II-25 at 2500 ppm showed over 90% mortality in comparison with untreated controls.

Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 nl, using a custom built micro atomizer, at two replications.

After application, microtiter plates were incubated at about 28±1° C. and about 80±5% relative humidity for 5 days. Egg and larval mortality was then visually assessed.

In this test, compounds II-1, II-3, II-4, II-14, II-15, II-16, II-17, II-18, II-20, II-21, II-22, II-23 and II-25 at 2500 ppm showed over 90% mortality in comparison with untreated controls.

Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, compounds II-1, II-3, II-4, II-14, II-15, II-16, II-17, II-18, II-19, II-20, II-21, II-22, II-23, II-24, II-25 and II-26 at 2500 ppm showed over 90% mortality in comparison with untreated controls.

Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, compound II-1, II-2, II-15, II-17, II-23 and II-25 at 2500 ppm showed over 90% mortality in comparison with untreated controls.

Diamond Back Moth (*Plutella xylostella*)

The active compound is dissolved at the desired concentration in a mixture of 1:1 (vol:vol) distilled water:actone. The test solution is prepared at the day of use.

Stomach Poison:

Leaves of Chinese cabbage are dipped in test solution and air-dried. Treated leaves are placed in petri dished lined with moist filter paper. Mortality is recorded 24, 72, and 120 hours after treatment.

In this test, compounds II-1 and 11-2 at 500 ppm showed over 90% mortality in comparison with untreated controls.

Comparative Biological Examples

The biological activity shown tables under CB.1 and CB.2 was evaluated on scale range from 0% as showing no biological activity to 100% as having total control. The biological tests were conducted as described above.

Compounds of the present invention showed surprisingly an unexpected higher biological activity in comparison to e.g comparative examples CE.1 and CE.2 disclosed in WO 2008/143332.

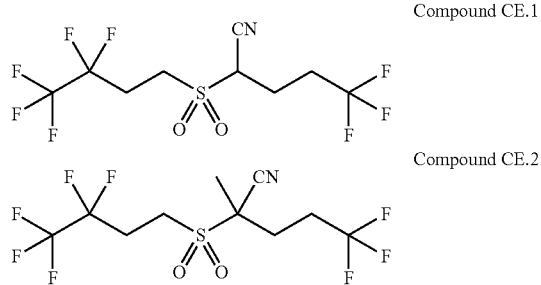

Compound CE.1

Compound CE.2

TABLE CB.1.1

Activity of comparative compounds CE. 1.

| Organism | Concentration In [ppm] | compound example II-1 activity in [%] | comparative example CE. 1 activity in [%] |
|---|---|---|---|
| Heliothis virescens | 800 | 100 | 0 |

TABLE CB.1.2

Activity of comparative compounds CE. 2.

| Organism | Concentration In [ppm] | compound example II-2 activity in [%] | comparative example CE. 2 activity in [%] |
|---|---|---|---|
| Plutella xylostella | 10 | 100 | 0 |

Biological Activity Against Animal Parasites

Activity Against *Caenorhabditis elegans*

Compounds formulated in 100% DMSO are tested in microtiter plates containing 50 µl nematode growth media, 1% *E. coli* and 20 L1 *C. elegans*. The efficacy of a compound is determined based on the motility of the larvae as compared to average motility of control wells containing DMSO only. A dose response assay is conducted with compounds with >80% reduction in motility in the primary assay to determine an $EC_{50}$ value. Selected compounds are further tested against three *C. elegans* strains resistant to known parasiticide classes: avermectins, benzimidazoles, and levamisole to determine any cross resistance potential.

Activity Against *Haemonchus contortus*

Compounds formulated in 100% DMSO are tested in microtiter plates containing 50 µl nematode media, 7% fecal slurry and 20 L1 *H. contortus*. The efficacy of a compound is determined based on the motility of the larvae as compared to average motility of control wells containing DMSO only. An MIC90 value is calculated by determining the lowest dose at which there was a 90% reduction in motility as compared to the control wells.

Activity Against *Aedes aegypti*

Compounds formulated in 100% DMSO are tested in microtiter plates containing 180 ul 1× Luria Broth media and 10 neonate *A. aegypti* larvae. The efficacy of a compound is determined based on the motility of the larvae as compared to average motility of control wells containing DMSO only. A dose response assay is conducted with compounds with >80% reduction in motility in the primary assay to determine an $EC_{50}$ value. Selected compounds are advanced to insecticide secondary assays. In this assay, compounds II-1, II-2, II-3, II-4, II-5, II-6, II-15, II-17, II-18 and II-22 were found to have $EC_{50}$ values of less than 5 ppm.

Insecticide Secondary Assays a. *Ctenocephalides felis* Contact Assay

Compounds are formulated in 100% acetone to final test compound concentrations of 400, 100, 25, 6.25, 1.56 and 0.039 ppm. A substrate is placed in the bottom of a glass scintillation vial and treated with compound and allowed to dry for 3-4 hours. Each vial is infested with 10 adult *C. felis*. The efficacy of a compound is determined based on mortality of *C. felis* up to 72 hours post treatment. A symptomatic effective concentration (SEC) is also calculated for test compounds. This value is generated based on the ability of a compound to affect flea movement; i.e. twitching, falling on side, or inability to stand up. In this assay, compounds II-1, II-2 and II-16 were found to have $EC_{50}$ values of less than 20 ppm.

b. *Rhipicephalus sanguineus* Contact Assay

Compounds formulated in 100% DMSO are diluted in 100% acetone to final test compound concentrations of 50, 12.5, 3.125, 0.78 and 0.195 ppm. Glass vials are treated with formulated compounds and allowed to dry. Filter papers placed in the bottom and lid of the glass vial are treated with compound and allowed to dry for 3-4 hours. Each vial is infested with 10 adult *R. sanguineus*. The efficacy of a compound is determined based on mortality of *R. sanguineus* at 24 and 48 hours post treatment. A symptomatic effective concentration (SEC) is also calculated for test compounds. This value is generated based on the ability of a compound to affect tick movement; i.e. twitching, hyperactivity, or altered movement. In this assay, compounds II-1, II-2 and II-16 were found to have $EC_{50}$ values of less than 10 ppm.

c. *Ctenocephalides felis* Ingestion Assay

Compounds formulated in 100% DMSO are diluted with fresh cow blood to final testing concentrations of 50, 12.5, 3.125, 0.78 and 0.195 ppm. Ten adult *C. felis* are loaded into testing cages and exposed to blood containing the test compound for up to 72 hours. Blood is changed at 24 hour intervals until the test is completed and kept at 37° C. for duration of the test. The efficacy of a compound is determined based on mortality of *C. felis* at 72 hours post treatment. In this assay, compounds II-1, II-2 and II-16 were found to have $EC_{50}$ values of less than 10 ppm.

d. *Stomoxys calcitrans* Contact Assay

Compounds formulated in 100% DMSO are diluted in acetone/water/Triton mixture to final test compound concentrations of 5.2, 1.3, 0.33, 0.08, 0.02 µg/cm². Ten adult *S. calcitrans* are loaded into Petri dishes containing filter papers treated with test compound and held for 24 hours. The efficacy of a compound is determined based on mortality of S. calcitrans at 1, 6 and 24 hours post treatment. A symptomatic effective concentration (SEC) is also calculated for test compounds. This value was generated based on the ability of a compound to affect fly movement; i.e. twitching or altered movement. In this assay, compounds II-1, II-16 and II-17 were found to have an $EC_{50}$ values of less than 1 ppm.

Activity in Rat Ectoparasiticide (Flea) Model

Rats were infested with 50 Ctenocephalides felis fleas. Approximately twenty four hours later rats (3 per group) were treated topically with test compounds. Placebo and positive control groups were included in each study. Forty eight hours post-treatment, fleas were collected from each rat using a flea comb. The percent efficacy per treatment group was calculated using the following formula:

% efficacy=100×(C-T)/C where C is the geometric mean of live fleas recovered in the placebo group and T is the geometric mean of live fleas recovered in the respective treatment group. The results in Table 2 below are means determined from two separate experiments.

TABLE 2

| Compound | Dose | % Efficacy |
|---|---|---|
| II-A.1 | 10 mg/kg | 92 |
| II-A.1 | 20 mg/kg | 98 |
| II-A.451 | 10 mg/kg | 98 |
| II-A.451 | 20 mg/kg | 87 |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. A bis-organo sulfur compound of formula (I):

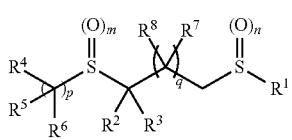

or a veterinarily or agriculturally acceptable salt thereof, wherein:
m=0, 1, 2;
n=0, 1, 2;
p=1, 2 or 3;
q=0, 1, 2, 3 or 4;
$R^1$ is $C_1$-$C_{12}$-haloalkyl, haloalkenyl, haloalkynyl; or
$R^1$ is aryl, aralkyl, heteroaryl, or heterocyclyl each of which is substituted by one or more $R^{10}$;
$R^2$ is cyano, or —C=(G)-$R^9$
$R^3$ is hydrogen, halogen, alkyl, or haloalkyl
$R^4$ is haloalkyl, haloalkenyl, haloalkynyl, or aralkyl, which is substituted by one or more halogen atoms; all of which may be further substituted by one or more $R^{10}$, or
$R^4$ is aryl or a 3- to 7-membered saturated or partially unsaturated heterocyclic ring which may contain 1 to 3 heteroatoms selected from oxygen, sulfur and nitrogen or a 5- to 6-membered heteroaromatic ring which may contain 1 to 3 heteroatoms selected from oxygen, nitrogen and sulfur, wherein aryl, the heterocyclic ring, or the heteroaromatic ring may be fused to another aryl ring or a 5- to 6-membered saturated, partially unsaturated or aromatic heterocyclic ring which may contain 1 to 3 heteroatoms selected from oxygen, nitrogen and sulphur;

and wherein the aryl, heteroaryl or heterocyclic rings or the respective fused ring systems may be unsubstituted or substituted by any combination of 1 to 6 $R^{10}$ groups;

$R^5$, $R^6$, $R^7$ and $R^8$ are independently from each other hydrogen, halogen, alkyl, or haloalkyl;

$R^9$ is alkyl, hydroxy, amino, alkoxy, aryloxy, alkylamino, or dialkylamino, the latter four optionally substituted with halogen;

G is Oxygen or Sulfur; and $R^{10}$=halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, halo alkenylsulfonyl, haloalkynylsulfonyl, alkylamino, alkenylamino, alkynylamino, di(alkyl)amino, di(alkenyl)-amino, di(alkynyl)amino, or trialkylsilyl;

with the proviso that at least one group from $R^2$, $R^3$, $R^4$, $R^5$ and $R^6$ is not hydrogen, alkyl or haloalkyl.

2. The compound of claim 1, wherein n is 0, m is 2, and q is 1.

3. The compound of claim 1, wherein:
$R^1$ is haloalkyl, haloalkenyl or haloalkynyl;
$R^4$ haloalkyl, haloalkenyl or haloalkynyl; and
p and q are independently 1 or 2.

4. The compound of claim 1, wherein:
$R^1$ is haloalkyl, haloalkenyl or haloalkynyl;
$R^4$ is selected from

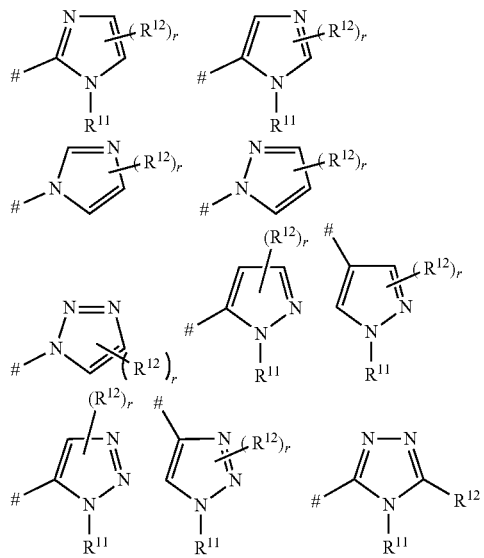

-continued

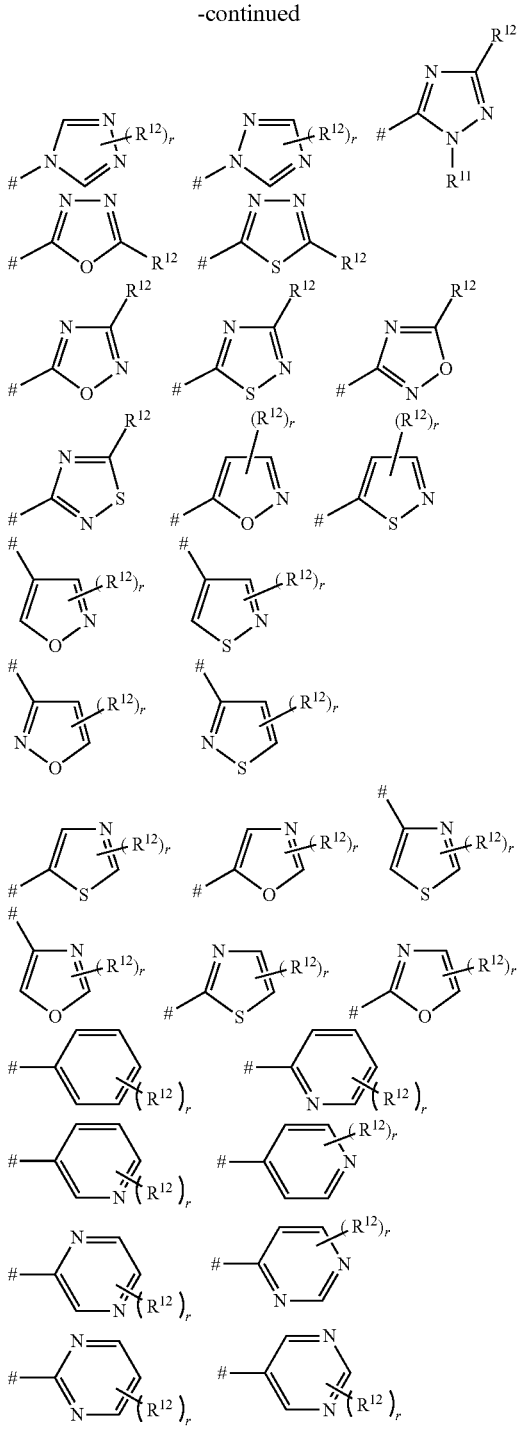

wherein r is 0, 1, 2 or 3,
$R^{11}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl and
$R^{12}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl and
p and q are independently 1 or 2.

5. The compound of claim 1, wherein:
$R^1$ is $C_1$-$C_6$-haloalkyl;
$R^4$ haloalkyl;
$R^2$ is cyano or —C=(G)-$R^9$;
m is 1 or 2;
n is 0;
G is oxygen or sulfur; and
$R^{9'}$ is $C_1$-$C_6$ alkyl, $C_1$-$C_6$ alkoxy, amino, $C_1$-$C_6$ alkylamino, or $C_1$-$C_6$ dialkylamino and p and q are independently 1 or 2.

6. The compound of claim 1, wherein the compound has the formula (II):

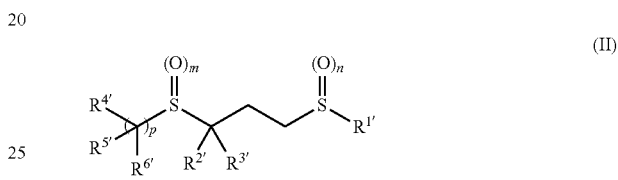

(II)

wherein:
m=0, 1 or 2;
n=0, 1 or 2;
p=1 or 2;
$R^{1'}$ is $C_1$-$C_6$haloalkyl, $C_2$-$C_6$haloalkenyl, $C_2$-$C_6$haloalkynyl; or aryl, aralkyl, heteroaryl, each of which is substituted by one or more halogen atoms; all of which may be further substituted by one or more substituents;
$R^{2'}$ is cyano, or —C=(G)-$R^{7'}$
$R^{3'}$ is hydrogen, halogen, $C_1$-$C_6$-alkyl, or $C_1$-$C_6$-haloalkyl
$R^{4'}$ is $C_1$-$C_6$-haloalkyl, $C_1$-$C_6$-haloalkenyl, or $C_1$-$C_6$-haloalkynyl, each of which is partially or fully halogenated, and which may be further substituted by one or more other substituents; or
$R^{4'}$ is aryl or a 3- to 7-membered saturated or partially unsaturated heterocyclic ring which may contain 1 to 3 heteroatoms selected from oxygen, sulfur and nitrogen or a 5- to 6-membered heteroaromatic ring which may contain 1 to 3 heteroatoms selected from oxygen, nitrogen and sulfur,
wherein aryl, the heterocyclic ring, or the heteroaromatic ring may be fused to another aryl ring or a 5- to 6-membered saturated, partially unsaturated or aromatic heterocyclic ring which may contain 1 to 3 heteroatoms selected from oxygen, nitrogen and sulphur;
aryl, heteroaryl or the respective fused ring systems may be unsubstituted or substituted by any combination of 1 to 6 groups
$R^{5'}$ and $R^{6'}$ are independently from each other hydrogen, halogen, $C_1$-$C_6$-alkyl, or $C_1$-$C_6$-haloalkyl;
$R^{7'}$ is $C_1$-$C_6$alkyl, hydroxy, amino, $C_1$-$C_6$-alkoxy, $C_1$-$C_6$-alkylamino, or $C_1$-$C_6$-dialkylamino, the latter three optionally substituted with halogen;
G is Oxygen or Sulfur; and
$R^{8'}$=halogen, cyano, nitro, hydroxy, mercapto, amino, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_6$-haloalkyl, $C_2$-$C_6$-haloalkenyl, $C_2$-$C_6$-haloalkynyl, $C_3$-$C_6$-halocycloalkyl, $C_3$-$C_6$-halocycloalkenyl, $C_1$-$C_6$-alkoxy, $C_2$-$C_6$— alkenyloxy, $C_2$-$C_6$-alkynyloxy, $C_1$-$C_6$-haloalkoxy, $C_2$-$C_6$-haloalkenyloxy, $C_2$-$C_6$— haloalkynyloxy, $C_3$-$C_6$-cycloalkoxy, $C_3$-$C_6$-cycloalkenyloxy, $C_3$-$C_6$-halocycloalkoxy, $C_3$-$C_6$-halocycloalkenyloxy, $C_1$-$C_6$-alkylthio, $C_1$-$C_6$-haloalkylthio, $C_3$-$C_6$-cycloalkylthio, $C_3$-$C_6$-halocycloalkylthio, $C_1$-$C_6$-alkylsulfinyl, $C_2$-$C_6$-alkenylsulfinyl, $C_2$-$C_6$-alkynyl-sulfinyl, $C_1$-$C_6$— haloalkylsulfinyl, $C_2$-$C_6$-haloalkenylsulfinyl, $C_2$-$C_6$-haloalkynylsulfinyl, $C_1$-$C_6$-alkylsulfonyl, $C_2$-$C_6$-alkenylsulfonyl, $C_2$-$C_6$-alkynylsulfonyl, $C_1$-$C_6$-haloalkyl-sulfonyl, $C_2$-$C_6$-haloalkenylsulfonyl, $C_2$-$C_6$-haloalkynylsulfonyl, $C_1$-$C_6$-alkylamino, $C_2$-$C_6$-alkenylamino, $C_2$-$C_6$-alkynylamino, $C_1$-$C_6$-di(alkyl)amino, di($C_2$-$C_6$-alkenyl)-amino, di($C_2$-$C_6$-alkynyl)amino, or tri($C_1$-$C_{10}$)alkylsilyl.

7. The compound of claim 6, wherein:

$R^{1'}$ is $C_1$-$C_6$haloalkyl;

$R^{2'}$ is cyano or —C=(G)-$R^{7'}$;

$R^{3'}$ is hydrogen, halogen, $C_1$-$C_6$-alkyl;

$R^{4'}$ is $C_1$-$C_6$-haloalkyl;

G is oxygen or sulfur; and $R^{7'}$ is $C_1$-$C_6$alkyl, $C_1$-$C_6$alkoxy, amino, $C_1$-$C_6$alkylamino, or $C_1$-$C_6$dialkylamino.

8. The compound of claim 6, wherein:

$R^{1'}$ is $C_1$-$C_6$haloalkyl;

$R^{2'}$ is cyano or —C=(G)-$R^{7'}$;

$R^{3'}$ is hydrogen, halogen, $C_1$-$C_6$-alkyl;

$R^{4'}$ is phenyl, which may be substituted with one or more halogen atoms, alkyl groups or haloalkyl groups;

G is oxygen or sulfur; and $R^{7'}$ is $C_1$-$C_6$alkyl, $C_1$-$C_6$alkoxy, amino, $C_1$-$C_6$alkylamino, or $C_1$-$C_6$dialkylamino.

9. The compound of claim 6, wherein:

$R^{1'}$ is $C_1$-$C_6$haloalkyl;

$R^{2'}$ is cyano or —C=(G)-$R^{7'}$;

$R^{3'}$ is hydrogen, halogen, $C_1$-$C_6$-alkyl;

$R^{4'}$ is selected from

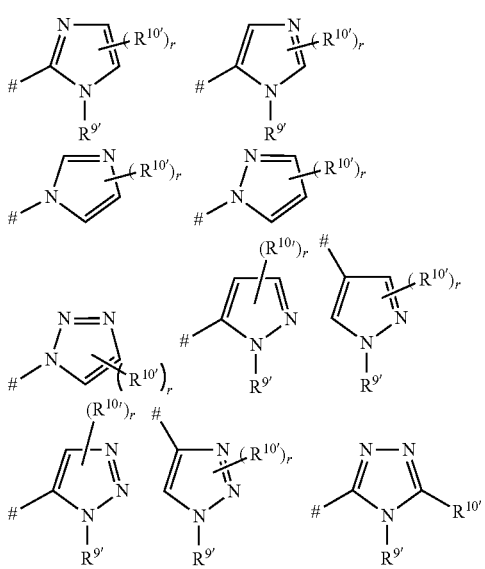

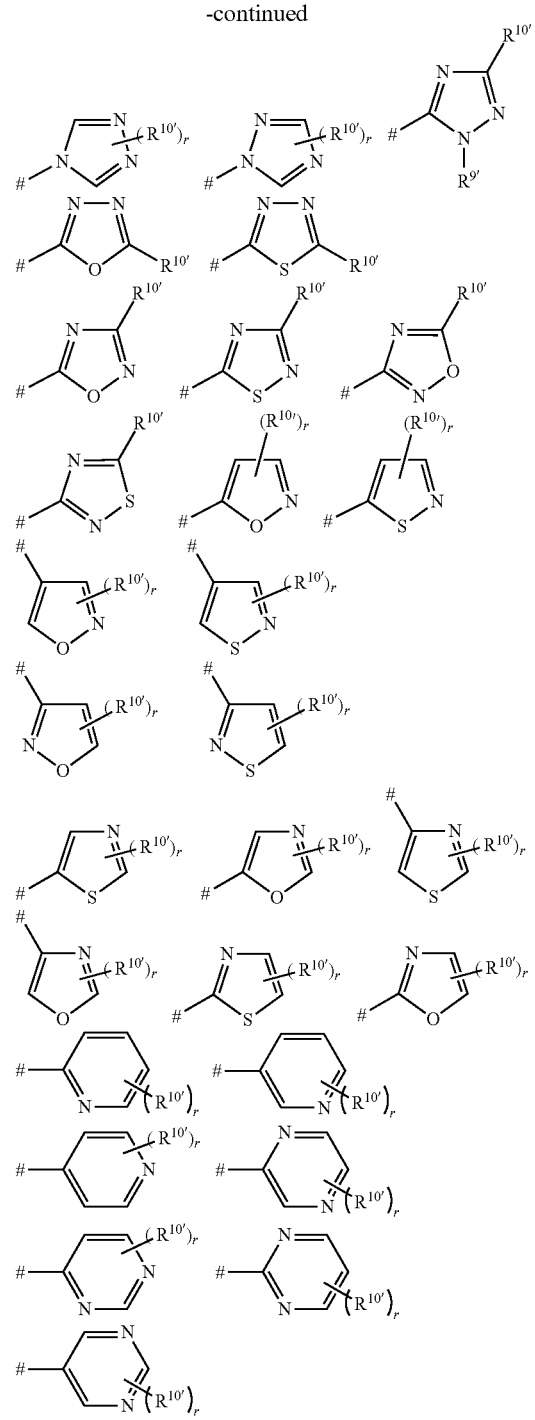

wherein r is 0, 1 or 2 or 3

$R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl and $R^{10'}$ is halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl;

G is oxygen or sulfur; and $R^{7'}$ is $C_1$-$C_6$alkyl, $C_1$-$C_6$alkoxy, amino, $C_1$-$C_6$alkylamino, or $C_1$-$C_6$dialkylamino.

10. The compound of claim 6, wherein:
$R^{1'}$ is $C_1$-$C_6$haloalkyl;
$R^{2'}$ is cyano;
$R^{3'}$ is hydrogen or $C_1$-$C_6$-alkyl;
$R^{4'}$ is $C_1$-$C_6$-haloalkyl; and
$R^{5'}$ and $R^{6'}$ are hydrogen.

11. The compound of claim 6, wherein:
$R^{1'}$ is $C_1$-$C_6$haloalkyl;
$R^{2'}$ is cyano;
$R^{3'}$ is hydrogen or $C_1$-$C_6$-alkyl;
$R^{4'}$ is phenyl, which may be substituted with one or more halogen atoms, alkyl or haloalkyl groups; and
$R^{5'}$ and $R^{6'}$ are hydrogen.

12. The compound of claim 6, wherein:
$R^{1'}$ is $C_1$-$C_6$haloalkyl;
$R^{2'}$ is cyano;
$R^{3'}$ is hydrogen or $C_1$-$C_6$-alkyl;
$R^{4'}$ is selected from wherein r is 1 or 2

$R^{9'}$ is hydrogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, or $C_3$-$C_6$ halocycloalkenyl; and $R^{10'}$ halogen, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_3$-$C_6$ cycloalkenyl, $C_2$-$C_6$ haloalkenyl, $C_3$-$C_6$ halocycloalkenyl, $C_1$-$C_6$ alkoxy, $C_2$-$C_6$ alkenyloxy, $C_2$-$C_6$ alkynyloxy, $C_1$-$C_6$ haloalkoxy, $C_2$-$C_6$ haloalkenyloxy, $C_2$-$C_6$ haloalkynyloxy, $C_3$-$C_6$ cycloalkoxy, $C_3$-$C_6$ cycloalkenyloxy, $C_3$-$C_6$ halocycloalkoxy, $C_3$-$C_6$ halocycloalkenyloxy, $C_1$-$C_6$ alkylthio, $C_1$-$C_6$ haloalkylthio, $C_3$-$C_6$ cycloalkylthio, $C_3$-$C_6$ halocycloalkylthio or trialkylsilyl which may be substituted with one or more substituents selected from halogen, $C_1$-$C_6$ alkyl, $C_3$-$C_6$ cycloalkyl, $C_1$-$C_6$ haloalkyl or $C_3$-$C_6$ halocycloalkyl $R^{5'}$ and $R^{6'}$ are hydrogen.

13. The compound of claim 6, wherein:
$R^{1'}$ is $C_1$-$C_6$fluoroalkyl;
$R^{2'}$ is cyano;
$R^{3'}$ is hydrogen, methyl or trifluoromethyl;
$R^{4'}$ is $C_1$-$C_6$-haloalkyl; and
$R^{5'}$ and $R^{6'}$ are hydrogen.

14. The compound of claim 6, wherein:
$R^{1'}$ is $C_1$-$C_6$fluoroalkyl;
$R^{2'}$ is —C=(G)-$R^{7'}$;
$R^{3'}$ is hydrogen, methyl or trifluoromethyl;
$R^{4'}$ is $C_1$-$C_6$-haloalkyl;
G is oxygen or sulfur; and
$R^{7'}$ is $C_1$-$C_6$alkyl, $C_1$-$C_6$alkoxy, amino, $C_1$-$C_6$alkylamino, or $C_1$-$C_6$dialkylamino.

15. An agricultural or veterinary composition comprising a pesticidally effective amount or a parasiticidally effective amount of the compound of claim 1, or a veterinarily or agriculturally acceptable salt thereof, in combination with a veterinarily or agriculturally acceptable carrier or diluent.

16. The veterinary composition of claim 15, wherein the composition is suitable for oral, injectable or topical administration.

17. The veterinary composition of claim 16, wherein the composition is a spot-on or pour-on composition.

18. A method for controlling a parasitic infestation in or on an animal, comprising administering a parasiticidally effective amount of a compound of claim 1 to the animal.

19. The method of claim 18, wherein the parasite is an endoparasite.

20. The method of claim 18, wherein the parasite is an ectoparasite.

21. A method for controlling infestation of animal pests at a locus, comprising administering a pesticidally effective amount or a parasiticidally effective amount of a compound of claim 1 to the locus.

22. A method for combating or controlling animal pests, comprising contacting the animal pests with a pesticidally effective amount of a compound of claim 1.

23. A method for protecting crops and growing plants from attack or infestation by animal pests, comprising contacting a plant, or soil or water in which the plant is growing, with a compound of claim 1.

24. A method for protecting plant propagation material from attack or infestation by animal pests, comprising contacting a plant, or soil or water in which the plant is growing, with a compound of claim 1.

25. A seed comprising a compound of claim 1 or 6 or an agriculturally useful salt thereof.

26. The seed of claim 25, wherein the compound of claim 1 or 6 or the agriculturally useful salt thereof is present in an amount of from 0.1 g to 10 kg per 100 kg of seed.

* * * * *